(12) United States Patent
Van Camp

(10) Patent No.: US 7,847,157 B2
(45) Date of Patent: Dec. 7, 2010

(54) PLANTS HAVING IMPROVED GROWTH CHARACTERISTICS AND METHOD FOR MAKING THE SAME

(75) Inventor: Wim Van Camp, Sint-Denijs-Westrem (BE)

(73) Assignee: CropDesign N.V. (BE)

( * ) Notice: Subject to any disclaimer, the term of this patent is extended or adjusted under 35 U.S.C. 154(b) by 358 days.

(21) Appl. No.: 11/792,001

(22) PCT Filed: Nov. 30, 2005

(86) PCT No.: PCT/EP2005/056364

§ 371 (c)(1),
(2), (4) Date: Jun. 21, 2007

(87) PCT Pub. No.: WO2006/058897

PCT Pub. Date: Jun. 8, 2006

(65) Prior Publication Data

US 2008/0134355 A1    Jun. 5, 2008

Related U.S. Application Data

(60) Provisional application No. 60/634,015, filed on Dec. 7, 2004.

(30) Foreign Application Priority Data

Dec. 1, 2004    (EP)    ................... 04106225

(51) Int. Cl.
  *C12N 15/82*    (2006.01)
  *A01H 5/00*    (2006.01)
  *A01H 5/10*    (2006.01)

(52) U.S. Cl. ...................... 800/290; 800/298; 800/320; 800/320.1; 800/320.2; 800/320.3; 435/419

(58) Field of Classification Search ....................... None
See application file for complete search history.

(56) References Cited

FOREIGN PATENT DOCUMENTS

| WO | WO 00/52172 | * | 9/2000 |
| WO | WO-00/52172 A1 | | 9/2000 |
| WO | WO-01/31041 A2 | | 5/2001 |

OTHER PUBLICATIONS

Ducommun et al. cdc2 phosphorylation is required for its interaction with cyclin. The EMBO Journal, 1991, vol. 10, No. 11, pp. 3311-3319.*
Qian Y.W. et al. Mitotic effects of a constitutively active mutant of the *Xenopus* polo-like kinase Plx1. Mol Cell Biol. Dec. 1999;19(12):8625-32.*
Hashimoto J. et al. Isolation and characterization of cDNA clones encoding cdc2 homologues from *Oryza sativa*: a functional homologue and cognate variants. Mol Gen Genet. May 1992;233(1-2):10-6.*
Ducommun B. et al. Mutations at sites involved in Suc1 binding inactivate Cdc2., Mol Cell Biol. Dec. 1991;11(12):6177-84, p. 6180.*
Brown, N.R., et al., "Effects of Phosphorylation of Threonine 160 on Cyclin-dependent Kinase 2 Structure and Activity", Journal of Biological Chemistry, vol. 274, No. 13 (1999), pp. 8746-8756.
Marcote, M.J., et al., "A Three-Dimensional Model of the Cdc2 Protein Kinase: Localization of Cyclin-and Suc1-Binding Regions and Phosphorylation Sites", Molecular and Cellular Biology, vol. 13, No. 8 (1993), pp. 5122-5131.
Pickham, K.M., et al., "Requirement of mos[Xe] Protein Kinase for Meiotic Maturation of *Xenopus* Oocytes Induced by a *cdc2* Mutant Lacking Regulatory Phosphorylation Sites", Molecular and Cellular Biology, vol. 12, No. 7 (1992), pp. 3192-3203.

* cited by examiner

*Primary Examiner*—Cynthia Collins
(74) *Attorney, Agent, or Firm*—Connolly Bove Lodge & Hutz LLP

(57) ABSTRACT

The present invention concerns a method for improving growth characteristics of plants by modulating activity of a mutant CDKA kinase or a homologue thereof in a plant and/or modulating expression of a nucleic acid encoding such mutant CDKA. One such method comprises introducing into a plant a mutant CDKA nucleic acid molecule or mutant functional variant thereof. The invention also provides an isolated CKA mutant protein and nucleic acids encoding such protein. The invention furthermore relates to transgenic plants having improved growth characteristics, which plants have modulated expression of a nucleic acid encoding a mutant CDKA kinase. The present invention also concerns constructs useful in the methods of the invention.

18 Claims, 25 Drawing Sheets

SEQ ID NO: 1 CDKA mutant of Oryza sativa (start and stop codon in bold – mutation in bold and underlined)
ATGGAGCAGTACGAGAAGGAGGAGAAGATTGGGGAGGGCACGTACGGGGTGGTGTACAGGGC
GCGGGACAAGGTCACCAACGAGACGATCGCGCTCAAGAAGATCCGGCTTGAGCAGGAGGATG
AGGGCGTCCCCTCCACCGCAATCCGCGAGATCTCGCTCCTCAAGGAGATGCATCACGGCAAC
ATCGTCAGGTTACACGATGTTATCCACAGTGAGAAGCGCATATATCTTGTCTTTGAGTATCT
GGATCTGGACCTAAAGAAGTTCATGGACTCTTGTCCAGAGTTTGCGAAAAACCCCACTTTAA
TTAAGTCATATCTCTATCAGATACTCCGCGGCGTTGCTTACTGTCATTCTCATAGAGTTCTT
CATCGAGATTTGAAACCTCAGAATTTATTGATAGATCGGCGTACTAATGCACTGAAGCTTGC
AGACTTTGGTTTAGCCAGGGCATTTGGAATTCCTGTCCGCACGTTT<u>GAT</u>CACGAGGTTGTAA
CCTTGTGGTATAGAGCTCCAGAGATCCTTCTTGGATCAAGGCAGTATTCTACACCAGTTGAT
ATGTGGTCAGTTGGTTGTATCTTTGCAGAAATGGTGAACCAGAAACCACTGTTCCCTGGTGA
TTCTGAGATTGATGAATTATTTAAGATATTCAGGGTACTAGGAACTCCAAATGAACAAAGTT
GGCCAGGAGTTAGCTCATTACCTGACTACAAGTCTGCTTTCCCCAAGTGGCAGGCACAGGAT
CTTGCAACTATTGTCCCTACTCTTGACCCTGCTGGTTTGGACCTTCTCTCTAAAATGCTTCG
GTACGAGCCAAACAAAAGGATCACAGCTAGACAGGCTCTTGAGCATGAATACTTCAAGGACC
TTGAGATGGTACAATGA

SEQ ID NO: 2 protein sequence based on mutant (mutation in bold and underlined)
MEQYEKEEKIGEGTYGVVYRARDKVTNETIALKKIRLEQEDEGVPSTAIREISLLKEMHHGN
IVRLHDVIHSEKRIYLVFEYLDLDLKKFMDSCPEFAKNPTLIKSYLYQILRGVAYCHSHRVL
HRDLKPQNLLIDRRTNALKLADFGLARAFGIPVRTF<u>D</u>HEVVTLWYRAPEILLGSRQYSTPVD
MWSVGCIFAEMVNQKPLFPGDSEIDELFKIFRVLGTPNEQSWPGVSSLPDYKSAFPKWQAQD
LATIVPTLDPAGLDLLSKMLRYEPNKRITARQALEHEYFKDLEMVQ

SEQ ID NO: 3 prm04553
GGGGACAAGTTTGTACAAAAAAGCAGGCTTCACAATGGAGCAGTACGAGAAGG

SEQ ID NO: 4 prm04554
GGGGACCACTTTGTACAAGAAAGCTGGGTTCATTGTACCATCTCAAGGTC

SEQ ID NO: 5 expression cassette
CGTAGTGGCTGGCTGGGCGACGTGGGTTTAAAGGAAGAGTGACCTGCTCAAGTGCTCAGTAG
ATTAATTAAGGGATTTGAATTCTGGTCGTACGATAAATTAACTTGAGTTCAAAAATACAAGA
AACATCAGTTTATATTTCATTTCGTGTAGGACCTATCAATCCAATTCGTACAAGAGGAATTG
CATATTTCAACTCATAGTCTTAACTACCATTCAAATTGATATTTGCACGATGATGATTGTCT
GGTATAGATTTGACTTTTTGGGAACTGAATCAAATCCAGCATGATTCATGCAAGAAACTTGA
ATTCAACTCATACAAGAAACATATTCAATTTCAAGCTGTGCAATAATGCACGTATCTTAAGC
AAAGAGTAGTACGTCTGCATCATATAGTACTCATGCAAGATTGAAACAGCTAAGAACTTGAT
CAAATTCAAAGTTTTTTTGTGATCGAAGTTTAAATCCAGTTCATACAAGAAACGCATTAAAA
ATAATCGATTTAAATATGAGCAATAATGCATCTACTTTAAGCATAGGGTTTGACATCACGGT
ATGGAAGCAAATTTGAATTAGACGCAAACTTGGATCTCATTTTTCCAGAAACTTTGTTCGAT
TGGTAATTAAAACAGTGCAACCTTTGCACGCAACCAAATATATAAAAATCCCTGGTTGCTAG
GACTGTTGTAATCCTGACAAATTTCCTCTAATCTTAAAACACTTGGGTCGGCTTTCTTTGCC
AACCCGGCGAAAAAAAACTATATAAAAATCATAATTATTACTACCTTCATTTCAGGTTATAA

FIGURE 3

```
GACTTTCTAACATTGTCCATATTTATATATATGTTAATGAATCTAGACATATATTTGTGTCT
GGATTCATTAACATCTATATGAATGTGGACAATGCTAGAAAGTTTTATAACCTGAAACGGAG
AAGTATATTTTTTGGGTACTTGTGTCATATTGTCATGTCATCAATGTGTATAGTACTAAGG
TTCAATGAGAAATGATACAATTGCAAGCCAAACAAATTGCCGTTACAGAAATCTGACGTCAA
CGACATTCTGGCAAGATAATGCTTGATACAATTTGTGCAGCTATGCTACTATAAATAGGGGG
GGGGGGGGCGTTATATCTGCACTGAGTTCATATCAAGCTTTCAATCTCTCATTGCATACAAG
TCCCTGAAGAGTTTACAAGAGACCCAGAAGATCATTTTTTCACCAGCAAAGTTCATTTAAAT
CAACTAGGGATATCACAAGTTTGTACAAAAAAGCAGGCTTCACAATGGAGCAGTACGAGAAG
GAGGAGAAGATTGGGGAGGGCACGTACGGGGTGGTGTACAGGGCGCGGGACAAGGTCACCAA
CGAGACGATCGCGCTCAAGAAGATCCGGCTTGAGCAGGAGGATGAGGGCGTCCCCTCCACCG
CAATCCGCGAGATCTCGCTCCTCAAGGAGATGCATCACGGCAACATCGTCAGGTTACACGAT
GTTATCCACAGTGAGAAGCGCATATATCTTGTCTTTGAGTATCTGGATCTGGACCTAAAGAA
GTTCATGGACTCTTGTCCAGAGTTTGCGAAAAACCCCACTTTAATTAAGTCATATCTCTATC
AGATACTCCGCGGCGTTGCTTACTGTCATTCTCATAGAGTTCTTCATCGAGATTTGAAACCT
CAGAATTTATTGATAGATCGGCGTACTAATGCACTGAAGCTTGCAGACTTTGGTTTAGCCAG
GGCATTTGGAATTCCTGTCCGCACGTTTGATCACGAGGTTGTAACCTTGTGGTATAGAGCTC
CAGAGATCCTTCTTGGATCAAGGCAGTATTCTACACCAGTTGATATGTGGTCAGTTGGTTGT
ATCTTTGCAGAAATGGTGAACCAGAAACCACTGTTCCCTGGTGATTCTGAGATTGATGAATT
ATTTAAGATATTCAGGGTACTAGGAACTCCAAATGAACAAAGTTGGCCAGGAGTTAGCTCAT
TACCTGACTACAAGTCTGCTTTCCCCAAGTGGCAGGCACAGGATCTTGCAACTATTGTCCCT
ACTCTTGACCCTGCTGGTTTGGACCTTCTCTAAAATGCTTCGGTACGAGCCAAACAAAAG
GATCACAGCTAGACAGGCTCTTGAGCATGAATACTTCAAGGACCTTGAGATGGTACAATGAA
CCCAGCTTTCTTGTACAAAGTGGTGATATCACAAGCCCGGGCGGTCTTCTAGGGATAACAGG
GTAATTATATCCCTCTAGATCACAAGCCCGGGCGGTCTTCTACGATGATTGAGTAATAATGT
GTCACGCATCACCATGGGTGGCAGTGTCAGTGTGAGCAATGACCTGAATGAACAATTGAAAT
GAAAAGAAAAAAGTACTCCATCTGTTCCAAATTAAAATTCATTTTAACCTTTTAATAGGTT
TATACAATAATTGATATATGTTTTCTGTATATGTCTAATTTGTTATCATCCGGGCGGTCTTC
TAGGGATAACAGGGTAATTATATCCCTCTAGACAACACACAACAAATAAGAGAAAAAACAAA
TAATATTAATTTGAGAATGAACAAAAGGACCATATCATTCATTAACTCTTCTCCATCCATTT
CCATTTCACAGTTCGATAGCGAAAACCGAATAAAAAACACAGTAAATTACAAGCACAACAAA
TGGTACAAGAAAAACAGTTTTCCCAATGCCATAATACTCGAAC
```

SEQ ID NO: 6 Oryza sativa - metallothionin promoter
```
CGTAGTGGCTGGCTGGGCGACGTGGGTTTAAAGGAAGAGTGACCTGCTCAAGTGCTCAGTAG
ATTAATTAAGGGATTTGAATTCTGGTCGTACGATAAATTAACTTGAGTTCAAAAATACAAGA
AACATCAGTTTATATTTCATTTCGTGTAGGACCTATCAATCCAATTCGTACAAGAGGAATTG
CATATTTCAACTCATAGTCTTAACTACCATTCAAATTGATATTTGCACGATGATGATTGTCT
GGTATAGATTTGACTTTTTGGGAACTGAATCAAATCCAGCATGATTCATGCAAGAAACTTGA
ATTCAACTCATACAAGAAACATATTCAATTTCAAGCTGTGCAATAATGCACGTATCTTAAGC
AAAGAGTAGTACGTCTGCATCATATAGTACTCATGCAAGATTGAAACAGCTAAGAACTTGAT
CAAATTCAAGTTTTTTTGTGATCGAAGTTTAAATCCAGTTCATACAAGAAACGCATTAAAA
ATAATCGATTTAAATATGAGCAATAATGCATCTACTTTAAGCATAGGGTTTGACATCACGGT
ATGGAAGCAAATTTGAATTAGACGCAAACTTGGATCTCATTTTTCCAGAAACTTTGTTCGAT
TGGTAATTAAAACAGTGCAACCTTTGCACGCAACCAAATATATAAAAATCCCTGGTTGCTAG
GACTGTTGTAATCCTGACAAATTTCCTCTAATCTTAAAACACTTGGGTCGGCTTTCTTTGCC
```

FIGURE 3 (continued)

AACCCGGCGAAAAAAAACTATATAAAAATCATAATTATTACTACCTTCATTTCAGGTTATAA
GACTTTCTAACATTGTCCATATTTATATATATGTTAATGAATCTAGACATATATTTGTGTCT
GGATTCATTAACATCTATATGAATGTGGACAATGCTAGAAAGTTTTATAACCTGAAACGGAG
AAGTATATTTTTTTGGGTACTTGTGTCATATTGTCATGTCATCAATGTGTATAGTACTAAGG
TTCAATGAGAAATGATACAATTGCAAGCCAAACAAATTGCCGTTACAGAAATCTGACGTCAA
CGACATTCTGGCAAGATAATGCTTGATACAATTTGTGCAGCTATGCTACTATAAATAGGGGG
GGGGGGGGCGTTATATCTGCACTGAGTTCATATCAAGCTTTCAATCTCTCATTGCATACAAG
TCCCTGAAGAGTTTACAAGAGACCCAGAAG

SEQ ID NO: 7, Oryza sativa CDKA coding sequence (X60374).
Start and stop codon in bold.
ACCTCTCCTCCGATTAATCCCCTCCCCTCCTCTTCCTCCCACTTCTGCGCCTGCTCTTCCTC
CCCTCGCCGACCCTACCTACTCGCGCCGCCGCCGTCGCATTGGGCGGCAAACGGAGGGGGGG
TTAACCCTGATGGAGCAGTACGAGAAGGAGGAGAAGATTGGGGAGGGCACGTACGGGGTGGT
GTACAGGGCGCGGGACAAGGTCACCAACGAGACGATCGCGCTCAAGAAGATCCGGCTTGAGC
AGGAGGATGAGGGCGTCCCCTCCACCGCAATCCGCGAGATCTCGCTCCTCAAGGAGATGCAT
CACGGCAACATCGTCAGGTTACACGATGTTATCCACAGTGAGAAGCGCATATATCTTGTCTT
TGAGTATCTGGATCTGGACCTAAAGAAGTTCATGGACTCTTGTCCAGAGTTTGCGAAAAACC
CCACTTTAATTAAGTCATATCTCTATCAGATACTCCGCGGCGTTGCTTACTGTCATTCTCAT
AGAGTTCTTCATCGAGATTTGAAACCTCAGAATTTATTGATAGATCGGCGTACTAATGCACT
GAAGCTTGCAGACTTTGGTTTAGCCAGGGCATTTGGAATTCCTGTCCGCACGTTTACTCACG
AGGTTGTAACCTTGTGGTATAGAGCTCCAGAGATCCTTCTTGGATCAAGGCAGTATTCTACA
CCAGTTGATATGTGGTCAGTTGGTTGTATCTTTGCAGAAATGGTGAACCAGAAACCACTGTT
CCCTGGTGATTCTGAGATTGATGAATTATTTAAGATATTCAGGGTACTAGGAACTCCAAATG
AACAAAGTTGGCCAGGAGTTAGCTCATTACCTGACTACAAGTCTGCTTTCCCCAAGTGGCAA
GCACAGGATCTTGCAACTATTGTCCCTACTCTTGACCCTGCTGGTTTGGACCTTCTCTCTAA
AATGCTTCGGTACGAGCCAAACAAAAGGATCACAGCTAGACAGGCTCTTGAGCATGAATACT
TCAAGGACCTTGAGATGGTACAATGACCCTGCTATGGCTTTACATTGGATTGGCATATGTAT
GGGCTGGGCTCCTCATTTCATTCCTTCTGTGAACGCTGTGCCCTTCGTTTGGGCATTTTTG

SEQ ID NO: 8, Oryza sativa CDKA (CAA42922)
MEQYEKEEKIGEGTYGVVYRARDKVTNETIALKKIRLEQEDEGVPSTAIREISLLKEMHHGN
IVRLHDVIHSEKRIYLVFEYLDLDLKKFMDSCPEFAKNPTLIKSYLYQILRGVAYCHSHRVL
HRDLKPQNLLIDRRTNALKLADFGLARAFGIPVRTFTHEVVTLWYRAPEILLGSRQYSTPVD
MWSVGCIFAEMVNQKPLFPGDSEIDELFKIFRVLGTPNEQSWPGVSSLPDYKSAFPKWQAQD
LATIVPTLDPAGLDLLSKMLRYEPNKRITARQALEHEYFKDLEMVQ

SEQ ID NO: 9 Allium cepa mRNA for cdc2 kinase, complete cds
(AB006033)
CTCTATATTATTTTGTGGGAGAATTTTGCGCTGGATTCGTTCATCAAACCCTAGCTACAACG
CAGTATGGTTTGGATTGAATGGATCAGTATGAGAAAGTGGAGAAGATTGGAGAAGGAACTTA
TGGAGTTGTTTACAAAGCACGTGATCGGCTGACTAATGAAACGATTGCTTTGAAGAAGATTA
GGTTGGAGCAGGAAGATGAGGGAGTTCCTAGTACTGCCATTAGAGAAATATCACTGTTGAAG
GAAATGCAGCATGCTAACATTGTCAGGCTGCAAGACGTAGTTCATAGTGAGAAGCGAATATA
TCTTGTGTTCGAGTATCTAGATCTGGACCTTAAGAAGCATATGGATTCATGCCCAGATTTTG

FIGURE 3 (continued)

```
CTAAAGATTCTCGTTTGGCTAAAACATTTCTCTATCAGCTTCTCCGAGGAATTGCTTATTGT
CACTCACACCGAGTTCTTCATCGTGACTTAAAGCCTCAAAATTTATTGATCGACAGACGTAC
CAATTCATTAAAGCTTGCTGACTTTGGACTTGCAAGGGCATTTGGTATCCCAGTCCGAACCT
TCACACACGAGGTTGTGACACTGTGGTATAGGGCACCTGAAATCCTCTTAGGTGCTCGTCAG
TATTCTACTCCTGTAGACATATGGTCTGTGGGATGTATCTTTGCTGAAATGGTGAACCAACG
ACCTCTATTCCCTGGGGACTCTGAGATCGACGAGCTGTTCAAAATATTTAGAATTATGGGTA
CCCCAAACGAAGACACATGGCCAGGTGTTACTTCCTTGCCCGACTTCAAGTCTGCTTTTCCA
AAGTGGCCGGCAAAGGACTTGGCAACTATAGTTCCAAAGCTTGATTCAGCTGGAATTGATCT
TCTTTATAAAATGCTGCACCTTGAACCGAGCAAAAGAATCACTGCTCGGAAGGCTCTTGAGC
ATGAATACTTCAGGGATCTTGGACAATTCCATGAAACAACTGAGCACATCCTTCCCCATTG
TATATTATTATGACCATTGCATCAACCTTTGCAGATTGGTATGTTTGAGTGCCGTCCTTTGT
TATCTTTCGGTTTTTTATTCAATCTTATTCAAGTTTGTGTGTTTTAGACAGCTAGGGAGCCT
TCACTTATCCTTATGTTGTAGAAAATACTGTCTCATCTTTTTTGCTTCGTTTTCCTTACCGT
TGTGTGTTCTAAAAGACAATTTTATTTGTACTACTAATATTCTTGTGCTAATGTTACTCCAA
TTTTTGAGTGATCCTTGTAT
```

SEQ ID NO: 10 cdc2 kinase [Allium cepa] (BAA21673)
```
MDQYEKVEKIGEGTYGVVYKARDRLTNETIALKKIRLEQEDEGVPSTAIREISLLKEMQHAN
IVRLQDVVHSEKRIYLVFEYLDLDLKKHMDSCPDFAKDSRLAKTFLYQLLRGIAYCHSHRVL
HRDLKPQNLLIDRRTNSLKLADFGLARAFGIPVRTFTHEVVTLWYRAPEILLGARQYSTPVD
IWSVGCIFAEMVNQRPLFPGDSEIDELFKIFRIMGTPNEDTWPGVTSLPDFKSAFPKWPAKD
LATIVPKLDSAGIDLLYKMLHLEPSKRITARKALEHEYFRDLGTIP
```

**SEQ ID NO: 11 *Antirrhinum* sp mRNA for cyclin-dependent kinase, cdc2a (X97637)**
```
GTACATGGTTTCATCTCATCGATCTCTGATGGAGCAGTATGAAAAGGTTGAGAAGATTGGGG
AGGGAACGTATGGAGTGGTATACAAGGCTCGTGATCGTGTAACAAATGAGACTATAGCCTTG
AAGAAAATCCGTCTAGAGCAGGAAGATGAGGGAGTGCCCAGCACAGCTATCAGAGAGATTTC
TCTCTTGAAAGAGATGCAACATGGGAATATCGTGAGGTTGCAGGATGTGGTGCACAGTGAGA
AGCGCTTGTACCTGGTGTTTGAATATCTGGACTTGGATTTGAAAAAACATATGGATTCATGC
CCAGAATTCTCCCAGGATCCTCGTTTGGTTAAATGTTTCTGTATCAAATACTACGTGGTAT
CGCCTACTGTCATTCTCATCGTGTCCTTCATCGAGATTTGAAGCCTCAAAACTTGCTGATAG
ACCGCCGTACCAATGCATTAAAGCTTGCTGACTTTGGATTGGCCAGAGCATTTGGTATTCCA
GTCAGGACTTTTACACATGAGGTTGTGACACTGTGGTACAGGGCTCCAGAAATACTACTTGG
ATCTCGCCATTATTCTACTCCAGTGGATGTCTGGTCAGTTGGTTGTATATTTGCTGAAATGG
TTAACCAACGGCCTTTGTTTCCTGGGGACTCTGAGATTGATGAACTATTCAAAATTTTTAGA
GTCATGGGTACCCCAAATGAAGAAACATGGCCAGGAGTGACTTCTTTGCCTGATTTAAGTC
AGCATTTCCAAAATGGCCAGCTAAGGAGCTGGCTGCTGTAGTTCCGAATCTTGATGCATCTG
GCCTTGATCTCCTTGATAAAATGCTTCGTTTGGACCCCAGCAAAAGAATTACGGCCAGGAAT
GCTCTTCAGCATGAGTACTTCAAGGATATTGGTTTTGTACCCTGATTGGTGCCCCTCATTCT
GGTACGAGTATATATTGTTATATGACGTCTGGGGTTTTATTCTGTTCCATAGGAATTCGTGA
CAGACGAACGTTATCTCTTGTTTTTGATTCCTTGGGTGTAATTCCATTTATATTGAAGCTGT
GTTGGTTGAAGCAAGTTAGGANTGGCCTCTGCTGGTGCTTTCACTTGCTTTAAACCCCTTGT
GTGATTTTGTCGATTTTTGTTCCTTTTCCATTTTTAATTTCCCTGTAACATCATGCTGATG
TATAACGTTTGAGTTTTTGTTATCTGGTTTAATATATAAATATGGTGTGCCTTTTAGTTGTT
CAAAAAAAAAAAAAAAAAAAAAAAACCATGGTACCCGGATCC
```

FIGURE 3 (continued)

SEQ ID NO: 12 cyclin-dependent kinase [Antirrhinum majus] (CAA66233)
MVSSHRSLMEQYEKVEKIGEGTYGVVYKARDRVTNETIALKKIRLEQEDEGVPSTAIREISL
LKEMQHGNIVRLQDVVHSEKRLYLVFEYLDLDLKKHMDSCPEFSQDPRLVKMFLYQILRGIA
YCHSHRVLHRDLKPQNLLIDRRTNALKLADFGLARAFGIPVRTFTHEVVTLWYRAPEILLGS
RHYSTPVDVWSVGCIFAEMVNQRPLFPGDSEIDELFKIFRVMGTPNEETWPGVTSLPDFKSA
FPKWPAKELAAVVPNLDASGLDLLDKMLRLDPSKRITARNALQHEYFKDIGFVP

SEQ ID NO: 13 Antirrhinum sp mRNA for cyclin-dependent kinase, cdc2b (X97638)
GGATCCGGGTACCATGGAGCATATGGAGTGGTCTATAAGGCTCGTGATATTGAAACAAATGA
GGATATTGCTCTCAAGAAAATCCGGCTGGAGCAGGAAGATGAGGGAGTGCCAAGCACGGCTA
TTAGAGAGATTTCTCTTCTGAAAGAAATGCACCATGAGAACATTGTGAACTTGAAGGATGTT
GTGCACCGTGAGAAACGTTTGTATCTGGTATTTGAATATCTCGACTTGGACTTAAAGAAACA
CATGGATTCCTGCCCAGAATTCTCCCAGGATCTTCATATGGTTAAAATGTTTCTATGTCAAA
TCTTACGCGGAGTTGCCTATTGTCATTCTCATCGCGTTCTTCATCGAGACTTGAAGCCTCAG
AACTTGCTGATAGATAGGGGTAGCAATACAATAAAACTTGCAGATTTTGGATTGGCCAGAGC
ATTTGGTATTCCTGTCAGGACATTTACACACGAGGTTGTGACACTATGGTACAGGGCCCCAG
AAGTACTGCTTGGATCACGCCATTATTCTACTCCAGTTGATGTGTGGTCAGTCGGTTGTATA
TTTGCTGAAATGGTTAACCAGAAACCATTGTTTCCTGGGGATTCTGAGATTGATGAACTCCA
TAAAATTTTTAGAATCATTGGCACCCCGAATGAAGATATATGGCCTGGAGTGACATCTCTGC
CTGATTTCAAATCATCATTTCCAAAATGGCCACCAAAGGAACTGGCAACCATAGTTCCAAAT
CTTGGTGCAACTGGCCTTGATCTCCTTTGTAAAATGCTACAACTAGATCCAAGCAAAAGAAT
TACAGCCAAAAAAGCTCTGGAGCATGAGTACTTTAAGGATATTGTCTTGCCCTGATTAGTGC
CGCTCATCCTGATGCAAAAATGTAAATTGGTATGTGCCATCTTTGGTTTTCATTCTGTCAAA
TAGAATTTTGTGATATATGGGTGATGCATCTCCCTTTTTTGATTCCCTGGGAGTAATTCAAT
TGGTTCTGAGCACAGCAATTTGGAGTTCTAGCTTGCTGGTACTTTGTATTCCTTCTTGTGTG
ATTGTGTCGATATTTCCTTTTGATTCAATTTTGTCGACTTCGTGATAACATCATTCTGATGT
ATGATATATGAGCTTCTGTTCCTCTTAATAGATTACTATGGTGAA

SEQ ID NO: 14 cyclin-dependent kinase [Antirrhinum majus] (CAA66234)
AYGVVYKARDIETNEDIALKKIRLEQEDEGVPSTAIREISLLKEMHHENIVNLKDVVHREKR
LYLVFEYLDLDLKKHMDSCPEFSQDLHMVKMFLCQILRGVAYCHSHRVLHRDLKPQNLLIDR
GSNTIKLADFGLARAFGIPVRTFTHEVVTLWYRAPEVLLGSRHYSTPVDVWSVGCIFAEMVN
QKPLFPGDSEIDELHKIFRIIGTPNEDIWPGVTSLPDFKSSFPKWPPKELATIVPNLGATGL
DLLCKMLQLDPSKRITAKKALEHEYFKDIVLP

SEQ ID NO: 15 A.thaliana protein kinase (cdc2) mRNA, complete cds (M59198)
CTCAAGCTTTTCACAGAAAACCACCACCCTTCTCTCTCTACTGCCTTTTTACCACAGAGAAG
AGAGAGGATCCGTCGGTGTGCTAGTCTCACTGACACTACATCCGATCGTCGCCGGTGACATT
TTATAAGTGTGGAGTTTACTTCAGCTTTATTATTCAGGAATTGATGGATCAGTACGAGAAAG
TTGAGAAGATTGGTGAAGGAACTTACGGTGTGGTTTATAAGGCACGTGACAAAGTGACTAAT
GAGACAATTGCTTTGAAGAAGATCAGGCTAGAGCAGGAGGATGAAGGTGTTCCTAGCACAGC

FIGURE 3 (continued)

```
AATCAGAGAAATCTCCCTCTTGAAAGAAATGCAGCATAGCAACATTGTCAAATTGCAGGATG
TGGTGCACAGCGAGAAACGTTTGTATCTGGTTTTTGAGTATCTTGACTTGGATCTCAAAAAG
CACATGGATTCTACTCCTGATTTCTCCAAGGATCTACATATGATCAAAACATATCTTTACCA
GATTCTCCGTGGAATTGCGTATTGCCACTCTCATAGGGTTCTCCATCGTGATCTGAAGCCAC
AGAATTTGTTGATTGATCGCCGCACAAACTCACTGAAGCTTGCTGATTTTGGACTGGCCAGA
GCATTCGGTATCCCTGTCAGGACATTTACTCATGAGGTTGTTACTCTCTGGTACCGAGCACC
AGAGATACTCCTAGGATCTCATCATTACTCTACACCTGTTGATATTGGTCTGTGGGGTGCA
TATTTGCTGAGATGATCAGCCAAAAGCCCTTATTTCCTGGAGACTCCGAGATTGATCAACTC
TTCAAGATTTTCAGAATCATGGGAACTCCGTACGAGGATACATGGCGTGGGGTAACTTCTCT
ACCGGATTATAAATCTGCTTTCCCTAAATGGAAACCAACGGACCTAGAAACTTTTGTCCCCA
ATCTAGATCCCGATGGAGTCGATCTCCTTTCTAAATGCTGTTAATGGATCCGACCAAAAGA
ATCAACGCAAGAGCCGCCCTGGAGCATGAATACTTCAAGGATCTTGGAGGCATGCCTTAGAA
AGGCATAAAACCAGTAATCTCCTTCATTCTATATATAATTATCAATCCTAAGAAAATGAAGA
ACAATATTAATGGGTTTTGTTTATTCTTTTTCTGAGTTCGTTTCCTACTTATATTCTATTAC
GAAAAAAAGAAAGAAGAAGATTTCGAGTGTGTGTGTTTTTTTACTTCTAAGCTTTTGAGAT
CAGTTTCTTGTATCTTATTTTACCCAGAATATAGTATTTCCCTATATGAAATATGGTTTTTG
TTTTGCAAAATGACCATATTATGCAACTTCTCAGCTTCTTGATT
```

SEQ ID NO: 16 protein kinase (AAA32831)
```
MDQYEKVEKIGEGTYGVVYKARDKVTNETIALKKIRLEQEDEGVPSTAIREISLLKEMQHSN
IVKLQDVVHSEKRLYLVFEYLDLDLKKHMDSTPDFSKDLHMIKTYLYQILRGIAYCHSHRVL
HRDLKPQNLLIDRRTNSLKLADFGLARAFGIPVRTFTHEVVTLWYRAPEILLGSHHYSTPVD
IWSVGCIFAEMISQKPLFPGDSEIDQLFKIFRIMGTPYEDTWRGVTSLPDYKSAFPKWKPTD
LETFVPNLDPDGVDLLSKMLLMDPTKRINARAALEHEYFKDLGGMP
```

SEQ ID NO: 17 (partial sequence) B.vulgaris mRNA for cdc2-related protein kinase (Z71702)
```
TTGGTGAGGGAACTTATGGTGTGGTCTATAAGGCGCGGGACAAGGTTACGAATGAGACTATA
GCTTTGAAGAAAATCCGGTTGGAGCAGGAGGATGAAGGAGTTCCGAGCACGGCGATCAGAGA
AATCTCCCTCTTGAAGGAGATGCAGCATGGCAACATTGTCAGGTTGCAGGATGTAGTGCACA
GTGAGAAGCGCTTGTATTTGGTTTTTGAGTATTTGGACCTAGACTTAAAGAAACACATGGAT
TCATCCCCTGATTTTGCAAAGGATCCACGTATGATTAAAAGGTTTCTTTATCAAATTCTTCG
TGGTATAGCATATTGTCACTCTCATCGTGTCCTGCATCGCGAC
```

SEQ ID NO: 18 cdc2-related protein kinase [Beta vulgaris subsp. vulgaris] (partial sequence, CAA96384)
```
GEGTYGVVYKARDKVTNETIALKKIRLEQEDEGVPSTAIREISLLKEMQHGNIVRLQDVVHS
EKRLYLVFEYLDLDLKKHMDSSPDFAKDPRMIKRFLYQILRGIAYCHSHRVLHRD
```

SEQ ID NO: 19 Brassica napus cyclin dependent protein kinase homolog gene, complete cds (U18365)
```
TATAAACTGCCTTTTCATCCAGAGAGTGAGGATCCGTCGGTGTCACTACATCCGATCGTCGC
CGGTGACGTGTTTCAGCCTAGTTTAATCTTGGAAGTGATGGATCAGTACGAGAAAGTTGAGA
AGATCGGCGAAGGAACTTACGGTGTTGTGTACAAGGCACGAGACAAGGTCACCAATGAGACT
ATTGCTTTGAAGAAGATCCGCCTCGAGCAGGAGGATGAAGGTGTTCCTAGCACTGCCATTAG
```

FIGURE 3 (continued)

```
AGAAATCTCTCTTTTGAAGGAAATGCAGCACAGCAACATTGTCAAGCTGCAGGATGTAGTGC
ACAGCGAGAAGCGTTTGTATCTTGTTTTCGAGTATCTTGACTTGGATCTCAAAAAGCACATG
GACTCTTCTCCTGATTTCTCCAAGGATCTTCATATGATCAAAAGGTATGTTTACCAGATTCT
CCGTGGAATCGCGTATTGCCACTCTCACAGGGTTCTCCATCGTGACCTCAAGCCACAGAATT
TGTTGATTGATCGCCGCACCAACTCACTAAAGCTTGCTGATTTTGGACTGGCCAGAGCTTTC
GGTATCCCTGTCAGGACTTTTACTCATGAGGTGGTTACTCTCTGGTACCGAGCACCAGAGAT
ACTTCTAGGGTCTCATCACTACTCTACACCGGTTGATATTTGGTCTGTGGGATGCATATTTG
CCGAGATGATCAGCCAAAAGCCCTTGTTTCCTGGAGACTCCGAGATTGATCAACTCTTCAAG
ATATTCAGAATCATGGGAACTCCAACGGAGGATACATGGCCTGGGGTAACTTCGCTGCCGGA
TTATAAATCTGCTTTCCCAAAATGGAAACCAACGGACTTGGAATCTTTTGTCCCAAACCTGG
ATCCTAATGGCATAGATCTCCTTTCTAAAATGCTGTTGATGGATCCAACCAAAAGAATCAAC
GCAAGAGCCGCCCTGGAGCATGATTACTTCAAGGATATTGGCGTCATGCCGTAGAGAATGCT
TCAAAACCAGTAGTCTCCTACATTCTCTCTATATATAAGTAATTCGATATCTTCCATCCT
AAGAAAACGAGGTTAAATACATCAATGGTTTTGTTTATTCTTTTGATTTCTTTTAAGTTTG
TTATTCTCTGATACGAAAAATGGAAAAGATTTAGAGTGTGCTTTGTTTATTTCTTCTAAGCT
TTTGAGATCATTTTCTTGTGTATCTTTTTACCAAGTTCAGTAATGTATGGTATTTATTTTGC
```

SEQ ID NO: 20 cyclin dependent protein kinase homolog similar to moth bean p34cdc2 protein (AAA92823)
```
MDQYEKVEKIGEGTYGVVYKARDKVTNETIALKKIRLEQEDEGVPSTAIREISLLKEMQHSN
IVKLQDVVHSEKRLYLVFEYLDLDLKKHMDSSPDFSKDLHMIKRYVYQILRGIAYCHSHRVL
HRDLKPQNLLIDRRTNSLKLADFGLARAFGIPVRTFTHEVVTLWYRAPEILLGSHHYSTPVD
IWSVGCIFAEMISQKPLFPGDSEIDQLFKIFRIMGTPTEDTWPGVTSLPDYKSAFPKWKPTD
LESFVPNLDPNGIDLLSKMLLMDPTKRINARAALEHDYFKDIGVMP
```

SEQ ID NO: 21 C.rubrum mRNA for cyclin dependent kinase p34 (Y10160)
```
TATTTCTATCCTCCATTGAAGCAGTTTCTGAGTGGTAGAGATACGGGACGAAATGGATCAGT
ATGAAAAAGTTGAGAAGATAGGGGAAGGAACCTATGGAGTGGTTTATAAGGCGCGGGACAAG
GTTACGAACGAGACTATAGCTTTGAAGAAAATTCGGTTGGAACAGGAGGATGAGGGAGTTCC
GAGCACGGCGATCAGAGAAATATCACTTTTGAAGGAGATGCAGCATGGCAACATTGTCAGGT
TGCAGGATGTGGTGCATAGTGAGAAGCGCTTATATCTGGTTTTTGAGTATTTGGACCTTGAT
TTGAAGAAACACATGGATTCATGCCCTGATTTTGCAAAGGATCCACGTATGATTAAAAGGTT
TCTTTATCAGATTCTTCGTGGTATCGCTTATTGTCACTCTCATAGGGTCCTGCACCGAGATC
TGAAGCCGCAGAATCTGTTGATAGATCGCCAAACTAATGCACTAAAACTTGCAGATTTTGGA
TTGGCAAGGGCATTTGGTATTCCTGTGAGGACTTTTACACATGAGGTGGTGACATTGTGGTA
CAGAGCTCCAGAAATATTGCTTGGATCTCGACATTACTCTACTCCTGTGGATGTGTGGTCTG
TGGGTTGTATCTTTGCTGAGATGGTGAATCAGAAGCCATTATTTCCTGGAGATTCCGAGATT
GATGAACTTTTCAAGATTTTCAGGACCTTGGGTACACCAAATGAGGAGACATGGCCTGGAGT
GACCTCCCTTCCCGATTTCAAATCTTCATTTCCTAAATGGATCTCCAAGGATTTGTCTGCAG
TAGTACCAAATCTTGATCCAGCTGGTATTGATCTTCTAAATAAAATGCTTTGCTTGGATCCG
AGCAAAAGGATTACAGCCAGGAATGCTCTTGAACATGAATACTTCAAGGACATTGGTTTTGT
ACCCTGATTTCTGTTCATCGCCTTCCAGGTTATCTCGTGTGAATATTGGAAGTTAAGGAAAA
```

AAGATTCTGTTGATTTATTTTCCGCGGGTGAAATGTGTGCAATTGTTGTAGATTTTTTTGA
TGCTATGCTTACCATTGTTCTTTGCCAGGACTTCATGTCGTGTAATTGACTGTTCTGCATTG
GGATTGAGAACTTTGTGAAGCCCCATTGCGATGTGCAAATTATACCCGTCTTCCATATCACT
CCTAAATTGCTTGAATGTGACCCATCTATGGGCTTCTATTATTTAATCAAGATTGATTTTTT
CTATTGCAAAAAAAAAAAAAAAAAAAACTCGAG

SEQ ID NO: 22 cyclin dependent kinase p34 [Chenopodium rubrum]
(CAA71242)
MDQYEKVEKIGEGTYGVVYKARDKVTNETIALKKIRLEQEDEGVPSTAIREISLLKEMQHGN
IVRLQDVVHSEKRLYLVFEYLDLDLKKHMDSCPDFAKDPRMIKRFLYQILRGIAYCHSHRVL
HRDLKPQNLLIDRQTNALKLADFGLARAFGIPVRTFTHEVVTLWYRAPEILLGSRHYSTPVD
VWSVGCIFAEMVNQKPLFPGDSEIDELFKIFRTLGTPNEETWPGVTSLPDFKSSFPKWISKD
LSAVVPNLDPAGIDLLNKMLCLDPSKRITARNALEHEYFKDIGFVP

SEQ ID NO: 23 Glycine max cv Prize protein kinase mRNA
(M93140)
CGCTTACAGTAAGAGGTGAGAAAGAGAGACAAATCGGCAGAAGCAAGGAGGCTGAGAGCGAG
AGAGCAACTGCACGCACTGTAACTCCTAACTTCCCAGATCGTCTTCTTCCTCTTTTCTCTCC
GGTGATTGTTGGAACTCAGAGAGCTTCTTTGATGGAACAGTACGAGAAGGTTGAGAAGATAG
GCGAAGGAACATACGGCGTCGTTTACAAGGGTCGCGACCGCGTCACCAACGAGACCATCGCG
TTGAAGAAGATTCGCCTCGAGCAGGAGGATGAGGGGGTTCCCAGCACCGCCATTCGCGAGAT
TTCTCTCTTGAAAGAAATGCAGCACAGGAACATTGTTAGGTTGCAGGATGTAGTGCACGATG
AGAAGAGTTTGTATCTGGTTTTTGAGTACCTTGACTTAGATCTAAAGAAGCACATGGATTCA
TCTCCAGAATTTGCAAAAGATCCACGACAAGTAAAAATGTTCCTGTACCAAATTCTCTGTGG
CATTGCATACTGTCATTCACATAGAGTTCTTCATCGAGACTTAAAACCACAGAATTTGTTGA
TAGATCGCAGCACTAATGCACTGAAACTTGCAGATTTTGGATTGGCCAGGGCTTTTGGAATT
CCTGTTAGGACATTTACACATGAGGTGGTAACACTGTGGTACAGAGCTCCGGAAATTTTGCT
TGGATCCCGTCAGTATTCTACCCCAGTTGATATTTGGTCAGTGGGATGCATATTTGCAGAGA
TGGTAAATCAACGACCACTTTTCCCTGGGGACTCTGAGATTGATGAATTGTTTAAAATATTC
AGAATCATGGGTACACCAAATGAAGATACATGGCCTGGAGTGACATCATTGCCAGATTTTAA
ATCAGCCTTTCCCAAATGGCAACCTAAGGACCTGAAAAATGTGGTTCCAAATCTTGAGCCAG
CTGGTCTTGATCTTCTTTCTAGCATGCTTTACTTGGATCCCAGCAAAAGAATTACTGCTAGG
AGCGCTCTTGAGCATGAATACTTCAAAGACATTAAATTTGTACCCTGATTTCTTATCTTCAA
GGCTGAGGTGTCTTATTAGTATGTGTAGCATTTATGGGTTTTGACTCAAACGCGTGTTGTCC
TTGCTTTTTTCTTCAATGCTTTTGGACCGAATCATATTTCATTTATTTGTTCTTACATTTTT
ATTTAGTATGTGTGATCTTGTTACCTATTTACCCGTTT

SEQ ID NO: 24 Glycine max cv Prize protein kinase, deduced
protein sequence
MEQYEKVEKIGEGTYGVVYKGRDRVTNETIALKKIRLEQEDEGVPSTAIREISLLKEMQH
RNIVRLQDVVHDEKSLYLVFEYLDLDLKKHMDSSPEFAKDPRQVKMFLYQILCGIAYCHS
HRVLHRDLKPQNLLIDRSTNALKLADFGLARAFGIPVRTFTHEVVTLWYRAPEILLGSRQ
YSTPVDIWSVGCIFAEMVNQRPLFPGDSEIDELFKIFRIMGTPNEDTWPGVTSLPDFKSA
FPKWQPKDLKNVVPNLEPAGLDLLSSMLYLDPSKRITARSALEHEYFKDIKFVP

FIGURE 3 (continued)

SEQ ID NO: 25 Glycine max cv Prize protein kinase mRNA (M93139)
AATTCGGCACGAGGTGGAGTGAGAGATAGTGACTGCAAAACCGCTCCAGCCTTGTTTCTTCT
CAGATCTTCTTCCATGGAACAGTACGAGAAGGTGGAGAAGATAGGCGAGGGAACATACGGCG
TCGTTTACAAGGCTCGCGACCGCGTCACCAATGAGACCATCGCTCTCAAGAAGATTCGCCTC
GAGCAGGAGGACGAAGGCGTTCCCAGCACCGCCATTCGCGAGATTTCTCTCCTCAAAGAGAT
GCAGCATAGGAACATTGTTAGGTTGCAGGATGTAGTACACAGTGAAGCGATTGTATCTGG
TTTTTGAGTATCTGGACTTGGATCTAAAGAAACATATGGATTCATCTCCAGAGTTTGTGAAA
GATCCACGGCAAGTAAAGATGTTCCTTTATCAAATTCTCTGTGGCATTGCTTACTGTCATTC
ACATAGAGTTCTTCATCGAGACTTGAAACCACAGAATTTGTTGATAGATCGCCGTACTAATT
CACTAAAGCTTGCAGATTTTGGATTGGCTAGGGCATTTGGCATTCCTGTCAGGACATTTACA
CATGAGGTGGTGACATTATGGTACAGAGCTCCAGAAATATTGCTTGGATCTCGTCATTATTC
TACGCCAGTTGATGTTTGGTCAGTGGGATGTATATTTGCAGAGATGGTAAACCGACGACCTC
TATTCCCTGGGGACTCTGAGATTGATGAATTATTTAAAATATTCAGAATCTTGGGTACCCCA
AATGAAGACACATGGCCTGGTGTAACTTCATTGCCTGATTTTAAATCAACATTTCCCAAATG
GCCATCCAAGGACTTGGCAAATGTGGTTCCAAATCTTGATGCAGCTGGTCTTAATCTTCTTT
CTAGTATGCTTTGCTTGGATCCCAGCAAAAGAATCACCGCCAGGAGCGCTGTGGAGCATGAA
TACTTCAAAGACATTAAATTTGTTCCCTGATTCCATATCTTGATGGCAAACGTGTTTATAGT
AATATTGTGCAGAATTTATGGGTTTTGACTCTGCGAGAAATGCGTGCTGTCTTTTTCTATTT
TCTTAGTGACTTGGGAGTGTGAGCCATATTTCCATTTTTGGTCCTTACAGAATGTTTCAGA
TTCAACTTGAGTGTGATTATATTGCATATTACTTTTTCATT

SEQ ID NO: 26 Glycine max cv Prize protein kinase, deduced protein sequence
MEQYEKVEKIGEGTYGVVYKARDRVTNETIALKKIRLEQEDEGVPSTAIREISLLKEMQH
RNIVRLQDVVHSEKRLYLVFEYLDLDLKKHMDSSPEFVKDPRQVKMFLYQILCGIAYCHS
HRVLHRDLKPQNLLIDRRTNSLKLADFGLARAFGIPVRTFTHEVVTLWYRAPEILLGSRH
YSTPVDVWSVGCIFAEMVNRRPLFPGDSEIDELFKIFRILGTPNEDTWPGVTSLPDFKST
FPKWPSKDLANVVPNLDAAGLNLLSSMLCLDPSKRITARSAVEHEYFKDIKFVP

SEQ ID NO: 27 Lycopersicon esculentum mRNA for cyclin-dependent protein kinase (cdc2A-1) (Y17225)
TTGACTGTAGTCCAAACATTTTGGTAACACCGTAGAAGTACGCCGACACTTGCCTGTCGCCT
CCTCCCCGCTTCACGAACGGCGATTTCGTCCTCTTTTCCCGACCAAAGGGAGTCCATTGAGT
TTGAAATAGATGGACCAGTATGAAAAAGTTGAGAAGATTGGGGAAGGAACATATGGTGTAGT
GTACAAGGCTCGTGATCGTGTAACTAATGAAACTATTGCACTGAAGAAAATAAGGTTGGAGC
AGGAAGACGAGGGGGTACCAAGCACAGCTATTAGAGAAATATCTCTCTTGAAAGAGATGCAA
CATGCTAATATTGTGAGGTTGCAGGATGTGGTGCACAGTGAAAAGCGATTGTATCTAGTGTT
TGAATATCTTGACTTGGACTTGAAGAAGCACATGGATTCGTGTCCTGAATTCTCTAAGGATC
CACGTCTGGTTAAAATGTTCTTGTATCAAATACTCCGTGGTATTGCTTATTGTCATTCTCAT
AGAGTTCTTCATAGAGATTTGAAGCCTCAGAACTTACTAATAGATCGACGTACAAATGCTTT
AAAGCTGGCAGACTTTGGTTTGGCTAGAGCATTTGGTATTCCTGTCAGAACTTTCACTCATG
AGGTGGTGACATTGTGGTACAGGGCACCAGAAATACTGCTTGGATCACGCCATTACTCTACT
CCTGTTGATGTGTGGTCAGTTGGTTGCATATTTGCTGAGATGGTGAATCAGCCGCCTCTGTT
TCCTGGTGACTCTGAGATTGATGAACTTTTCAAGATTTTCAGAGTATTGGGTACTCCAAATG

```
AGGATACATGGCCTGGAGTGACTTCTCTGCCTGATTACAAATCTGCCTTCCCAAAATGGCCT
CCTAAGGACCTGGCAATTATTGTACCAAATGTTGATGGAGCAGGCCTTGATCTTCTTGGTAA
AATGCTCTCCTTGGATCCCAGTAAGAGAATCACCGCGAGGAATGCCCTTGAGCATGAGTACT
TCAAGGATATTGGGTATGTGCCGTGATTGTCTGCCCCTTCATCCAGAATGCTATTGTAAATT
TGGTATGTCATCTACAGGTTTTGTTCTGGAGAATCTGTGTGATCTTTAGGCCTTTTTGGCCC
CTCAAAGTTTTATTCCATTGTGTATCCTGTTCCAGCACATGTGGTCACAATTCGTGTCCACA
TGTTGTAGTATACTTTCCCGTGTAATATCCATTTGGTTCTATTCAGGGGTTCAGTATCCTTG
TACAACGAATGCTTATTTAGATACAACAATGGATACTGTAATGTTAAATAGATTGGATTTGG
TGTGTCAATTAGAAGTTTTGCATAGTTTTGCCTGGAGTGGAACAAAGCTTGAGATGATTGTC
CGACTCCTAGGTTATGCCAGTGCATTTCTTGATGACGCAGGCTGGTTATATCAAGTTCTATT
TTGATGTTAAAAAAAAAAAAAAAAAAAAAAA
```

SEQ ID NO: 28 cyclin-dependent protein kinase p34cdc2 [Lycopersicon esculentum] (CAA76700)

```
MDQYEKVEKIGEGTYGVVYKARDRVTNETIALKKIRLEQEDEGVPSTAIREISLLKEMQHAN
IVRLQDVVHSEKRLYLVFEYLDLDLKKHMDSCPEFSKDPRLVKMFLYQILRGIAYCHSHRVL
HRDLKPQNLLIDRRTNALKLADFGLARAFGIPVRTFTHEVVTLWYRAPEILLGSRHYSTPVD
VWSVGCIFAEMVNQPPLFPGDSEIDELFKIFRVLGTPNEDTWPGVTSLPDYKSAFPKWPPKD
LAIIVPNVDGAGLDLLGKMLSLDPSKRITARNALEHEYFKDIGYVP
```

SEQ ID NO: 29 Lycopersicon esculentum mRNA for cyclin-dependent protein kinase (cdc2A-2) (Y17226)

```
TCCGTCTTCCGCCAGTACCGCCGGCAGCTTTTCATCTCCGATCCTCCGGTTCACGAACGGCG
ATATCCTTCTCTAGACATACTCAAGAGTCCATCCAGTTTGACCTAATGCATGGACCAGTATG
AAAAAGTTGAAAAGATTGGTGAAGGAACGTACGGCGTAGTGTACAAAGCTCGTGATCGTGTA
ACTAATGAAACTATTGCACTGAAGAAAATTCGGCTGGAGCAGGAAGACGAGGGTGTGCCAAG
CACGGCTATTAGAGAAATCTCCCTCTTGAAAGAGATGCAGCATGGAAACATTGTGAGGTTGC
AAGATGTGGTTCACAGTGAGAAGCGATTATATCTAGTGTTTGAATATCTCGACTTGGATTTG
AAGAAGCATATGGACTCATGTCCTGAGTTCTCTAAGGATCCGCGTCTGGTAAAATGTTTTT
GTATCAAATTCTCCGTGGAATTGCTTATTGTCATTCTCATAGAGTTCTTCACCGAGACTTGA
AGCCTCAGAACTTGCTGATAGATAGACGTACAAACGTTCTAAAGCTTGCAGACTTTGGATTG
GCTAGAGCATTCGGCATTCCTGTCAGAACTTTCACCCACGAGGTGGTGACGTTATGGTACAG
GGCACCAGAAATACTGCTAGGATCACGCCACTACTCTACTCCTGTTGATGTTTGGTCAGTAG
GCTGCATATTTGCTGAGATGGTGAACCAGCGGCCTCTGTTTCCTGGTGACTCCGAGATTGAC
GAACTTTTCAAGATTTTCAGAGTTGTCGGTACTCCAAATGAGGATACATGGCCTGGAGTGAC
TTCTTTGCCTGATTTTAAATCTGCTTTTCCAAAGTGGCCATCTAAGGACTTAGGAACTGTAG
TACCTAATCTTGGTGCAGCAGGCCTTGATCTCATTGGTAAATGCTTACCTTAGACCCCAGC
AAGAGAATCACTGCCCGAAGCGCCCTTGAGCATGAGTACTTCAAGGACATTGGGTTCGTACC
ATGAATCGAGGCACCTGCATCTTCAGTTCTAATGTATATTTGAGTGTGTTATTTTTAGGCTT
TATTTGTCCTCTACTTTTAATTATATTTCCTCCAATGACATCCAATCTGTTTACGATTCACG
CTAGATGTTTGAAGATAGTTTCACTGCAAAAAAAAAAAAAAAAAAAAAAAAAAAAAAAAAAA
```

SEQ ID NO: 30 cyclin-dependent protein kinase p34cdc2 [Lycopersicon esculentum] (CAA76701)
MDQYEKVEKIGEGTYGVVYKARDRVTNETIALKKIRLEQEDEGVPSTAIREISLLKEMQHGN
IVRLQDVVHSEKRLYLVFEYLDLDLKKHMDSCPEFSKDPRLVKMFLYQILRGIAYCHSHRVL
HRDLKPQNLLIDRRTNVLKLADFGLARAFGIPVRTFTHEVVTLWYRAPEILLGSRHYSTPVD
VWSVGCIFAEMVNQRPLFPGDSEIDELFKIFRVVGTPNEDTWPGVTSLPDFKSAFPKWPSKD
LGTVVPNLGAAGLDLIGKMLTLDPSKRITARSALEHEYFKDIGFVP

SEQ ID NO: 31 Medicago sativa CDC2MS serine/threonine protein kinase (CDC2MS) mRNA, partial cds (M58365)
GGGCGAAAATGTGGAGAAGATTGGTGAAGGAACATACGGCGTCGTTTACAAGGCACGTGACC
GTGTAACGAATGAAACCATCGCGTTGAAGAAGATTCGACTTGAACAGGAAGATGAAGGTGTT
CCTAGCACTGCCATTCGTGAGATTTCGCTGCTTAAAGAAATGCAGCATAGGAACATCGTTAG
GTTGCAGGATGTAGTGCACAGTGACAAGCGATTGTATCTGGTTTTTGAGTATCTGGACTTAG
ATCTGAAGAAGCATATGGATTCATCTCCTGAGTTTATAAAAGATCCGCGACAAGTAAAAATG
TTCCTTTATCAAATGCTCTGTGGAATTGCTTACTGTCATTCACACAGAGTTCTTCATCGAGA
CTTGAAACCACAGAATTTGTTGATAGATCGCCGTACTAATTCACTTAAGCTTGCCGATTTTG
GATTGGCCAGGGCATTTGGTATTCCTGTCAGAACATTTACACATGAGGTAGTTACACTGTGG
TACCGAGCTCCGGAAATATTGCTTGGATCTCGTCATTATTCTACCCCAGTTGATGTTTGGTC
AGTGGGATGTATATTTGCAGAGATGGCAAATCGGCGACCTCTATCCCTGGGGATTCCGAGA
TTGATGAGTTATTTAAAATATTCAGAATCTTGGGTACACCAAATGAAGATACATGGCCAGGA
GTAACTTCATTGCCTGATTTTAAATCAACATTTCCCAGGTGGCCATCTAAGGACCTAGCAAC
CGTGGTTCCAAATCTTGAGCCAGCTGGTCTTGATCTTCTTAATAGCATGCTTTGCTTGGATC
CCACCAAAAGAATTACTGCCAGGAGCGCTGTGGAGCATGAATATTTCAAAGACATTAAGTTT
GTACCCTAATTCTATAATCTATATCTTAATGGTAAAGGTGTTTATAGCAATATGTGCAGAAT
TTATGGATTTTGATTGTGCCAGAAATGGGTGTGTTATTTTTGCTACTTTCTTCAAAGACCTA
GGATCC

SEQ ID NO: 32 serine threonine tyrosine kinase, partial sequence [Medicago sativa]( AAB41817)
GENVEKIGEGTYGVVYKARDRVTNETIALKKIRLEQEDEGVPSTAIREISLLKEMQHRNIVR
LQDVVHSDKRLYLVFEYLDLDLKKHMDSSPEFIKDPRQVKMFLYQMLCGIAYCHSHRVLHRD
LKPQNLLIDRRTNSLKLADFGLARAFGIPVRTFTHEVVTLWYRAPEILLGSRHYSTPVDVWS
VGCIFAEMANRRPLSPGDSEIDELFKIFRILGTPNEDTWPGVTSLPDFKSTFPRWPSKDLAT
VVPNLEPAGLDLLNSMLCLDPTKRITARSAVEHEYFKDIKFVP

SEQ ID NO: 33 M.sativa mRNA for CDC2 kinase (X70707)
CACGGCGCGCTGTCTGTGTAACCGTTTCTCTGAATTTCAACATCGCTTTGAACTTTAAGCGT
TTTTTTGATGGAACAGTACGAGAAAGTTGAGAAGATAGGAGAAGGTACTTACGGTGTGGTTT
ACAAGGCTCGTGACCGTGCTACCAATGAGACGATAGCTTTGAAGAAGATTCGTCTTGAGCAG
GAAGATGAGGGAGTTCCGAGTACCGCTATTCGAGAGATTTCTCTCTTGAAGGAAATGCAGCA
CAGGAACATTGTTAGGTTGCAGGATGTGGTGCACAGTGAGAAGCGATTGTATCTGGTTTTTG
AGTACCTTGACTTGGATCTAAAGAAGTTTATGGATTCATCTCCAGAATTTGCAAAAGATCAA
CGGCAAATAAAGATGTTCCTTTATCAAATTCTCTGTGGCATTGCTTACTGTCATTCTCATAG
AGTTCTTCATAGAGACTTGAAACCACAGAATCTGCTGATTGATCGCAGCTCTAATGCCGTAA

FIGURE 3 (continued)

AGCTTGCAGATTTTGGATTGGCCAGGGCATTTGGAATTCCTGTCAGGACATTTACACATGAG
GTGGTGACACTCTGGTACAGAGCTCCAGAAATATTGCTTGGGTCTCGTCATTATTCTACCCC
GGTTGATGTCTGGTCAGTGGGATGCATATTTGCAGAGATGATAAACCAACGGCCACTTTTCC
CAGGGGACTCTGAGATTGATGAATTGTTTAAAATATTCAGAATCACGGGTACACCGAATGAG
GAAACATGGCCTGGAGTGACTTCATTGCCTGATTTTAAATCAGCCTTTCCCAAGTGGCCAGC
TAAGGACCTGGCAACTCAAGTCCCAAATCTGGAGCCAGCTGGTCTTGATCTTCTATCCAGTA
CTTGTCGCTTGGATCCCACCAGAAGAATTACTGCCAGGGGAGCTCTTGAGCATGAATACTTC
AAAGACATTAAGTTTGTCCCATGAGTTCTTGGCTTCACGGAAGAGGTGTCTATATTATTGTG
TGTATCATTTATGGGTTTTGACTCAGAAATGGGTGCTATCCTTGGTATTTTCTTCAATGCTT
GGACTGAGTAATATTTAATTTATTGGTTCTTGGATTTTTTTAGATTCAGCTTGAGTGTGAT
CATACTGCCTATTACCTTTTTAATGTCTTAGTCTCAGTACAATGCAACCAGCAAATTTCCT
GTTTGATTGATGTATAATATTAATAGACATTGTTGAATGGTGGTTGTAGAACAAATGTTACT
CCTACTGGCATGGAGCATGTAAATTTGACATCCGTTCATGTCTATAAGTTGGTTTTAAAAAA
AAAAAA

SEQ ID NO: 34 CDC2 kinase [Medicago sativa] (CAA50038)
MEQYEKVEKIGEGTYGVVYKARDRATNETIALKKIRLEQEDEGVPSTAIREISLLKEMQHRN
IVRLQDVVHSEKRLYLVFEYLDLDLKKFMDSSPEFAKDQRQIKMFLYQILCGIAYCHSHRVL
HRDLKPQNLLIDRSSNAVKLADFGLARAFGIPVRTFTHEVVTLWYRAPEILLGSRHYSTPVD
VWSVGCIFAEMINQRPLFPGDSEIDELFKIFRITGTPNEETWPGVTSLPDFKSAFPKWPAKD
LATQVPNLEPAGLDLLSSTCRLDPTRRITARGALEHEYFKDIKFVP

SEQ ID NO: 35 Nicotiana tabacum cdc2 mRNA, complete cds (L77082)
CACGAGCCTCTATGCAAATAGAAGCAAAAGAAGAGTATTGACTGTAGTCCAAACATTTTGGT
ACGAGTACGCCGACACTTGCCTGTCGCCTCCTCCTCCGCTTCACGAACCGCGATTTAGTCCT
CTTTTTTCGATCAAAGGGAGTTCATTGAGTTTGACTAGATGGACCAGTATGAAAAAGTTGAG
AAGATTGGGGAAGGAACATACGGTGTAGTGTACAAGGCTCGTGATCGTGTAACTAATGAAAC
AATTGCGCTGAAGAAAATAAGGCTGGAGCAGGAAGATGAGGGAGTACCAAGCACAGCTATTA
GAGAAATCTCTCTTTTGAAAGAGATGCAGCATGCTAATATTGTGAGGTTGCAGGATGTTGTG
CACAGTGAAAAGCGATTGTATCTAGTTTTTGAATATCTTGACTTGGACTTGAAGAAGCACAT
GGATTCATCTCCTGAATTCTCTAAGGATCCACGTCTGGTTAAAATGTTTTTGTATCAAATAC
TCCGTGGTATTGCTTATTGTCATTCTCATAGAGTTCTTCATCGAGATTTGAAGCCTCAAAAC
TTGCTGATAGATCGACGTACAAATGCTTTAAAGCTTGCAGACTTTGGATTGGCTAGAGCATT
TGGTATTCCTGTCAGAACTTTCACTCATGAGGTGGTGACATTGTGGTACAGGGCACCAGAAA
TACTGCTGGGTACACGCCATTATTCTACTCCTGTTGATGTGTGGTCAGTTGGTTGCATATTT
GCTGAGATGGTGACTCAGCGCCCTCTGTTTCCTGGTGACTCCGAGATTGATGAACTTTTCAA
GATTTTCAGAGTGATGGGTACTCCAAATGAGGATACATGGCCTGGAGTGACTACTCTGCCTG
ATTTTAAATCTGCCTTCCCAAAATGGCCTTCTAAGGACCTGGCAACTATTGTCCCAAATCTT
GATGGAGCAGGCCTTGATCTTCTTGATAAACTTCGCGCTTGGATCCCAGCAAGAGAATCAC
TGCCAGGAATGCCCTTGAGCATGAGTACTTCAAGGATATTGGGTATGTTCCGTGAGTCTTTG
CACCTTCATCCAGAATGCTACTGTAAATTTGGTATGTCATCTACAGGTTTTGTTCTGGAGGA
TTTATGTGATTTTTAGAGGCCCCACCCCACCCCTCAAGTTGTTATTCTTCCAATGTGATTCA
ATCTATATTAAAGTGGTCTTGCACAGCCCTCATGGATATTTGTTGTTCCAGCATTTGTGGTC
ACAATTCGTGTCCGCATGTTGAACCATACTTTCCAGTGTAATATCATTTTGTTATAGTTCCG
GGTGCGGTATACCTGTCCAATCATACTTGTTCAGCACTGGATTCTGTAATGTTAAATAGATT
GGTTTTGGTGTGTCA

FIGURE 3 (continued)

SEQ ID NO: 36 Nicotiana tabacum cdc2 gene product (AAB02567)
MDQYEKVEKIGEGTYGVVYKARDRVTNETIALKKIRLEQEDEGVPSTAIREISLLKEMQHAN
IVRLQDVVHSEKRLYLVFEYLDLDLKKHMDSSPEFSKDPRLVKMFLYQILRGIAYCHSHRVL
HRDLKPQNLLIDRRTNALKLADFGLARAFGIPVRTFTHEVVTLWYRAPEILLGTRHYSTPVD
VWSVGCIFAEMVTQRPLFPGDSEIDELFKIFRVMGTPNEDTWPGVTTLPDFKSAFPKWPSKD
LATIVPNLDGAGLDLLDKTSRLDPSKRITARNALEHEYFKDIGYVP

SEQ ID NO: 37 Nicotiana tabacum cdc2 mRNA, complete cds (L77083)
AATTCGGCACGAGTTTTGGTACAAGTACGCCGACACTTGCCCGTCGCCTCCTCCTCCGCTTC
AAGACGGCGATTTCGTCCTCTTTATCCGACCAAAGGGAGTTCATTGAGTTTGACCTAGATGG
ACCAGTATGAAAAAGTTGAGAAGATTGGGGAAGGAACATACGGTGTAGTGTACAAGGCTCGT
GATCGTGTAACTAATGAAACAATTGCGCTGAAGAAAATAAGGCTGGAGCAGGAAGATGAGGG
AGTACCAAGCACAGCTATTAGAGAAATCTCTCTCTTGAAAGAGATGCAGCATGCTAATATTG
TGAGGTTGCAGGATGTAGTGCACAGTGAGAAGCGATTATATCTAGTCTTTGAATATCTTGAC
TTGGACTTGAAGAACACATGGATTACTACTCCTGAATTCTCTGAGGATCCACGTCTGGTTAA
AATGTTTTTGTATCAAATACTCCGTGGTATTGCCTATTGTCATTCTCATAGAGTTCTTCATC
GAGATTTGAAGCCTCAAAACTTGCTGATAGATCGACGTACAAATGCTTTAAAGCTTGCAGAC
TTTGGATTGGCTAGAGCATTTGGTATTCCTGTCAGAACTTTCACTCATGAGGTGGTGACATT
GTGGTACAGGGCACCAGAAATACTGCTGGGATCGCGCCATTACTCTACTCCTGTTGATGTGT
GGTCAGTTGGTTGCATATTTGCTGAGATGGTGACTCAGCGCCCTCTGTTTCCTGGTGATTCC
GAGATTGATGAACTTTCAAGATTCAGAGTGATGGGTACTCCAAATGAGGATACATGGCCTGG
AGTGACAACTCTGCCTGATTTTAAATCTGCCTTCCCAAAATGGCCTTCTAAGGACCTGGCAA
CTATTGTCCCAAATCTTGATGGAGCAGGCCTTGATCTTCTTGATAAAATCGTCCGCTTGGAT
CCCAGCAAGAGAATCACTGCCAGGAATGCCCTTGAGCATGAGTACTTCAAGGATATTGGGTA
TGTTCCGTGAGTCTTTGCACCTTCATCCAGAATGCTACTGTAAATTTGGTATGTCATCTACA
AGGTTTTGTTCTGGAGGATTTGTGTTATTTTAGGGCCACCCCACCCATCCCCTCAAGTGCC
CCACCCCATCCCCTCAAGTTGTTATTCTTCCAATGTGATTCAATATATATTAAAGTGGTCTT
GCACAGCCCTCATGGATATTTGTTGTTCCAGCATCTGTGGTCACAATTCGTGTCCACATGTT
GAACCATACTTTCCAGTGTAATATTTGTTTGTTATAGTTTGGGGTGCGGTACACTTATCCAA
TCATACTTGTTTAGCACTGGATACTGTAATGTTAATTAGATTGGTTTTGGTGTGTCA

SEQ ID NO: 38 Nicotiana tabacum cdc2 gene product (AAB02568)
MDQYEKVEKIGEGTYGVVYKARDRVTNETIALKKIRLEQEDEGVPSTAIREISLLKEMQHAN
IVRLQDVVHSEKRLYLVFEYLDLDLKNTWITTPEFSEDPRLVKMFLYQILRGIAYCHSHRVL
HRDLKPQNLLIDRRTNALKLADFGLARAFGIPVRTFTHEVVTLWYRAPEILLGSRHYSTPVD
VWSVGCIFAEMVTQRPLFPGDSEIDELSRFRVMGTPNEDTWPGVTTLPDFKSAFPKWPSKDL
ATIVPNLDGAGLDLLDKIVRLDPSKRITARNALEHEYFKDIGYVP

SEQ ID NO: 39 Nicotiana tabacum mRNA for cdc2 homolog, complete cds (D50738)
GCGGCCGCGGATCCAAAGAAGAGTATTGACTGTAGTCCAAACATTTTGGTACAAGTACGCCG
ACACTTGCCCGTCGCCTCCTCCTCCGCTTCAAGACGGCGATTTCGTCCTCTTTATCCGACCA
AAGGGAGTTCATTGAGTTTGACCTAGATGGACCAGTATGAAAAAGTTGAGAAGATTGGGGAA
GGAACATACGGTGTAGTGTACAAGGCTCGTGATCGTGTAACTAATGAAACAATTGCGCTGAA

FIGURE 3 (continued)

```
GAAAATAAGGCTGGAGCAGGAAGATGAGGGAGTACCAAGCACAGCTATTAGAGAAATCTCTC
TCTTGAAAGAGATGCAGCATGCTAATATTGTGAGGTTGCAGGATGTAGTGCACAGTGAGAAG
CGATTATATCTAGTCTTTGAATATCTTGACTTGGACTTGAAGAAGCACATGGATTCATCTCC
TGAATTCTCTGAGGATCCACGTCTGGTTAAAATGTTTTGTATCAAATACTCCGTGGTATTG
CCTATTGTCATTCTCATAGAGTTCTTCATCGAGATTTGAAGCCTCAAAACTTGCTGATAGAT
CGACGTACAAATGCTTTAAAGCTTGCAGACTTTGGATTGGCTAGAGCATTTGGTATTCCTGT
CAGAACTTTCACTCATGAGGTGGTGACATTGTGGTACAGGGCACCAGAAATACTGCTGGGAT
CGCGCCATTACTCTACTCCTGTTGATGTGTGGTCAGTTGGTTGCATATTTGCTGAGATGGTG
ACTCAGCGCCCTCTGTTTCCTGGTGATTCCAGATTGATGAACTTTTCAAGATTTTCAGAGT
GATGGGTACTCCAAATGAGGATACATGGCCTGGAGTGACAACTCTGCCTGATTTTAAATCTG
CCTTCCCAAAATGGCCTTCTAAGGACCTGGCAACTATTGTCCCAAATCTTGATGGAGCAGGC
CTTGATCTTCTTGATAAAATGCTCCGGTTGGATCCCAGCAAGAGAATCACTGCCAGGAATGC
CCTTGAGCATGAGTACTTCAAGGATATTGGGTATGTTCCGTGAGTCTTTGCACCTTCATCCA
GAATGCTACTGTAAATTTGGTATGTCATCTACAAGGTTTTGTTCTGGAGGATTTGTGTTATT
TTTAGGGCCACCCCCCACCCCCATCCCCCTCAAGTTGTTATTCTTCCAATGTGATTCAATAT
ATATTAAAGTGGTCTTGGCACAGCCCTCATGGATATTGTTGTTCCAGCATCTGTGGTCACA
ATTCGTGTCCACATGTTGAACCATACTTTCCAGTGTAATATTTGTTTCTTATAGTTTGGGGT
GCGGTACACTTGTCCAATCATACTTGTTTAGCACTGGATACTGTAATGTTAATTAGATTGGT
TTTGGTGTGTCATTAGAAGTTTTGCATAGTTTTT
```

SEQ ID NO: 40 cdc2 homolog [Nicotiana tabacum] (BAA09369)
MDQYEKVEKIGEGTYGVVYKARDRVTNETIALKKIRLEQEDEGVPSTAIREISLLKEMQHAN
IVRLQDVVHSEKRLYLVFEYLDLDLKKHMDSSPEFSEDPRLVKMFLYQILRGIAYCHSHRVL
HRDLKPQNLLIDRRTNALKLADFGLARAFGIPVRTFTHEVVTLWYRAPEILLGSRHYSTPVD
VWSVGCIFAEMVTQRPLFPGDSEIDELFKIFRVMGTPNEDTWPGVTTLPDFKSAFPKWPSKD
LATIVPNLDGAGLDLLDKMLRLDPSKRITARNALEHEYFKDIGYVP

SEQ ID NO: 41 O.sativa Rcdc2-2 gene for p34-cdc2 protein kinase (X60375)
```
CCCACGCCGCCGCCGCCCGGATCGCCGCGAGATGGAGCAGTACGAGAAGGTGGAGAAGA
TCGGGGAGGGGACGTACGGGGTGGTGTACAAGGGCAAGCACCGGCATACCAACGAGACGATC
GCGCTCAAGAAGATCCGCCTGGAGCAGGAGGACGAGGGCGTCCCCTCCACCGCCATCCGCGA
GATCTCGCTGCTCAAGGAGATGCAGCATCGCAACATCGTCAGGCTGCAGGACGTCGTGCACA
AGGAGAAATGCATATACCTCGTCTTCGAGTACCTCGACCTTGACCTCAAGAAGCACATGGAC
TCATCCCCGGATTTCAAGAACCACCGCATAGTCAAATCGTTCCTCTACCAGATTCTCCGGGG
CATTGCGTACTGCCACTCGCACCGTGTTCTCCACCGAGATTTGAAGCCCCAGAACCTGCTGA
TAGATCGGCGTACCAACTCATTGAAGCTCGCGGACTTTGGGTTGGCCAGGGCATTTGGCATT
CCTGTCCGGACATTTACTCACGAGGTGGTGACATTGTGGTATAGAGCACCTGAAATTCTTCT
TGGTGCAAGGCATTATTCCACCCCTGTTGACATGTGGTCAGTTGGTTGCATTTTGCTGAAA
TGGTGAATCAGAAGCCACTATTTCCTGGAGATTCTGAGATTGATGAACTCTTTAAGATTTTC
AGTATTATGGGCACTCCAAATGAAGAAACTTGGCCAGGTGTTGCTTCACTACCTGACTACAT
ATCAACTTTCCCAAAGTGGCCATCTGTGGATCTTGCAACCGTGGTCCCAACACTTGATTCTT
CAGGACTCGATCTTCTCTCTAAAATGCTCCGTTTAGATCCAAGCAAAAGAATCAATGCCCGT
GCTGCCCTCGAGCACGAGTACTTCAAGGACCTGGAAGTGGCGTAGATTATGCCTCATCTTGT
```

FIGURE 3 (continued)

```
CCATTTGTAAATTAAGATTGCATTGTTTGCTCAGCCGAGTTCTTTTTTGGCTTTCCTTAATC
TAAGTTGGTGTGCTCCTCCCCCAACTCTATTTTTGCCCTTTTGGTTGTGTAGAGATGAGAAC
AGAAGGTACCTCCTGGCTATCCCTCTGTGTAATTCAAGCCAATTGAAAGATCCTTATTGCGG
GAGCTCTAAA
```

SEQ ID NO: 42 Rcdc2-2 [Oryza sativa (japonica cultivar-group)] (CAA42923)
```
MEQYEKVEKIGEGTYGVVYKGKHRHTNETIALKKIRLEQEDEGVPSTAIREISLLKEMQHRN
IVRLQDVVHKEKCIYLVFEYLDLDLKKHMDSSPDFKNHRIVKSFLYQILRGIAYCHSHRVLH
RDLKPQNLLIDRRTNSLKLADFGLARAFGIPVRTFTHEVVTLWYRAPEILLGARHYSTPVDM
WSVGCIFAEMVNQKPLFPGDSEIDELFKIFSIMGTPNEETWPGVASLPDYISTFPKWPSVDL
ATVVPTLDSSGLDLLSKMLRLDPSKRINARAALEHEYFKDLEVA
```

SEQ ID NO: 43 Petroselinum crispum protein kinase p34cdc2 (cdc2) mRNA, complete cds (L34206)
```
AGAGAACTCCTTTTCTACATAAAATCTCCCCCCTTCCTCTGAAGATTTCCCCTTGCCAACGC
TCTAAAATATCTTTGCGACTTATCTGTTAGGTGAAATCAAATGGACCAGTATGAAAAGGTTG
AGAAGATTGGTGAAGGAACATATGGAGTAGTTTATAAGGCTCGTGACCGCGTCACAAATGAA
ACCATCGCTTTAAAGAAGATTCGGCTAGAGCAAGAAGATGAAGGAGTGCCAAGCACTGCTAT
TAGAGAAATTTCTTTACTGAAGGAAATGCAGCATGGAAATATTGTCAGGTTACAAGATGTTG
TGCACAGCGAGAAACGGTTGTATCTGGTTTTTGAATATCTGGACCTAGATTTGAAGAAACAT
ATGGATTCATGTCCAGAGTTTGCCAAGGATCCACGTCTGATAAAGATGTTTCTGTATCAAAT
ACTTCGTGGGATTGCTTATTGTCATTCCCATAGAGTTCTGCATCGGGATCTCAAACCCCAAA
ACCTGCTCATAGATCGACGTACCAATGCTCTAAAGCTTGCAGATTTTGGACTTGCCAGGGCA
TTTGGAATTCCTGTCAGAACATTTACACACGAGGTTGTGACACTTTGGTACAGGGCACCAGA
GATACTCCTTGGATCCCGCCACTATTCCACACCTGTTGATGTGTGGTCTGTCGGTTGTATTT
TTGCTGAGATGGTGAACCAGCGGCCATTGTTTCCGGGGATTCTGAGATTGATGAATTATTT
AAAATATTCAGAATTACGGGTACCCCGAATGAGGATACCTGGCCTGGAGTTACATCTCTCCC
TGATTTTAAGTCTGCCTTTCCAAAATGGCCATCTAAGGAACTGGAAACTGTGGTCCCAAATC
TTGATTCGGCCGGTCTGAATCTCCTCAAAAAAATGCTTTGCTTGGATCCGAGCAGAAGAATT
ACAGCCAGGATTGCACTTGAGCATGAATACTTCAAGGATATTGGATTGTTCCTTAAGTCTT
ATCTTTCCGGCCGCATTTGTATATGATATTAGAGTTTCTTGGGTTTGATTTTGTAAGAAAAG
TGTGCTAGTTTTTTTTATCGTTCTATAGTTATTTAATTTCCTTTTCCTTGGATGCGATTCTT
ATTGTTTCCAAGCTGGCTGTAGAGCAATCATATATCATCTCGTCCCTGCTCTCTGGGCTTAA
TGTTCAATGATACATGTATTGTCACATGTTTTTTTTGTAATTCTTTGTACTGTCACTAGGC
ATACATTGGATAATCTCTTACTTAATGAATTTGTTTGGTGTGCTTTGT
```

SEQ ID NO: 44 Petroselinum crispum protein kinase p34cdc2 (AAC41680)
```
MDQYEKVEKIGEGTYGVVYKARDRVTNETIALKKIRLEQEDEGVPSTAIREISLLKEMQHGN
IVRLQDVVHSEKRLYLVFEYLDLDLKKHMDSCPEFAKDPRLIKMFLYQILRGIAYCHSHRVL
HRDLKPQNLLIDRRTNALKLADFGLARAFGIPVRTFTHEVVTLWYRAPEILLGSRHYSTPVD
VWSVGCIFAEMVNQRPLFPGDSEIDELFKIFRITGTPNEDTWPGVTSLPDFKSAFPKWPSKE
LETVVPNLDSAGLNLLKKMLCLDPSRRITARIALEHEYFKDIGIVP
```

FIGURE 3 (continued)

SEQ ID NO: 45 Petunia hybrida mRNA for cyclin dependent kinase, partial sequence (Y13646)
ATGGACCAGTATGAAAAAGTTGAGAAGATTGGGGAAGGAACATACGGTGTAGTGTACAAGGC
TCGTGATCGTGTAACTAATGAAACAATTGCGCTGAAGAAAATAAGGCTGGAGCAGGAAGATG
AGGGAGTACCAAGCACAGCTATTAGAGAAATCTCTCTTTTGAAAGAGATGCAGCATGCTAAT
ATTGTGAGGTTGCAGGATGTTGTGCACACAGTGAAAAGCGATTGTATTCTTAGTTTTGAATA
TCTTGACTTGGACTTGAAGAAGCACATGGATTCATCTCCTGAATTCTCTAAGGATCCACGTC
TGGTTAAAATGTTTCTGTATCAAATACTCCGTGGGATTGCTTATTGCCATTCTCATAGAGTT
CTTCATAGAGTTCTTCATCGAGATTTGAAGCCTCAAAACTTGCTGATAGGTCGACGTACAAA
TGCTTTAAAGCTTGCAGACTTTGGATTGGCTAGAGCATTTGGTATTCCTGTCAGAACTTTCA
CTCATGAGGTGGTGACATTGTGGTACAGGGCACCAGAAATACTGCTGGGATCACGCCATTAT
TCTACTCCTGTTGATGTGTGGTCAGTTGGTTGCATATTTGCTGAGATGGTGACTCAGCGCCC
TCTGTTTCCTGGTGACTCCGAGATTGATGAACTTTTCAAGATTTTCAGAGTGATGGGTACTC
CAAATGAGGATACATGGCCTGGAGTGACTACTCTGCCTGATTTTAAATCTGCCTTACCAAAA
TGGCCTTCTAAGGACCTGGCAACTATTGTCCCAAATCTTGATGGAGCAGGCCTTGATCTTCT
TGATAAAACTGTCCGCTTGGATCCCAGCAAGAGAATCACTGCCAGGAATGCCCTTGAGCATG
AGTACTTCAAGGATATTGGGTATGTGTTCCGTTCGAAGGGGTCCTCTAGAGTCG

SEQ ID NO: 46 cyclin dependent kinase [Petunia x hybrida] (CAA73997)
MDQYEKVEKIGEGTYGVVYKARDRVTNETIALKKIRLEQEDEGVPSTAIREISLLKEMQHAN
IVRLQDVVHTVKSDCILSFEYLDLDLKKHMDSSPEFSKDPRLVKMFLYQILRGIAYCHSHRV
LHRVLHRDLKPQNLLIGRRTNALKLADFGLARAFGIPVRTFTHEVVTLWYRAPEILLGSRHY
STPVDVWSVGCIFAEMVTQRPLFPGDSEIDELFKIFRVMGTPNEDTWPGVTTLPDFKSALPK
WPSKDLATIVPNLDGAGLDLLDKTVRLDPSKRITARNALEHEYFKDIGYVFRSKGSSRV

SEQ ID NO: 47 Picea abies cdc2Pa mRNA (X77680)
TTCGTGAATGCGTGTTTGAATCGCTGAATCTAGAGATTTCTCTCTAAATATTCCGACGGGTG
CAGAGAAAAAGTCGAACAGAACGGGAGCTTGAATCAGGCTGAATGGAGCAGTATGAGAAAGT
TGAGAAGATAGGAGAAGGAACATATGGTGTGGTCTACAAGGCCCGTGATCGCTTGACAAATG
AGACCATAGCTCTCAAGAAAATTCGTTTGGAGCAAGAAGATGAGGGTGTACCAAGCACTGCA
ATTAGAGAAATTTCTCTTCTCAAAGAAATGCAACATGGGAACATCGTAAGGTTGCAGGATGT
TGTCCACAGTGAAAAGCGTCTCTATTTAGTTTTTGAGTATTTGGACTTGGACCTCAAGAAGC
ATATGGATTCTTGCCCCGAGCTAGCAAAGGATCCTCGTCTAATCAAAACATTTCTGTATCAG
ATTCTGCGTGGCATTGCCTATTGTCATTCTCATCGAGTTCTTCATCGTGATTTGAAACCACA
AAATTTGCTTATTGACCGCAAAACCAATGCGTTGAAACTTGCCGACTTTGGACTTGCAAGGG
CATTTGGAATTCCAGTGAGGACCTTTACTCATGAGGTGGTTACATTGTGGTACCGTGCACCA
GAGATCTTGCTTGGGTCCCGACATTATTCGACTCCTGTTGATGTTTGGTCTGTGGGGTGTAT
CTTTGCTGAAATGGTGAATCAGCGACCACTTTTCCCAGGAGACTCAGAGATTGATGAACTCT
TTAAGATATTTAGAGTGCTGGGGACACCAAATGAAGAAACATGGCCAGGAGTCACCTCTCTG
CCAGACTTCAAGTCAGCCTTCCCAAAGTGGCCAGCCAAGGATTTGGCAACTGTGGTTCCAGG
TCTTGAGCCAGCAGGAATTGATCTTCTCGAAATGTTGTGCCTGGAGCCCAGTAAACGCA
TCACTGCTCGTAGTGCTCTGGAGCATGAGTATTTCAAAGATCTAGGTTTTGTACCCTGACCT
GTATATTAGCTGTGGGGTTAAGAAGATTATTGGACTGTTGTACTGTAGCTTGCATCTTCTCA

FIGURE 3 (continued)

CCAGTGAATTGCTTTTCGGAGACTGGTAAACTAGATGGAGACCTCTATAAGTAACATGATTA
AGTATATCATGTTTTTTGTATTTTGCCACATTTGTTAATGATTTGCACCTTTGGTGTAGCTG
GATTATGGCGCTTCTAGTTCTTCAAGACCATTGAACAATACTTTTTCTGGAAAGCAGATTGT
TTACGATTGTCAAATATGACTTATCATTTGAATTCTTTGCCATGTGTTCTCACTGATGGAG
TATTTTATAATATTGTGCATTCTGAT

SEQ ID NO: 48 cdc2Pa [Picea abies] (CAA54746)
MEQYEKVEKIGEGTYGVVYKARDRLTNETIALKKIRLEQEDEGVPSTAIREISLLKEMQHGN
IVRLQDVVHSEKRLYLVFEYLDLDLKKHMDSCPELAKDPRLIKTFLYQILRGIAYCHSHRVL
HRDLKPQNLLIDRKTNALKLADFGLARAFGIPVRTFTHEVVTLWYRAPEILLGSRHYSTPVD
VWSVGCIFAEMVNQRPLFPGDSEIDELFKIFRVLGTPNEETWPGVTSLPDFKSAFPKWPAKD
LATVVPGLEPAGIDLLSKMLCLEPSKRITARSALEHEYFKDLGFVP

SEQ ID NO: 49 Pinus contorta cdc2Pnc RNA (X80845)
CCGGTCTGAATCTTTGAATCTAGAGATTTCTCTCTAAATATTCCGACGGGTGCAGAGAAAAA
GTCGAACAGAACGGGATCTTGAATCAGGCTGAATGGAACAGTATGAGAAAGTTGAGAAGATA
GGAGAAGGAACATATGGTGTGGTTTACAAGGCCCGTGATCGCTTGACAAATGAGACCATAGC
TCTCAAGAAAATTCGTTTGGAGCAAGAAGATGAGGGTGTACCAAGCACTGCGATTAGAGAAA
TTTCTCTTCTTAAAGAAATGCAACATGGGAACATCGTAAGGTTGCAAGATGTTGTCCATAGT
GAAAAGCGGCTCTATTTGGTTTTCGAGTATTTGGATTTGGACCTCAAGAAGCATATGGATTC
TTGCCCTGAGCTAGCAAAGGATCCTCGTCTAATCAAAACATTTCTGTATCAGATTCTGCGTG
GCATTGCCTATTGTCATTCTCATCGGGTTCTTCATCGTGATCTGAAGCCGCAAAATTTGCTT
ATTGACCGCAAAACCAATGCGTTGAAACTTGCCGACTTTGGACTTGCCAGGGCATTTGGAAT
TCCAGTGAGGACCTTTACTCATGAGGTGGTTACATTGTGGTATCGTGCACCCGAGATCTTAC
TTGGTTCCCGGCATTATTCGACTCCTGTTGATGTTTGGTCTGTTGGATGTATCTTTGCTGAA
ATGGTCAATCAGCGACCACTTTTCCCAGGAGACTCAGAGATTGATGAGCTCTTTAAGATATT
TAGAGTGCTGGGGACGCCAAATGAAGAAACATGGCCAGGAGTCACCTCTCTGCCTGACTTCA
AGTCAGCCTTCCCAAAGTGGCCAGCCAAGGATTTGGCAACTGTGGTTTCAGGTCTTGAGCCA
GCAGGAATTGATATTCTCTCGAAATGCTGTGCCTGGAGCCCAGTAGACGCATCACTGCTCG
TAGTGCTCTGGAGCACGAGTATTTCAAAGATCTAGGTTTTGTACCCTGACCTGTATATTAGC
TGCGGGGATAAAAAGATTATTGGACTGTCGTAGCATAGCCTGCATCTTCTCACCAGTGAGTT
GCTCGTTGGAAGCTGGTAAACTAGATGGAAACCTGTATAAGTAAACATGATTAAGTATACCA
TGTTTTTTTTTTAAATATTTTGCCACACTTGTTAAGGATTTGCACCTTTGGTGTAGCTGGAT
TGTGGTGGTTCTAGTTCTTCAAGACTATTGAACAAAACTTTATTTGGAATTAAGTTGTTTA
CGATTGTCAAATATGACTGATCATTTGAATTCTTTGCCAAAAAAAAAAAA

SEQ ID NO: 50 cdc2Pnc [Pinus contorta] (CAA56815)
MEQYEKVEKIGEGTYGVVYKARDRLTNETIALKKIRLEQEDEGVPSTAIREISLLKEMQHGN
IVRLQDVVHSEKRLYLVFEYLDLDLKKHMDSCPELAKDPRLIKTFLYQILRGIAYCHSHRVL
HRDLKPQNLLIDRKTNALKLADFGLARAFGIPVRTFTHEVVTLWYRAPEILLGSRHYSTPVD
VWSVGCIFAEMVNQRPLFPGDSEIDELFKIFRVLGTPNEETWPGVTSLPDFKSAFPKWPAKD
LATVVSGLEPAGIDILSKMLCLEPSRRITARSALEHEYFKDLGFVP

FIGURE 3 (continued)

SEQ ID NO: 51 Pisum sativum mRNA for cdc2, complete cds (AB008187)
CTGAGACTAGACTATGTGACTGGAAAGACCATACGCCGCGCTGTCTGTGTAACGGTTTCTCG
CTCCGAACTAGAACATCGCTTTGAACTTAGAGAGTTTCTTCCATGGAACAGTATGAGAAGGT
TGAGAAAATAGGAGAAGGTACATACGGTGTGGTGTACAAGGCTAGGGACCGTGTTACCAATG
AGACCATTGCTTTGAAGAAGATTCGACTCGAACAGGAAGATGAGGGGGTTCCTAGCACTGCC
ATAAGAGAGATTTCTCTTTTGAAAGAAATGCAGCATCGGAACATTGTTAGGTTGCAGGATGT
TGTGCATAGTGAGAAGCGATTGTATCTTGTTTTTGAGTACCTTGACTTAGATCTAAAGAAGC
ATATGGATTCATCTCCGGAATTTTCCAAAGATCAACGTCAAGTAAAAATGTTCCTCTATCAA
ATTCTCTGTGGCATTGCTTACTGTCATTCTCATAGAGTTCTTCACCGAGACCTGAAACCACA
AAATCTGTTGATAGATCGCAGCTCTAATGCGCTAAAGCTTGCAGATTTTGGGTTGGCTAGAG
CATTTGGAATTCCTGTTAGGACATTTACACATGAGGTGGTGACACTATGGTACAGAGCTCCA
GAAATATTGCTTGGGTCCCGTCATTATTCTACCCCAGTTGATGTTTGGTCAGTGGGATGCAT
ATTTGCAGAGATGATAAACCAGCGACCACTTTTCCCTGGGGATTCTGAGATTGATGAATTGT
TTAAAATATTCAGAATCACGGGTACACCAAATGAAGATACATGGCCTGGAGTGACTTCATTG
CCTGATTTTAAATCCGCCTTTCCCAAGTGGCCATCTAAGGACCTGGCAACTCTGGTCCCAAG
TCTTGAGCCATCTGGTCTTGATCTGTTATCTAGTATGCTTCGCTTGGATCCCAGCAGAAGAA
TTACTGCCAGGGGCGCTCTTGAGCACGAATACTTCAAAGACATTAAATTTGTCCCCTGAAGT
CCTGGCTTCACTGAAGAGGTGTCTATATTATTATGTGTAGCAGTTATGGGTTTTTGGCTCAG
AAGTGTGTGCTATCCGTGCTATTTTCTTCAAATGCTTTGGACTGAGTAATATTT

SEQ ID NO: 52 cdc2 [Pisum sativum] (BAA33152)
MEQYEKVEKIGEGTYGVVYKARDRVTNETIALKKIRLEQEDEGVPSTAIREISLLKEMQHRN
IVRLQDVVHSEKRLYLVFEYLDLDLKKHMDSSPEFSKDQRQVKMFLYQILCGIAYCHSHRVL
HRDLKPQNLLIDRSSNALKLADFGLARAFGIPVRTFTHEVVTLWYRAPEILLGSRHYSTPVD
VWSVGCIFAEMINQRPLFPGDSEIDELFKIFRITGTPNEDTWPGVTSLPDFKSAFPKWPSKD
LATLVPSLEPSGLDLLSSMLRLDPSRRITARGALEHEYFKDIKFVP

SEQ ID NO: 53 Solanum tuberosum cdc2-like p34 kinase gene, partial cds (U53510)
GGAATTCAGAGAAAATTGGGGAAGGGACTTATGGCGTAGTGTACAAAGCTCGTGATCGTGTA
ACTAATGAAACTATTGCACTGAAGAAAATTCGGCTGGAGCAGGAAGATGAGGGTGTGCCAAG
CACGGCTATTAGAGAAATCTCCCTCTTGAAAGAGATGCAGCATGGAAACATTGTGAGGTTGC
AAGATGTGGTTCACAGTGAGAAGCGATTATATCTAGTGTTTGAATATCTCGACTTGGATTTG
AAGAAGCATATGGACTCATGTCCAGAGTTCTCTAAGGATCCGCGTCTTGTAAAAATGTTTTT
GTATCAAATTCTCCGTGGAATTGCTTATTGTCATTCTCATAGAGTTCTTCACCGAGATCTGA
AGCCTCAGAACTTGCTGATAGATAGACGTACAAATGTTCTAAAGCTAA

SEQ ID NO: 54 Solanum tuberosum p34 kinase (AAA98856)
NSEKIGEGTYGVVYKARDRVTNETIALKKIRLEQEDEGVPSTAIREISLLKEMQHGNIVRLQ
DVVHSEKRLYLVFEYLDLDLKKHMDSCPEFSKDPRLVKMFLYQILRGIAYCHSHRVLHRDLK
PQNLLIDRRTNVLKL

FIGURE 3 (continued)

SEQ ID NO: 55 Sesbania rostrata mRNA for cdc2 kinase-like protein (Z75661)
GCACGAGCTTCTCTTGTCTTGGTTGAGTGAGTGAGTGAGTCTCACTGCGCCAACAACTCTGT
CCCTTTCTTCTTCTTTTCAGATCTTGTATTTGTTTACTCAATTTCCCTCTTAAGTCTCT
TAGCTTTCAACTGAGACTTTGTTCCATGGAACAGTACGAGAAGGTCGAGAAGATTGGCGAAG
GAACATACGGCGTCGTTTATAAGGCCCGCGACCGCGTCACCAATGAGACCATCGCTCTCAAG
AAAATTCGCCTCGAGCAAGAGGACGAAGGGGTTCCCAGCACCGCCATACGCGAGATTTCTCT
CTTGAAAGAAATGCAGCATAGGAACATTATTAGGTTGCAAGATGTAGTGCACAGCGAGAAGC
GATTGTATCTGGTTTTTGAGTATCTGGACTTAGATCTAAAGAAGCACATGGATTCATCTCCT
GAGTTTGTGAAAGATCCGCGACAAGTAAAAATGTTCCTTTATCAAATTCTCTGTGGCATTGC
TTACTGTCATTCACATAGAGTTCTTCACCGAGACTTGAAACCACAGAATTTGTTGATAGATC
GCCGTACTAATTCACTAAAGCTTGCAGATTTTGGATTGGCTAGGGCATTTGGCATTCCTGTC
AGGACATTTACACATGAGGTTGTCACACTGTGGTACAGAGCTCCAGGCATATTGCTTGGATC
TCGTCATTATTCTACCCCAGTTGATATCTGGTCAGTGGGATGTATATTTGCAGAGATGGTAA
ACCGACGGCCTCTATTCCCTGGTGACTCTGAGATTGATGAATTGTTTAAAATATTCAGAATC
TTGGGTACACCAAATGAAGATACATGGCCCGGAGTAACTTCATTGCCTGATTTTAAATCAAC
ATTTCCCAAGTGGCCACCTAAGGATCTAGCAACTGTGGTTCCAAATCTTGAGCAAGCTGGTC
TTAATCTTCTTTCTAGTATGCTTTGCTTGGATCCCAGCAAAAGAATTACCGCCAGGAGCGCT
GTGGAGCATGAATACTTCAAAGACATTAAATTTGTACCCTGATTCCATATCTTCATGGCCAA
GGTGTTTATAGTAATATGTTCAGAATTTATGGGTTTTGACTATGCGAGAAATGCGTTCTATC
TTTGCTCTTTTCTTCAATGACTTGGGGCTGTCATATTTCAATTTTTTGTCCTTGCCAATATT
TCAGAATCAACTTGAGTGTGGAAAAAAAAAAAAAAAAAAAAAAAAAAAA

SEQ ID NO: 56 cdc2 kinase homologue [Sesbania rostrata] (CAA99991)
MEQYEKVEKIGEGTYGVVYKARDRVTNETIALKKIRLEQEDEGVPSTAIREISLLKEMQHRN
IIRLQDVVHSEKRLYLVFEYLDLDLKKHMDSSPEFVKDPRQVKMFLYQILCGIAYCHSHRVL
HRDLKPQNLLIDRRTNSLKLADFGLARAFGIPVRTFTHEVVTLWYRAPGILLGSRHYSTPVD
IWSVGCIFAEMVNRRPLFPGDSEIDELFKIFRILGTPNEDTWPGVTSLPDFKSTFPKWPPKD
LATVVPNLEQAGLNLLSSMLCLDPSKRITARSAVEHEYFKDIKFVP

SEQ ID NO: 57 Triticum aestivum p34cdc2 (cdc2TaA) mRNA, complete cds; U23409
GCCCCCCTCTCCCCCTCCCCCCCACCCCCCCAATGGCGGCAGCAGCAGCAGCAGCAGCAG
CAGCTTCGCCCGCCGCAGCCGCTCTCCCCGCCCCTCCTCCCCGTGATCCCCTTCCCCTT
CCCCTCCCCCGCTTCCTCCTCTCCCCCCTCCCGCCTCCTCACCCATTTCCCACGCCCGCG
CCGCCGCCGCCGTAGCATTGGACGCCGACCCGATGGAGCAGTACGAGAAGGTGGAGA
AGATCGGGGAGGGCACGTACGGGGTGGTGTACAAGGCCCGGGACAGGACCACCAACGAGA
CCATCGCGCTCAAGAAGATCCGCCTGGAGCAGGAGGACGAGGGCGTCCCCTCCACCGCCA
TCCGCGAGATCTCGCTCCTCAAGGAGATGCAGCACGGCAACATCGTCAAGCTGCACGATG
TTGTCCACAGCGAGAAGCGCATATGGCTCGTCTTTGAGTACCTGGATCTGGACCTGAAGA
AGTTCATGGACTCCTGTCCAGAGTTTGCCAAGAGCCCCGCCTTGATCAAGTCATATCTCT
ATCAGATACTCCGCGGCGTTGCTTACTGTCATTCTCATAGAGTTCTTCATCGAGATTTGA
AACCTCAGAATTTATTGATAGACCGGCGTACTAATGCACTGAAGCTTGCAGACTTTGGTT
TAGCAAGGGCATTTGGAATTCCTGTCCGTACATTTACTCATGAGGTAGTAACATTATGGT

FIGURE 3 (continued)

ACAGAGCTCCTGAAATCCTTCTTGGAGCAAGGCAGTATTCCACACCAGTTGACGTGTGGT
CAGTGGGCTGTATCTTTGCAGAAATGGTGAACCAGAAACCACTGTTCCCTGGCGATTCTG
AGATTGATGAGCTATTTAAGATATTCAGGGTACTCGGCACTCCAAATGAACAAACTTGGC
CAGGCGTGAGTTCCTTGCCTGACTACAAGTCCGCCTTCCCCAGGTGGCAGGCAGAGGACC
TTGCAACCGTTGTCCCCAATCTTGAACCTGTTGGCCTGGACCTTCTCGAAAATGCTTC
GGTTCGAGCCAAACAAGAGGATCACGGCTAGGCAGGCTCTTGAGCATGAGTACTTCAAGG
ACATGGAGATGGTACAGTGAGCTGGCTATGTGGTAGTGACTGGCATATGTATGAGCTGAG
CTGCTCGTTTCATTCCTTTTGTGAACGCTC

SEQ ID NO: 58 Triticum aestivum p34cdc2 (AAD10483)
MEQYEKVEKIGEGTYGVVYKARDRTTNETIALKKIRLEQEDEGVPSTAIREISLLKEMQH
GNIVKLHDVVHSEKRIWLVFEYLDLDLKKFMDSCPEFAKSPALIKSYLYQILRGVAYCHS
HRVLHRDLKPQNLLIDRRTNALKLADFGLARAFGIPVRTFTHEVVTLWYRAPEILLGARQ
YSTPVDVWSVGCIFAEMVNQKPLFPGDSEIDELFKIFRVLGTPNEQTWPGVSSLPDYKSA
FPRWQAEDLATVVPNLEPVGLDLLSKMLRFEPNKRITARQALEHEYFKDMEMVQ

SEQ ID NO: 59 Triticum aestivum p34cdc2 (cdc2TaB) mRNA, partial cds; U23410.1
CCCACCCCACTCCTCCCCGCCGCCGCCGCCGCCCCGCTCCGATCCGCCCCGCGCCGC
GCGGATCGCCGCGCCATGGACCAGTACGAGAAGGTGGAGAAGATCGGGGAGGGCACGTAC
GGGGTGGTGTACAAGGCCAAGGACCGCTACACCAACGAGACGATCGCGCTCAAGAAGATC
CGGCTGGAGCAGGAGGACGAGGGCGTCCCCTCCACCGCCATCCGCGAGATCTCCCTCCTC
AAGGAGATGCAGCACCGGAACATCGTCAGGCTGCAGGACGTGGTGCACAACGAGAAGTGC
ATATACCTCGTCTTCGAGTACCTCGACCTCGACCTCAAGAAGCACATGGACTCCTCCGCG
GACTTCAAGAACCACCACATAGTCAAGTCCTTCCTCTACCAGATCCTGCACGGCATCGCC
TACTGCCACTCGCACCGTGTGCTTCACAGGGATCTCAAGCCCCAGAACCTGCTGATAGAT
CGCCGTACCAATTCATTGAAGCTTGCTGACTTCGGATTGGCGAGGGCGTTCGGCATTCCT
GTCCGGACATTTACTCACGAGGTGGTGACATTATGGTATAGAGCACCAGAAATTCTTCTG
GGTGCGAGGCAGTATTCTACCCCTGTTGATGTGTGGTCGGTTGGTTGCATTTTCGCCGAA
ATGGTGAATCAGAAACCTCTATTTCCTGGTGATTCTGAGATTGATGAACTCTTCAAGATT
TTCAGAATTATGGGCACTCCTAATGAAGAAACCTGGCCAGGTGTTTCTTCGTTACCTGAC
TACAAATCAGCTTTCCCCAAGTGGCCATCCGTGGATCTTGCAACTGTGGTTCCAACACTC
GAACCTTTGGGACTTGATCTTCTCTCTAAAATGCTCTGCTTAGATCCAACCAGAAGAATC
AACGCCCGAACCGCC

SEQ ID NO: 60 p34cdc2 [Triticum aestivum] (AAD10484)
MDQYEKVEKIGEGTYGVVYKAKDRYTNETIALKKIRLEQEDEGVPSTAIREISLLKEMQHRN
IVRLQDVVHNEKCIYLVFEYLDLDLKKHMDSSADFKNHHIVKSFLYQILHGIAYCHSHRVLH
RDLKPQNLLIDRRTNSLKLADFGLARAFGIPVRTFTHEVVTLWYRAPEILLGARQYSTPVDV
WSVGCIFAEMVNQKPLFPGDSEIDELFKIFRIMGTPNEETWPGVSSLPDYKSAFPKWPSVDL
ATVVPTLEPLGLDLLSKMLCLDPTRRINARTA

FIGURE 3 (continued)

SEQ ID NO: 61 Vigna acunitifolia protein kinase mRNA, complete cds (M99497)
GCGGGTAGTGTATACAATTTGTAAATAGTTAAAAGAAAAGCATTAAACAAAAAAAGAGGGAA
AAGGGTAGTAAAGGAAAGAGAAGAAAGAGTTGAGAAGAGTGAAAGAGAGAGAGAGAGAGAGA
GAGAGAAGAAGTGACAAGAGTGGAGTGTGCGTGAGAGAGTGACTGCAAAACGCTCCACCCTT
GTTTCTTCTCAGATCTTCCATGGAACAGTACGAGAAGGTGGAGAAGATAGGGGAGGGAACAT
ACGGCGTCGTTTACAAGGCTCGCGACCGCGTCACCAATGAGACCATCGCTCTTAAGAAGATT
CGCCTCGAGCAGGAAGACGAGGGGGTTCCCAGCACCGCCATTCGTGAGATTTCGCTCCTCAA
AGAGATGCAGCATAGGAACATTGTTAGGTTGCAGGATGTAGTGCACAGTGAGAAGCGATTGT
ATCTGGTTTTCGAGTATCTGGACTTGGATCTAAAGAAACACATGGATTCATCTCCAGAGTTT
GTGAAAGATCCACGGCAAGTAAAAATGTTCCTCTATCAAATTCTCTGTGGCATTGCTTACTG
CCATTCGCACAGAGTTCTTCATCGAGACTTGAAACCACAGAATTTGTTGATAGACCGTCGTA
CAAATTCCTTAAAACTTGCAGATTTTGGATTGGCTAGGGCATTTGGCATTCCTGTCAGGACA
TTTACTCATGAGGTGGTGACATTATGGTACAGAGCTCCAGAAATATTGCTTGGGTCTCGTCA
TTATTCTACCCCAGTTGATGTTTGGTCAGTGGGATGTATATTTGCAGAGATGGTAAACCGAC
GACCTCTATTCCCAGGGGACTCTGAGATTGATGAATTATTTAAAATATTCAGAATATTGGGT
ACACCTAATGAAGAAACATGGCCTGGAGTTACTGCATTACCGGATTTTAAATCAACATTTCC
CAAATGGCCACCTAAGGATTTAGCAACTGTGGTTCCAAATCTTGATGCAGCGGGTCTTAATC
TTCTTTCTAGTATGCTATGCTTGGATCCCAGCAAAAGAATTACTGCCAGGATCGCTGTGGAG
CACGAATACTTCAAAGACATTAAATTTGTACCCTAATTCCATATCTTCATGGAAACCGTGTT
TATAGTAATATTTTGTGCAGAATTTATGGGTTTTGACTCTGCGAGAAATGCGTGCTGTCTTT
TGCTATTTCTTCAGGACTTGGGAGTTGGGAGTGGGTCATATTTCCATTTTTTGTCCTACAGA
TATTTGAGAATGAACTTGAGTGTGATCATACTGCATTTTACATTTCCCTTTGTCCATGCAAT
GCAATGCACCAGTTAACTTTTC

SEQ ID NO: 62 Vigna acunitifolia protein kinase (AAA34241)
MEQYEKVEKIGEGTYGVVYKARDRVTNETIALKKIRLEQEDEGVPSTAIREISLLKEMQHRN
IVRLQDVVHSEKRLYLVFEYLDLDLKKHMDSSPEFVKDPRQVKMFLYQILCGIAYCHSHRVL
HRDLKPQNLLIDRRTNSLKLADFGLARAFGIPVRTFTHEVVTLWYRAPEILLGSRHYSTPVD
VWSVGCIFAEMVNRRPLFPGDSEIDELFKIFRILGTPNEETWPGVTALPDFKSTFPKWPPKD
LATVVPNLDAAGLNLLSSMLCLDPSKRITARIAVEHEYFKDIKFVP

SEQ ID NO: 63 Vigna unguiculata mRNA for protein kinase (X89400)
CGAAGTGACAAGAGTGGAGTGTGCGTGAGAGAGTGACTGCAAACCGCTCCACCCTTGTTTCT
TCTCAGATCTTCCATGGAACAGTACGAGAAGGTGGAGAAGATAGGCGAGGGAACATACGGCG
TCGTTTACAAGGCTCGGGACCGCGTCACTGATGAGACCATCGCGCTCAAGAAGATTCGCCTG
GAGCAGGAGGACGAGGGGGTTCCCAGCACCGCCATTCGTGAGATTTCGCTCCTCAAAGAGAT
GCAGCATAGGAACATTGTTAGGTTGCAGGATGTAGTGCACAGTGAGAAACGATTGTATCTGG
TTTTCGAGTATCTGGACTTGGATCTAAAGAAACACATGGATTCATCTCCAGAGTTTGTGAAA
GATCCACGGCAAGTAAAAATGTTCCTCTATCAAATTCTCTGTGGCATTGCTTACTGCCATTC
GCACAGAGTTCTTCATCGAGACTTGAAACCACAGAATTTGTTGATAGACCGTCGTACAAATT
CCTTAAAACTTGCAGATTTTGGATTGGCTAGGGCATTTGGCATTCCTGTCAGGACATTTACT
CATGAGGTGGTGACATTATGGTACAGAGCTCCAGAAATATTGCTCGGGTCTCGTCATTATTC
TACCCCAGTTGATGTTTGGTCAGTGGGATGTTTATTTGCAGAGATGGTAAACCGACGACCTC FIGURE 3 (continued)

```
TATTCCCTGGGGACTCTGAGATTGATGAATTATTTAAAATATTCAGAATATTGGGTACACCA
AATGAAGAAACATGGCCTGGAGTTACTGCATTACCGGATTTTAAATCAACATTTCCCAAATG
GCCACCTAAGGATTTAGCAACTATGGTTCCAAATCTTGATGCAGCCGGTCTTAATCTTCTTT
CTAGTATGCTAAGCCTGGATCCCAGCAAAGAATTACCGCCAGGATCGCTGTGGAGCATGAA
TACTTCAAAGACATTAAATTTGTACCCTGATTCCATATCTTCATGGAAACGTGTTTATAGT
AATATTTTGCGCAGAATTTATGGGTTTTGACTCTGCGAGAAATGCGTGTTGTCTTTTGCTAT
TTTCTTCAGGACTTGGGAGTTGGGACTGGGTCATATTCCATTTTTTGTCCTACAGAATATTT
CAGAATCAACTTGAGTGTGATCAAATTGCATTTTACTTTTCCTTTTGTCCAGTCAATGCAAT
GCAGCATTTAAGTTTTCAGTTTGTCTGATATGTGTGATGCTGCTTCTTGATACAGAAGAAGC
GTATCTACATTCTTTCAAGATGCGTTGATTGATAAAATTAGTTTCATTTGTGTTTTTCCAAA
AAAAAAA
```

SEQ ID NO: 64 protein kinase [Vigna unguiculata] (CAA61581)
```
MEQYEKVEKIGEGTYGVVYKARDRVTDETIALKKIRLEQEDEGVPSTAIREISLLKEMQHRN
IVRLQDVVHSEKRLYLVFEYLDLDLKKHMDSSPEFVKDPRQVKMFLYQILCGIAYCHSHRVL
HRDLKPQNLLIDRRTNSLKLADFGLARAFGIPVRTFTHEVVTLWYRAPEILLGSRHYSTPVD
VWSVGCLFAEMVNRRPLFPGDSEIDELFKIFRILGTPNEETWPGVTALPDFKSTFPKWPPKD
LATMVPNLDAAGLNLLSSMLSLDPSKRITARIAVEHEYFKDIKFVP
```

SEQ ID NO: 65 Zea mays protein cdc2 kinase mRNA, complete cds (M60526)
```
CGCGGGCGAGGAGCAGACCAGCACCCAGCGCCCTCGTCGGGGGCGGCACGTGCAGCTTCAC
CAGCCGCCGCCTTTCCCCGTCTGCCTCTGCCTCTGCCTCTCCCCCTAACCCCCTTCCATTT
CTCCACCCCACCCCGCTCCCGCTTCCGCTTCCTCGCCACTTAGTTCGTTGCCACCACGCCGC
GGCTGCGTTCGCATTGGGGGCACGCAATGGAGCAGTACGAGAAGGTGGAGAAGATCGGGGAG
GGCACGTACGGGGTGGTGTACAAGGCGCTGGACAAGGCCACCAACGAGACGATCGCGCTCAA
GAAGATCCGCCTCGAGCAGGAGGACGAGGGCGTCCCGTCCACCGCCATCCGCGAGATCTCTC
TCCTCAAGGAGATGAACCACGGCAACATCGTCAGATTACATGATGTTGTCCACAGCGAGAAG
CGCATATACCTTGTCTTCGAGTACCTGGATCTGGACCTCAAGAAGTTCATGGACTCCTGCCC
GGAGTTTGCTAAGAATCCCACTTTGATCAAGTCATACCTCTACCAGATACTCCACGGTGTTG
CGTACTGCCATTCTCATAGAGTTCTTCATCGAGACTTGAAACCTCAAAACTTATTGATAGAT
CGGCGCACTAATGCACTGAAGCTTGCAGACTTTGGTTTAGCCAGGGCATTTGGAATTCCTGT
CCGTACATTTACTCATGAGGTAGTGACATTATGGTACAGAGCTCCAGAAATTCTGCTTGGAG
CGCGGCAGTATTCCACACCAGTTGATGTGTGGTCTGTGGCTGTATCTTTGCGGAAATGGTG
AACCAAAAGCCACTATTCCCTGGCGATTCTGAGATCGACGAACTTTTAAGATATTCAGGAT
ACTAGGTACACCGAATGAGCAGAGTTGGCCAGGAGTCAGTTGTTTGCCTGACTTCAAGACAG
CTTTCCCCAGGTGGCAAGCTCAGGACCTGGCAACAGTAGTCCCAAATCTTGACCCTGCTGGG
TTGGACCTTCTCTCTAAAATGCTTCGATACGAGCCAAGCAAAAGAATCACAGCGAGGCAAGC
ACTTGAGCATGAGTACTTCAAGGACCTTGAAGTGGTACAGTGACCTGCTAAATGTGCTTGAC
GTTGCATTGACATTTGTATGAGCTGAGTCGCTCATTCCTTTTATGAACGCCTGTACTCTTC
TCATTCTCTCCCTGCATTTTGTCATTCAGCTGGATATTTCGAATCTGGTGTGTTTGAGAT
GTATTAAAGAACGTCAAATAGATTACCGCCTTGGTCTCTGTCCATTGAAAGTAAATATCCGT
CATAAAAAAAAAAAAAAAAAAA
```

FIGURE 3 (continued)

SEQ ID NO: 66 Zea mays protein cdc2 kinase (AAA33479)
MEQYEKVEKIGEGTYGVVYKALDKATNETIALKKIRLEQEDEGVPSTAIREISLLKEMNHGN
IVRLHDVVHSEKRIYLVFEYLDLDLKKFMDSCPEFAKNPTLIKSYLYQILHGVAYCHSHRVL
HRDLKPQNLLIDRRTNALKLADFGLARAFGIPVRTFTHEVVTLWYRAPEILLGARQYSTPVD
VWSVGCIFAEMVNQKPLFPGDSEIDELFKIFRILGTPNEQSWPGVSCLPDFKTAFPRWQAQD
LATVVPNLDPAGLDLLSKMLRYEPSKRITARQALEHEYFKDLEVVQ

FIGURE 3 (continued)

```
                        SEQUENCE LISTING

<160> NUMBER OF SEQ ID NOS: 67

<210> SEQ ID NO 1
<211> LENGTH: 885
<212> TYPE: DNA
<213> ORGANISM: Oryza sativa

<400> SEQUENCE: 1
atggagcagt acgagaagga ggagaagatt ggggagggca cgtacggggt ggtgtacagg        60
gcgcgggaca aggtcaccaa cgagacgatc gcgctcaaga agatccggct tgagcaggag       120
gatgagggcg tcccctccac cgcaatccgc gagatctcgc tcctcaagga gatgcatcac       180
ggcaacatcg tcaggttaca cgatgttatc cacagtgaga agcgcatata tcttgtcttt       240
gagtatctgg atctggacct aaagaagttc atggactctt gtccagagtt tgcgaaaaac       300
cccactttaa ttaagtcata tctctatcag atactccgcg gcgttgctta ctgtcattct       360
catagagttc ttcatcgaga tttgaaacct cagaatttat tgatagatcg gcgtactaat       420
gcactgaagc ttgcagactt tggtttagcc agggcatttg gaattcctgt ccgcacgttt       480
gatcacgagg ttgtaaccct gtggtataga gctccagaga tccttcttgg atcaaggcag       540
tattctacac cagttgatat gtggtcagtt ggttgtatct ttgcagaaat ggtgaaccag       600
aaaccactgt tccctggtga ttctgagatt gatgaattat ttaagatatt cagggtacta       660
ggaactccaa atgaacaaag ttggccagga gttagctcat tacctgacta caagtctgct       720
ttccccaagt ggcaggcaca ggatcttgca actattgtcc ctactcttga ccctgctggt       780
ttggaccttc tctctaaaat gcttcggtac gagccaaaca aaaggatcac agctagacag       840
gctcttgagc atgaatactt caaggacctt gagatggtac aatga                        885

<210> SEQ ID NO 2
<211> LENGTH: 294
<212> TYPE: PRT
<213> ORGANISM: Oryza sativa

<400> SEQUENCE: 2

Met Glu Gln Tyr Glu Lys Glu Glu Lys Ile Gly Glu Gly Thr Tyr Gly
1               5                   10                  15

Val Val Tyr Arg Ala Arg Asp Lys Val Thr Asn Glu Thr Ile Ala Leu
```

-continued

```
                        20                  25                  30
Lys Lys Ile Arg Leu Glu Gln Glu Asp Glu Gly Val Pro Ser Thr Ala
             35                  40                  45
Ile Arg Glu Ile Ser Leu Leu Lys Glu Met His His Gly Asn Ile Val
 50                  55                  60
Arg Leu His Asp Val Ile His Ser Glu Lys Arg Ile Tyr Leu Val Phe
 65                  70                  75                  80
Glu Tyr Leu Asp Leu Asp Leu Lys Lys Phe Met Asp Ser Cys Pro Glu
                 85                  90                  95
Phe Ala Lys Asn Pro Thr Leu Ile Lys Ser Tyr Leu Tyr Gln Ile Leu
            100                 105                 110
Arg Gly Val Ala Tyr Cys His Ser His Arg Val Leu His Arg Asp Leu
        115                 120                 125
Lys Pro Gln Asn Leu Leu Ile Asp Arg Arg Thr Asn Ala Leu Lys Leu
    130                 135                 140
Ala Asp Phe Gly Leu Ala Arg Ala Phe Gly Ile Pro Val Arg Thr Phe
145                 150                 155                 160
Asp His Glu Val Val Thr Leu Trp Tyr Arg Ala Pro Glu Ile Leu Leu
                165                 170                 175
Gly Ser Arg Gln Tyr Ser Thr Pro Val Asp Met Trp Ser Val Gly Cys
            180                 185                 190
Ile Phe Ala Glu Met Val Asn Gln Lys Pro Leu Phe Pro Gly Asp Ser
        195                 200                 205
Glu Ile Asp Glu Leu Phe Lys Ile Phe Arg Val Leu Gly Thr Pro Asn
    210                 215                 220
Glu Gln Ser Trp Pro Gly Val Ser Ser Leu Pro Asp Tyr Lys Ser Ala
225                 230                 235                 240
Phe Pro Lys Trp Gln Ala Gln Asp Leu Ala Thr Ile Val Pro Thr Leu
                245                 250                 255
Asp Pro Ala Gly Leu Asp Leu Leu Ser Lys Met Leu Arg Tyr Glu Pro
            260                 265                 270
Asn Lys Arg Ile Thr Ala Arg Gln Ala Leu Glu His Glu Tyr Phe Lys
        275                 280                 285
Asp Leu Glu Met Val Gln
    290
```

<210> SEQ ID NO 3
<211> LENGTH: 53
<212> TYPE: DNA
<213> ORGANISM: Artificial sequence
<220> FEATURE:
<223> OTHER INFORMATION: primer: prm04553

<400> SEQUENCE: 3
ggggacaagt ttgtacaaaa aagcaggctt cacaatggag cagtacgaga agg    53

<210> SEQ ID NO 4
<211> LENGTH: 50
<212> TYPE: DNA
<213> ORGANISM: Artificial sequence
<220> FEATURE:
<223> OTHER INFORMATION: primer: prm04554

<400> SEQUENCE: 4
ggggaccact ttgtacaaga aagctgggtt cattgtacca tctcaaggtc    50

<210> SEQ ID NO 5

<211> LENGTH: 2709
<212> TYPE: DNA
<213> ORGANISM: Artificial sequence
<220> FEATURE:
<223> OTHER INFORMATION: expression cassette

<400> SEQUENCE: 5

```
cgtagtggct ggctgggcga cgtgggttta aggaagagt gacctgctca agtgctcagt      60
agattaatta agggatttga attctggtcg tacgataaat taacttgagt tcaaaaatac    120
aagaaacatc agtttatatt tcatttcgtg taggacctat caatccaatt cgtacaagag    180
gaattgcata tttcaactca tagtcttaac taccattcaa attgatattt gcacgatgat    240
gattgtctgg tatagatttg acttttggg aactgaatca aatccagcat gattcatgca     300
agaaacttga attcaactca tacaagaaac atattcaatt tcaagctgtg caataatgca    360
cgtatcttaa gcaaagagta gtacgtctgc atcatatagt actcatgcaa gattgaaaca    420
gctaagaact tgatcaaatt caagtttttt ttgtgatcga agtttaaatc cagttcatac    480
aagaaacgca ttaaaaataa tcgatttaaa tatgagcaat aatgcatcta ctttaagcat    540
agggtttgac atcacggtat ggaagcaaat ttgaattaga cgcaaacttg gatctcattt    600
ttccagaaac tttgttcgat tggtaattaa acagtgcaa cctttgcacg caaccaaata     660
tataaaaatc cctggttgct aggactgttg taatcctgac aaatttcctc taatcttaaa    720
acacttgggt cggctttctt tgccaacccg gcgaaaaaaa actatataaa aatcataatt    780
attactacct tcatttcagg ttataagact ttctaacatt gtccatattt atatatatgt    840
taatgaatct agacatatat ttgtgtctgg attcattaac atctatatga atgtggacaa    900
tgctagaaag ttttataacc tgaaacggag aagtatattt ttttgggtac ttgtgtcata    960
ttgtcatgtc atcaatgtgt atagtactaa ggttcaatga gaaatgatac aattgcaagc   1020
caaacaaatt gccgttacag aaatctgacg tcaacgacat tctggcaaga taatgcttga   1080
tacaatttgt gcagctatgc tactataaat agggggggg ggggcgttat atctgcactg    1140
agttcatatc aagcttttcaa tctctcattg catacaagtc cctgaagagt ttacaagaga   1200
cccagaagat catttttca ccagcaaagt tcatttaaat caactaggga tatcacaagt    1260
ttgtacaaaa aagcaggctt cacaatggag cagtacgaga aggaggagaa gattggggag   1320
ggcacgtacg gggtggtgta cagggcgcgg gacaaggtca ccaacgagac gatcgcgctc   1380
aagaagatcc ggcttgagca ggaggatgag ggcgtcccct ccaccgcaat ccgcgagatc   1440
tcgctcctca aggagatgca tcacggcaac atcgtcaggt tacacgatgt tatccacagt   1500
gagaagcgca tatatcttgt ctttgagtat ctggatctgg acctaaagaa gttcatggac   1560
tcttgtccag agtttgcgaa aaccccact ttaattaagt catatctcta tcagatactc    1620
cgcggcgttg cttactgtca ttctcataga gttcttcatc gagatttgaa acctcagaat   1680
ttattgatag atcggcgtac taatgcactg aagcttgcag actttggttt agccagggca   1740
tttggaattc ctgtccgcac gtttgatcac gaggttgtaa ccttgtggta tagagctcca   1800
gagatccttc ttgatcaag gcagtattct acaccagttg atatgtggtc agttggttgt   1860
atctttgcag aaatggtgaa ccagaaacca ctgttccctg tgattctga gattgatgaa    1920
ttatttaaga tattcagggt actaggaact ccaaatgaac aaagttggcc aggagttagc   1980
tcattacctg actacaagtc tgctttcccc aagtggcagg cacaggatct tgcaactatt   2040
gtccctactc ttgaccctgc tggttttggac cttctctcta aaatgcttcg gtacgagcca   2100
aacaaaagga tcacagctag acaggctctt gagcatgaat acttcaagga ccttgagatg   2160
```

```
gtacaatgaa cccagctttc ttgtacaaag tggtgatatc acaagcccgg gcggtcttct    2220
agggataaca gggtaattat atccctctag atcacaagcc cgggcggtct tctacgatga    2280
ttgagtaata atgtgtcacg catcaccatg ggtggcagtg tcagtgtgag caatgacctg    2340
aatgaacaat tgaaatgaaa agaaaaaaag tactccatct gttccaaatt aaaattcatt    2400 ttaaccttt aataggttta tacaataatt gatatatgtt ttctgtatat gtctaatttg    2460
ttatcatccg ggcggtcttc tagggataac agggtaatta tatccctcta gacaacacac    2520
aacaaataag agaaaaaaca aataatatta atttgagaat gaacaaaagg accatatcat    2580
tcattaactc ttctccatcc atttccattt cacagttcga tagcgaaaac cgaataaaaa    2640
acacagtaaa ttacaagcac aacaaatggt acaagaaaaa cagttttccc aatgccataa    2700
tactcgaac                                                            2709

<210> SEQ ID NO 6
<211> LENGTH: 1208
<212> TYPE: DNA
<213> ORGANISM: Oryza sativa

<400> SEQUENCE: 6
cgtagtggct ggctgggcga cgtgggttta aaggaagagt gacctgctca agtgctcagt      60
agattaatta agggatttga attctggtcg tacgataaat taacttgagt tcaaaaatac     120
aagaaacatc agtttatatt tcatttcgtg taggacctat caatccaatt cgtacaagag     180
gaattgcata tttcaactca tagtcttaac taccattcaa attgatattt gcacgatgat     240
gattgtctgg tatagatttg acttttggg aactgaatca atccagcat gattcatgca       300 agaaacttga attcaactca tacaagaaac atattcaatt tcaagctgtg caataatgca     360
cgtatcttaa gcaaagagta gtacgtctgc atcatatagt actcatgcaa gattgaaaca     420
gctaagaact tgatcaaatt caagtttttt ttgtgatcga agtttaaatc cagttcatac     480
aagaaacgca ttaaaaataa tcgatttaaa tatgagcaat aatgcatcta ctttaagcat     540
agggtttgac atcacggtat ggaagcaaat ttgaattaga cgcaaacttg gatctcattt     600
ttccagaaac tttgttcgat tggtaattaa acagtgcaa cctttgcacg caaccaaata      660
tataaaaatc cctggttgct aggactgttg taatcctgac aaatttcctc taatcttaaa    720
acacttgggt cggctttctt tgccaacccg gcgaaaaaaa actatataaa aatcataatt    780
attactacct tcatttcagg ttataagact ttctaacatt gtccatattt atatatatgt    840
taatgaatct agacatatat ttgtgtctgg attcattaac atctatatga atgtggacaa    900
tgctagaaag tttataacc tgaaacggag aagtatattt ttttgggtac ttgtgtcata     960
ttgtcatgtc atcaatgtgt atagtactaa ggttcaatga gaaatgatac aattgcaagc   1020
caaacaaatt gccgttacag aaatctgacg tcaacgacat tctggcaaga taatgcttga   1080
tacaatttgt gcagctatgc tactataaat agggggggggg ggggcgttat atctgcactg   1140
agttcatatc aagctttcaa tctctcattg catacaagtc cctgaagagt ttacaagaga   1200
cccagaag                                                            1208

<210> SEQ ID NO 7
<211> LENGTH: 1115
<212> TYPE: DNA
<213> ORGANISM: Oryza sativa

<400> SEQUENCE: 7
```

-continued

```
acctctcctc cgattaatcc cctcccctcc tcttcctccc acttctgcgc ctgctcttcc      60
tcccctcgcc gaccctacct actcgcgccg ccgccgtcgc attgggcggc aaacggaggg     120
ggggttaacc ctgatggagc agtacgagaa ggaggagaag attggggagg gcacgtacgg     180
ggtggtgtac agggcgcggg acaaggtcac caacgagacg atcgcgctca agaagatccg     240
gcttgagcag gaggatgagg gcgtcccctc caccgcaatc cgcgagatct cgctcctcaa     300
ggagatgcat cacggcaaca tcgtcaggtt acacgatgtt atccacagtg agaagcgcat     360
atatcttgtc tttgagtatc tggatctgga cctaaagaag ttcatggact cttgtccaga     420
gtttgcgaaa accccacttt aattaagtc atatctctat cagatactcc gcggcgttgc      480
ttactgtcat tctcatagag ttcttcatcg agatttgaaa cctcagaatt tattgataga     540
tcggcgtact aatgcactga agcttgcaga ctttggttta gccagggcat ttggaattcc     600
tgtccgcacg tttactcacg aggttgtaac cttgtggtat agagctccag agatccttct     660
tggatcaagg cagtattcta caccagttga tatgtggtca gttggttgta tctttgcaga     720
aatggtgaac cagaaaccac tgttccctgg tgattctgag attgatgaat atttaagat      780
attcagggta ctaggaactc caaatgaaca aagttggcca ggagttagct cattacctga     840
ctacaagtct gctttcccca gtggcaagc acaggatctt gcaactattg ccctactct       900
tgaccctgct ggtttggacc ttctctctaa aatgcttcgg tacgagccaa acaaaaggat     960
cacagctaga caggctcttg agcatgaata cttcaaggac cttgagatgg tacaatgacc    1020
ctgctatggc tttacattgg attggcatat gtatgggctg ggctcctcat ttcattcctt    1080
ctgtgaacgc tgtgcccttc gtttgggcat tttg                                 1115
```

<210> SEQ ID NO 8
<211> LENGTH: 294
<212> TYPE: PRT
<213> ORGANISM: Oryza sativa

<400> SEQUENCE: 8

```
Met Glu Gln Tyr Glu Lys Glu Glu Lys Ile Gly Glu Gly Thr Tyr Gly
1               5                   10                  15

Val Val Tyr Arg Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met His His Gly Asn Ile Val
    50                  55                  60

Arg Leu His Asp Val Ile His Ser Glu Lys Arg Ile Tyr Leu Val Phe
65                  70                  75                  80

Glu Tyr Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175
```

-continued

```
Gly Ser Arg Gln Tyr Ser Thr Pro Val Asp Met Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Gln Ser Trp Pro Gly Val Ser Ser Leu Pro Asp Tyr Lys Ser Ala
225                 230                 235                 240

Phe Pro Lys Trp Gln Ala Gln Asp Leu Ala Thr Ile Val Pro Thr Leu
                245                 250                 255

Asp Pro Ala Gly Leu Asp Leu Leu Ser Lys Met Leu Arg Tyr Glu Pro
            260                 265                 270

Asn Lys Arg Ile Thr Ala Arg Gln Ala Leu Glu His Glu Tyr Phe Lys
        275                 280                 285

Asp Leu Glu Met Val Gln
    290
```

<210> SEQ ID NO 9
<211> LENGTH: 1260
<212> TYPE: DNA
<213> ORGANISM: Allium cepa

<400> SEQUENCE: 9

| | | |
|---|---|---|
| ctctatatta ttttgtggga gaattttgcg ctggattcgt tcatcaaacc ctagctacaa | 60 |
| cgcagtatgg tttggattga atggatcagt atgagaaagt ggagaagatt ggagaaggaa | 120 |
| cttatggagt tgtttacaaa gcacgtgatc ggctgactaa tgaaacgatt gctttgaaga | 180 |
| agattaggtt ggagcaggaa gatgagggag ttcctagtac tgccattaga gaaatatcac | 240 |
| tgttgaagga aatgcagcat gctaacattg tcaggctgca agacgtagtt catagtgaga | 300 |
| agcgaatata tcttgtgttc gagtatctag atctggacct taagaagcat atggattcat | 360 |
| gcccagattt tgctaaagat tctcgtttgg ctaaaacatt tctctatcag cttctccgag | 420 |
| gaattgctta ttgtcactca caccgagttc ttcatcgtga cttaaagcct caaaatttat | 480 |
| tgatcgacag acgtaccaat tcattaaagc ttgctgactt tggacttgca agggcatttg | 540 |
| gtatcccagt ccgaaccttc acacacgagg ttgtgacact gtggtatagg gcacctgaaa | 600 |
| tcctcttagg tgctcgtcag tattctactc ctgtagacat atggtctgtg ggatgtatct | 660 |
| ttgctgaaat ggtgaaccaa cgacctctat tccctgggga ctctgagatc gacgagctgt | 720 |
| tcaaaatatt tagaattatg ggtaccccaa acgaagacac atggccaggt gttacttcct | 780 |
| tgcccgactt caagtctgct tttccaaagt ggccggcaaa ggacttggca actatagttc | 840 |
| caaagcttga ttcagctgga attgatcttc tttataaaat gctgcacctt gaaccgagca | 900 |
| aaagaatcac tgctcggaag gctcttgagc atgaatactt cagggatctt gggacaattc | 960 |
| catgaaacaa ctgagcacat ccttccccat tgtatattat tatgaccatt gcatcaacct | 1020 |
| ttgcagattg gtatgtttga gtgccgtcct ttgttatctt tcggtttttt attcaatctt | 1080 |
| attcaagttt gtgtgtttta gacagctagg gagccttcac ttatccttat gttgtagaaa | 1140 |
| atactgtctc atcttttttg cttcgttttc cttaccgttg tgtgttctaa aagacaattt | 1200 |
| tatttgtact actaatattc ttgtgctaat gttactccaa ttttgagtg atccttgtat | 1260 |

<210> SEQ ID NO 10
<211> LENGTH: 294
<212> TYPE: PRT
<213> ORGANISM: Allium cepa

<400> SEQUENCE: 10

```
Met Asp Gln Tyr Glu Lys Val Glu Lys Ile Gly Glu Gly Thr Tyr Gly
1               5                   10                  15
Val Val Tyr Lys Ala Arg Asp Arg Leu Thr Asn Glu Thr Ile Ala Leu
            20                  25                  30
Lys Lys Ile Arg Leu Glu Gln Glu Asp Glu Gly Val Pro Ser Thr Ala
        35                  40                  45
Ile Arg Glu Ile Ser Leu Leu Lys Glu Met Gln His Ala Asn Ile Val
    50                  55                  60
Arg Leu Gln Asp Val Val His Ser Glu Lys Arg Ile Tyr Leu Val Phe
65                  70                  75                  80
Glu Tyr Leu Asp Leu Asp Leu Lys Lys His Met Asp Ser Cys Pro Asp
                85                  90                  95
Phe Ala Lys Asp Ser Arg Leu Ala Lys Thr Phe Leu Tyr Gln Leu Leu
            100                 105                 110
Arg Gly Ile Ala Tyr Cys His Ser His Arg Val Leu His Arg Asp Leu
        115                 120                 125
Lys Pro Gln Asn Leu Leu Ile Asp Arg Arg Thr Asn Ser Leu Lys Leu
    130                 135                 140
Ala Asp Phe Gly Leu Ala Arg Ala Phe Gly Ile Pro Val Arg Thr Phe
145                 150                 155                 160
Thr His Glu Val Val Thr Leu Trp Tyr Arg Ala Pro Glu Ile Leu Leu
                165                 170                 175
Gly Ala Arg Gln Tyr Ser Thr Pro Val Asp Ile Trp Ser Val Gly Cys
            180                 185                 190
Ile Phe Ala Glu Met Val Asn Gln Arg Pro Leu Phe Pro Gly Asp Ser
        195                 200                 205
Glu Ile Asp Glu Leu Phe Lys Ile Phe Arg Ile Met Gly Thr Pro Asn
    210                 215                 220
Glu Asp Thr Trp Pro Gly Val Thr Ser Leu Pro Asp Phe Lys Ser Ala
225                 230                 235                 240
Phe Pro Lys Trp Pro Ala Lys Asp Leu Ala Thr Ile Val Pro Lys Leu
                245                 250                 255
Asp Ser Ala Gly Ile Asp Leu Leu Tyr Lys Met Leu His Leu Glu Pro
            260                 265                 270
Ser Lys Arg Ile Thr Ala Arg Lys Ala Leu Glu His Glu Tyr Phe Arg
        275                 280                 285
Asp Leu Gly Thr Ile Pro
    290
```

<210> SEQ ID NO 11
<211> LENGTH: 1283
<212> TYPE: DNA
<213> ORGANISM: Antirrhinum majus
<220> FEATURE:
<221> NAME/KEY: misc_feature
<222> LOCATION: (1076)..(1076)
<223> OTHER INFORMATION: n is a, c, g, or t

<400> SEQUENCE: 11

```
gtacatggtt tcatctcatc gatctctgat ggagcagtat gaaaaggttg agaagattgg    60
ggagggaacg tatggagtgg tatacaaggc tcgtgatcgt gtaacaaatg agactatagc   120
cttgaagaaa atccgtctag agcaggaaga tgagggagtg cccagcacag ctatcagaga   180
gatttctctc ttgaaagaga tgcaacatgg gaatatcgtg aggttgcagg atgtggtgca   240
```

```
cagtgagaag cgcttgtacc tggtgtttga atatctggac ttggatttga aaaacatat    300 ggattcatgc ccagaattct cccaggatcc tcgtttggtt aaaatgtttc tgtatcaaat    360
actacgtggt atcgcctact gtcattctca tcgtgtcctt catcgagatt tgaagcctca    420
aaacttgctg atagaccgcc gtaccaatgc attaaagctt gctgactttg gattggccag    480
agcatttggt attccagtca ggacttttac acatgaggtt gtgacactgt ggtacagggc    540
tccagaaata ctacttggat ctcgccatta ttctactcca gtggatgtct ggtcagttgg    600
ttgtatattt gctgaaatgg ttaaccaacg gcctttgttt cctggggact ctgagattga    660
tgaactattc aaaattttta gagtcatggg taccccaaat gaagaaacat ggccaggagt    720
gacttctttg cctgatttta agtcagcatt tccaaaatgg ccagctaagg agctggctgc    780
tgtagttccg aatcttgatg catctggcct tgatctcctt gataaaatgc ttcgtttgga    840
ccccagcaaa agaattacgg ccaggaatgc tcttcagcat gagtacttca aggatattgg    900
ttttgtaccc tgattggtgc ccctcattct ggtacgagta tatattgtta tatgacgtct    960
ggggttttat tctgttccat aggaattcgt gacagacgaa cgttatctct tgttttgat   1020 tccttgggtg taattccatt tatattgaag ctgtgttggt tgaagcaagt taggantggc   1080
ctctgctggt gctttcactt gctttaaacc ccttgtgtga ttttgtcgat tttttgttcc   1140
ttttccattt ttaatttccc tgtaacatca tgctgatgta taacgtttga gttttgtta    1200 tctggtttaa tatataaata tggtgtgcct tttagttgtt caaaaaaaaa aaaaaaaaa    1260 aaaaaaccat ggtacccgga tcc                                          1283
```

<210> SEQ ID NO 12
<211> LENGTH: 302
<212> TYPE: PRT
<213> ORGANISM: Antirrhinum majus

<400> SEQUENCE: 12

```
Met Val Ser Ser His Arg Ser Leu Met Glu Gln Tyr Glu Lys Val Glu
1               5                   10                  15

Lys Ile Gly Glu Gly Thr Tyr Gly Val Val Tyr Lys Ala Arg Asp Arg
            20                  25                  30

Val Thr Asn Glu Thr Ile Ala Leu Lys Lys Ile Arg Leu Glu Gln Glu
        35                  40                  45

Asp Glu Gly Val Pro Ser Thr Ala Ile Arg Glu Ile Ser Leu Leu Lys
    50                  55                  60

Glu Met Gln His Gly Asn Ile Val Arg Leu Gln Asp Val Val His Ser
65                  70                  75                  80

Glu Lys Arg Leu Tyr Leu Val Phe Glu Tyr Leu Asp Leu Asp Leu Lys
                85                  90                  95

Lys His Met Asp Ser Cys Pro Glu Phe Ser Gln Asp Pro Arg Leu Val
            100                 105                 110

Lys Met Phe Leu Tyr Gln Ile Leu Arg Gly Ile Ala Tyr Cys His Ser
        115                 120                 125

His Arg Val Leu His Arg Asp Leu Lys Pro Gln Asn Leu Leu Ile Asp
    130                 135                 140

Arg Arg Thr Asn Ala Leu Lys Leu Ala Asp Phe Gly Leu Ala Arg Ala
145                 150                 155                 160

Phe Gly Ile Pro Val Arg Thr Phe Thr His Glu Val Val Thr Leu Trp
                165                 170                 175

Tyr Arg Ala Pro Glu Ile Leu Leu Gly Ser Arg His Tyr Ser Thr Pro
```

```
            180                 185                 190
Val Asp Val Trp Ser Val Gly Cys Ile Phe Ala Glu Met Val Asn Gln
        195                 200                 205

Arg Pro Leu Phe Pro Gly Asp Ser Glu Ile Asp Glu Leu Phe Lys Ile
    210                 215                 220

Phe Arg Val Met Gly Thr Pro Asn Glu Glu Thr Trp Pro Gly Val Thr
225                 230                 235                 240

Ser Leu Pro Asp Phe Lys Ser Ala Phe Pro Lys Trp Pro Ala Lys Glu
                245                 250                 255

Leu Ala Ala Val Val Pro Asn Leu Asp Ala Ser Gly Leu Asp Leu Leu
            260                 265                 270

Asp Lys Met Leu Arg Leu Asp Pro Ser Lys Arg Ile Thr Ala Arg Asn
        275                 280                 285

Ala Leu Gln His Glu Tyr Phe Lys Asp Ile Gly Phe Val Pro
    290                 295                 300

<210> SEQ ID NO 13
<211> LENGTH: 1161
<212> TYPE: DNA
<213> ORGANISM: Antirrhinum majus

<400> SEQUENCE: 13
ggatccgggt accatggagc atatggagtg gtctataagg ctcgtgatat tgaaacaaat      60
gaggatattg ctctcaagaa atccggctg agcaggaag atgagggagt gccaagcacg     120
gctattagag agatttctct tctgaaagaa atgcaccatg agaacattgt gaacttgaag     180
gatgttgtgc accgtgagaa acgtttgtat ctggtatttg aatatctcga cttggactta     240
aagaaacaca tggattcctg cccagaattc tcccaggatc ttcatatggt taaaatgttt     300
ctatgtcaaa tcttacgcgg agttgcctat tgtcattctc atcgcgttct tcatcgagac     360
ttgaagcctc agaacttgct gatagatagg ggtagcaata caataaaact tgcagatttt     420
ggattggcca gagcatttgg tattcctgtc aggacattta cacacgaggt tgtgacacta     480
tggtacaggg ccccagaagt actgcttgga tcacgccatt attctactcc agttgatgtg     540
tggtcagtcg gttgtatatt tgctgaaatg gttaaccaga accattgtt tcctggggat     600 tctgagattg atgaactcca taaaattttt agaatcattg caccccgaa tgaagatata     660 tggcctggag tgacatctct gcctgatttc aaatcatcat ttccaaaatg gccaccaaag     720
gaactggcaa ccatagttcc aaatcttggt gcaactggcc ttgatctcct tgtaaaatg     780 ctacaactag atccaagcaa agaattaca gccaaaaaag ctctggagca tgagtacttt     840
aaggatattg tcttgccctg attagtgccg ctcatcctga tgcaaaaatg taaattggta     900
tgtgccatct ttggttttca ttctgtcaaa tagaattttg tgatatatgg gtgatgcatc     960
tccctttttt gattccctgg gagtaattca attggttctg agcacagcaa tttggagttc    1020
tagcttgctg gtactttgta ttccttcttg tgtgattgtg tcgatatttc cttttgattc    1080
aattttgtcg acttcgtgat aacatcattc tgatgtatga tatatgagct tctgttcctc    1140
ttaatagatt actatggtga a                                              1161

<210> SEQ ID NO 14
<211> LENGTH: 280
<212> TYPE: PRT
<213> ORGANISM: Antirrhinum majus

<400> SEQUENCE: 14
```

Ala Tyr Gly Val Val Tyr Lys Ala Arg Asp Ile Glu Thr Asn Glu Asp
1               5                   10                  15

Ile Ala Leu Lys Lys Ile Arg Leu Glu Gln Glu Asp Glu Gly Val Pro
            20                  25                  30

Ser Thr Ala Ile Arg Glu Ile Ser Leu Lys Glu Met His His Glu
            35                  40                  45

Asn Ile Val Asn Leu Lys Asp Val Val His Arg Glu Lys Arg Leu Tyr
50                  55                  60

Leu Val Phe Glu Tyr Leu Asp Leu Asp Leu Lys Lys His Met Asp Ser
65                  70                  75                  80

Cys Pro Glu Phe Ser Gln Asp Leu His Met Val Lys Met Phe Leu Cys
                85                  90                  95

Gln Ile Leu Arg Gly Val Ala Tyr Cys His Ser His Arg Val Leu His
            100                 105                 110

Arg Asp Leu Lys Pro Gln Asn Leu Leu Ile Asp Arg Gly Ser Asn Thr
            115                 120                 125

Ile Lys Leu Ala Asp Phe Gly Leu Ala Arg Ala Phe Gly Ile Pro Val
130                 135                 140

Arg Thr Phe Thr His Glu Val Val Thr Leu Trp Tyr Arg Ala Pro Glu
145                 150                 155                 160

Val Leu Leu Gly Ser Arg His Tyr Ser Thr Pro Val Asp Val Trp Ser
                165                 170                 175

Val Gly Cys Ile Phe Ala Glu Met Val Asn Gln Lys Pro Leu Phe Pro
            180                 185                 190

Gly Asp Ser Glu Ile Asp Glu Leu His Lys Ile Phe Arg Ile Ile Gly
            195                 200                 205

Thr Pro Asn Glu Asp Ile Trp Pro Gly Val Thr Ser Leu Pro Asp Phe
210                 215                 220

Lys Ser Ser Phe Pro Lys Trp Pro Pro Lys Glu Leu Ala Thr Ile Val
225                 230                 235                 240

Pro Asn Leu Gly Ala Thr Gly Leu Asp Leu Leu Cys Lys Met Leu Gln
                245                 250                 255

Leu Asp Pro Ser Lys Arg Ile Thr Ala Lys Lys Ala Leu Glu His Glu
            260                 265                 270

Tyr Phe Lys Asp Ile Val Leu Pro
            275                 280

<210> SEQ ID NO 15
<211> LENGTH: 1346
<212> TYPE: DNA
<213> ORGANISM: Arabidopsis thaliana

<400> SEQUENCE: 15
ctcaagcttt tcacagaaaa ccaccaccct tctctctcta ctgcctttt accacagaga      60
agagagagga tccgtcggtg tgctagtctc actgacacta catccgatcg tcgccggtga     120
cattttataa gtgtggagtt tacttcagct ttattattca ggaattgatg gatcagtacg     180
agaaagttga gaagattggt gaaggaactt acggtgtggt ttataaggca cgtgacaaag     240
tgactaatga acaattgct ttgaagaaga tcaggctaga gcaggaggat gaaggtgttc      300
ctagcacagc aatcagagaa atctccctct gaaagaaat gcagcatagc aacattgtca     360
aattgcagga tgtggtgcac agcgagaaac gtttgtatct ggtttttgag tatcttgact     420
tggatctcaa aaagcacatg gattctactc ctgattctc caaggatcta catatgatca     480
aaacatatct ttaccagatt ctccgtggaa ttgcgtattg ccactctcat agggttctcc     540

```
atcgtgatct gaagccacag aatttgttga ttgatcgccg cacaaactca ctgaagcttg    600
ctgattttgg actggccaga gcattcggta tccctgtcag gacatttact catgaggttg    660
ttactctctg gtaccgagca ccagagatac tcctaggatc tcatcattac tctacacctg    720
ttgatatttg gtctgtgggg tgcatatttg ctgagatgat cagccaaaag cccttatttc    780
ctggagactc cgagattgat caactcttca agattttcag aatcatggga actccgtacg    840
aggatacatg gcgtggggta acttctctac cggattataa atctgctttc cctaaatgga    900
aaccaacgga cctagaaact tttgtcccca atctagatcc cgatggagtc gatctccttt    960
ctaaaatgct gttaatggat ccgaccaaaa gaatcaacgc aagagccgcc ctggagcatg   1020
aatacttcaa ggatcttgga ggcatgcctt agaaaggcat aaaaccagta atctccttca   1080
ttctatatat aattatcaat cctaagaaaa tgaagaacaa tattaatggg ttttgtttat   1140 tcttttctg agttcgtttc ctacttatat tctattacga aaaaaagaa agaagaagat     1200 ttcgagtgtg tgtgtttttt tacttctaag cttttgagat cagtttcttg tatcttattt   1260
tacccagaat atagtatttc cctatatgaa atatggtttt tgttttgcaa aatgaccata   1320
ttatgcaact tctcagcttc ttgatt                                        1346

<210> SEQ ID NO 16
<211> LENGTH: 294
<212> TYPE: PRT
<213> ORGANISM: Arabidopsis thaliana

<400> SEQUENCE: 16

Met Asp Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ser Asn Ile Val
    50                  55                  60

Lys Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Thr Pro Asp
                85                  90                  95

Phe Ser Lys Asp Leu His Met Ile Lys Thr Tyr Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser His His Tyr Ser Thr Pro Val Asp Ile Trp Ser Val Gly Cys
            180                 185                 190

Ile Phe Ala Glu Met Ile Ser Gln Lys Pro Leu Phe Pro Gly Asp Ser
        195                 200                 205

Glu Ile Asp Gln Leu Phe Lys Ile Phe Arg Ile Met Gly Thr Pro Tyr
    210                 215                 220
```

-continued

```
Glu Asp Thr Trp Arg Gly Val Thr Ser Leu Pro Asp Tyr Lys Ser Ala
225                 230                 235                 240

Phe Pro Lys Trp Lys Pro Thr Asp Leu Glu Thr Phe Val Pro Asn Leu
            245                 250                 255

Asp Pro Asp Gly Val Asp Leu Leu Ser Lys Met Leu Leu Met Asp Pro
        260                 265                 270

Thr Lys Arg Ile Asn Ala Arg Ala Leu Glu His Glu Tyr Phe Lys
    275                 280                 285

Asp Leu Gly Gly Met Pro
        290

<210> SEQ ID NO 17
<211> LENGTH: 353
<212> TYPE: DNA
<213> ORGANISM: Beta vulgaris

<400> SEQUENCE: 17
ttggtgaggg aacttatggt gtggtctata aggcgcggga caaggttacg aatgagacta     60
tagctttgaa gaaatccgg ttggagcagg aggatgaagg agttccgagc acggcgatca    120
gagaaatctc cctcttgaag gagatgcagc atggcaacat tgtcaggttg caggatgtag    180
tgcacagtga aagcgcttg tatttggttt tgagtattt ggacctagac ttaaagaaac     240
acatggattc atcccctgat tttgcaaagg atccacgtat gattaaaagg tttctttatc    300
aaattcttcg tggtatagca tattgtcact ctcatcgtgt cctgcatcgc gac           353

<210> SEQ ID NO 18
<211> LENGTH: 117
<212> TYPE: PRT
<213> ORGANISM: Beta vulgaris

<400> SEQUENCE: 18

Gly Glu Gly Thr Tyr Gly Val Val Tyr Lys Ala Arg Asp Lys Val Thr
1               5                   10                  15

Asn Glu Thr Ile Ala Leu Lys Lys Ile Arg Leu Glu Gln Glu Asp Glu
            20                  25                  30

Gly Val Pro Ser Thr Ala Ile Arg Glu Ile Ser Leu Leu Lys Glu Met
        35                  40                  45

Gln His Gly Asn Ile Val Arg Leu Gln Asp Val Val His Ser Glu Lys
    50                  55                  60

Arg Leu Tyr Leu Val Phe Glu Tyr Leu Asp Leu Asp Leu Lys Lys His
65                  70                  75                  80

Met Asp Ser Ser Pro Asp Phe Ala Lys Asp Pro Arg Met Ile Lys Arg
                85                  90                  95

Phe Leu Tyr Gln Ile Leu Arg Gly Ile Ala Tyr Cys His Ser His Arg
            100                 105                 110

Val Leu His Arg Asp
        115

<210> SEQ ID NO 19
<211> LENGTH: 1240
<212> TYPE: DNA
<213> ORGANISM: Brassica napus

<400> SEQUENCE: 19
tataaactgc cttttcatcc agagagtgag gatccgtcgg tgtcactaca tccgatcgtc     60
gccggtgacg tgtttcagcc tagtttaatc ttggaagtga tggatcagta cgagaaagtt    120
```

```
gagaagatcg gcgaaggaac ttacggtgtt gtgtacaagg cacgagacaa ggtcaccaat      180
gagactattg ctttgaagaa gatccgcctc gagcaggagg atgaaggtgt tcctagcact      240
gccattagag aaatctctct tttgaaggaa atgcagcaca gcaacattgt caagctgcag      300
gatgtagtgc acagcgagaa gcgtttgtat cttgttttcg agtatcttga cttggatctc      360
aaaaagcaca tggactcttc tcctgatttc tccaaggatc ttcatatgat caaaaggtat      420
gtttaccaga ttctccgtgg aatcgcgtat tgccactctc acagggttct ccatcgtgac      480
ctcaagccac agaatttgtt gattgatcgc cgcaccaact cactaaagct tgctgatttt      540
ggactggcca gagctttcgg tatccctgtc aggacttta ctcatgaggt ggttactctc       600
tggtaccgag caccagagat acttctaggg tctcatcact actctacacc ggttgatatt      660
tggtctgtgg gatgcatatt tgccgagatg atcagccaaa agcccttgtt cctggagac       720 tccgagattg atcaactctt caagatattc agaatcatgg aactccaac ggaggataca       780 tggcctgggg taacttcgct gccggattat aaatctgctt tcccaaaatg gaaaccaacg      840
gacttggaat cttttgtccc aaacctggat cctaatggca tagatctcct ttctaaaatg      900
ctgttgatga tccaaccaa agaatcaac gcaagagccg ccctggagca tgattacttc        960
aaggatattg gcgtcatgcc gtagagaatg cttcaaaacc agtagtctcc tacattctct     1020
ctatatatat aagtaattcg atatcttcca tcctaagaaa acgaggttaa atacatcaat     1080 ggttttgtt tattcttttg atttctttta agtttgttat tctctgatac gaaaaatgga       1140
aaagatttag agtgtgcttt gtttattct tctaagcttt tgagatcatt ttcttgtgta       1200 tcttttacc aagttcagta atgtatggta tttattttgc                            1240

<210> SEQ ID NO 20
<211> LENGTH: 294
<212> TYPE: PRT
<213> ORGANISM: Brassica napus

<400> SEQUENCE: 20

Met Asp Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ser Asn Ile Val
    50                  55                  60

Lys Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Asp
                85                  90                  95

Phe Ser Lys Asp Leu His Met Ile Lys Arg Tyr Val Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175
```

```
Gly Ser His His Tyr Ser Thr Pro Val Asp Ile Trp Ser Val Gly Cys
            180                 185                 190

Ile Phe Ala Glu Met Ile Ser Gln Lys Pro Leu Phe Pro Gly Asp Ser
        195                 200                 205

Glu Ile Asp Gln Leu Phe Lys Ile Phe Arg Ile Met Gly Thr Pro Thr
    210                 215                 220

Glu Asp Thr Trp Pro Gly Val Thr Ser Leu Pro Asp Tyr Lys Ser Ala
225                 230                 235                 240

Phe Pro Lys Trp Lys Pro Thr Asp Leu Glu Ser Phe Val Pro Asn Leu
                245                 250                 255

Asp Pro Asn Gly Ile Asp Leu Leu Ser Lys Met Leu Leu Met Asp Pro
            260                 265                 270

Thr Lys Arg Ile Asn Ala Arg Ala Ala Leu Glu His Asp Tyr Phe Lys
        275                 280                 285

Asp Ile Gly Val Met Pro
    290
```

<210> SEQ ID NO 21
<211> LENGTH: 1274
<212> TYPE: DNA
<213> ORGANISM: Chenopodium rubrum

<400> SEQUENCE: 21

```
tatttctatc ctccattgaa gcagtttctg agtggtagag atacgggacg aaatggatca      60
gtatgaaaaa gttgagaaga taggggaagg aacctatgga gtggtttata aggcgcggga     120
caaggttacg aacgagacta tagctttgaa gaaaattcgg ttggaacagg aggatgaggg     180
agttccgagc acggcgatca gagaaatatc acttttgaag gagatgcagc atggcaacat     240
tgtcaggttg caggatgtgg tgcatagtga gaagcgctta tatctggttt ttgagtattt     300
ggaccttgat ttgaagaaac acatggattc atgccctgat tttgcaaagg atccacgtat     360
gattaaaagg tttctttatc agattcttcg tggtatcgct tattgtcact ctcataggt      420
cctgcaccga gatctgaagc cgcagaatct gttgatagat cgccaaacta atgcactaaa     480
acttgcagat tttggattgg caagggcatt tggtattcct gtgaggactt ttacacatga     540
ggtggtgaca ttgtgtacag agctccagaa atattgctt ggatctcgac attactctac      600
tcctgtggat gtgtggtctg tgggttgtat ctttgctgag atggtgaatc agaagccatt     660
atttcctgga gattccgaga ttgatgaact tttcaagatt tcaggacct tgggtacacc       720
aaatgaggag acatggcctg gagtgacctc ccttcccgat ttcaaatctt catttcctaa     780
atggatctcc aaggatttgt ctgcagtagt accaaatctt gatccagctg gtattgatct     840
tctaaataaa atgctttgct ggatccgag caaaaggatt acagccagga atgctcttga      900
acatgaatac ttcaaggaca ttggttttgt accctgatt ctgttcatcg ccttccaggt       960
tatctcgtgt gaatattgga agttaaggaa aaaagattct gttgatttat tttccgcggg    1020
tgaaatgtgt gcaattgttg tagatttttt ttgatgctat gcttaccatt gttctttgcc    1080
aggacttcat gtcgtgtaat tgactgttct gcattgggat tgagaacttt gtgaagcccc    1140
attgcgatgt gcaaattata cccgtcttcc atatcactcc taaattgctt gaatgtgacc    1200
catctatggg cttctattat ttaatcaaga ttgattttt ctattgcaaa aaaaaaaaa       1260
aaaaaaact cgag                                                       1274
```

<210> SEQ ID NO 22
<211> LENGTH: 294

```
<212> TYPE: PRT
<213> ORGANISM: Chenopodium rubrum

<400> SEQUENCE: 22

Met Asp Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Asp
                85                  90                  95

Phe Ala Lys Asp Pro Arg Met Ile Lys Arg Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Gln Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Thr Leu Gly Thr Pro Asn
    210                 215                 220

Glu Glu Thr Trp Pro Gly Val Thr Ser Leu Pro Asp Phe Lys Ser Ser
225                 230                 235                 240

Phe Pro Lys Trp Ile Ser Lys Asp Leu Ser Ala Val Val Pro Asn Leu
                245                 250                 255

Asp Pro Ala Gly Ile Asp Leu Leu Asn Lys Met Leu Cys Leu Asp Pro
            260                 265                 270

Ser Lys Arg Ile Thr Ala Arg Asn Ala Leu Glu His Glu Tyr Phe Lys
        275                 280                 285

Asp Ile Gly Phe Val Pro
    290

<210> SEQ ID NO 23
<211> LENGTH: 1216
<212> TYPE: DNA
<213> ORGANISM: Glycine max

<400> SEQUENCE: 23
cgcttacagt aagaggtgag aaagagagac aaatcggcag aagcaaggag gctgagagcg      60
agagagcaac tgcacgcact gtaactccta acttcccaga tcgtcttctt cctcttttct     120
ctccggtgat tgttggaact cagagagctt ctttgatgga acagtacgag aaggttgaga     180
agataggcga aggaacatac ggcgtcgttt acaagggtcg cgaccgcgtc accaacgaga     240
ccatcgcgtt gaagaagatt cgcctcgagc aggaggatga gggggttccc agcaccgcca     300
```

```
ttcgcgagat ttctctcttg aaagaaatgc agcacaggaa cattgttagg ttgcaggatg      360
tagtgcacga tgagaagagt ttgtatctgg tttttgagta ccttgactta gatctaaaga      420
agcacatgga ttcatctcca gaatttgcaa aagatccacg acaagtaaaa atgttcctgt      480
accaaattct ctgtggcatt gcatactgtc attcacatag agttcttcat cgagacttaa      540
aaccacagaa tttgttgata gatcgcagca ctaatgcact gaaacttgca gattttggat      600
tggccagggc ttttggaatt cctgttagga catttacaca tgaggtggta acactgtggt      660
acagagctcc ggaaattttg cttggatccc gtcagtattc tacccagtt gatatttggt       720 cagtgggatg catatttgca gagatggtaa atcaacgacc acttttccct ggggactctg      780
agattgatga attgtttaaa atattcagaa tcatgggtac accaaatgaa gatacatggc      840
ctggagtgac atcattgcca gattttaaat cagccttccc caaatggcaa cctaaggacc      900
tgaaaaatgt ggttccaaat cttgagccag ctggtcttga tcttctttct agcatgcttt      960
acttggatcc cagcaaaaga attactgcta ggagcgctct tgagcatgaa tacttcaaag     1020
acattaaatt tgtaccctga tttcttatct tcaaggctga ggtgtcttat tagtatgtgt     1080
agcatttatg ggttttgact caaacgcgtg ttgtccttgc ttttttcttc aatgcttttg     1140
gaccgaatca tatttcattt atttgttctt acatttttat ttagtatgtg tgatcttgtt     1200
acctatttac ccgttt                                                     1216

<210> SEQ ID NO 24
<211> LENGTH: 294
<212> TYPE: PRT
<213> ORGANISM: Glycine max

<400> SEQUENCE: 24

Met Glu Gln Tyr Glu Lys Val Glu Lys Ile Gly Glu Gly Thr Tyr Gly
1               5                   10                  15

Val Val Tyr Lys Gly Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Asp Glu Lys Ser Leu Tyr Leu Val Phe
65                  70                  75                  80

Glu Tyr Leu Asp Leu Asp Leu Lys Lys His Met Asp Ser Ser Pro Glu
                85                  90                  95

Phe Ala Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Ser Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg Gln Tyr Ser Thr Pro Val Asp Ile Trp Ser Val Gly Cys
            180                 185                 190

Ile Phe Ala Glu Met Val Asn Gln Arg Pro Leu Phe Pro Gly Asp Ser
        195                 200                 205
```

Glu Ile Asp Glu Leu Phe Lys Ile Phe Arg Ile Met Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Gln Pro Lys Asp Leu Lys Asn Val Val Pro Asn Leu
                245                 250                 255

Glu Pro Ala Gly Leu Asp Leu Leu Ser Ser Met Leu Tyr Leu Asp Pro
                260                 265                 270

Ser Lys Arg Ile Thr Ala Arg Ser Ala Leu Glu His Glu Tyr Phe Lys
        275                 280                 285

Asp Ile Lys Phe Val Pro
    290

<210> SEQ ID NO 25
<211> LENGTH: 1157
<212> TYPE: DNA
<213> ORGANISM: Glycine max

<400> SEQUENCE: 25

```
aattcggcac gaggtggagt gagagatagt gactgcaaaa ccgctccagc cttgtttctt      60
ctcagatctt cttccatgga acagtacgag aaggtggaga agataggcga gggaacatac     120
ggcgtcgttt acaaggctcg cgaccgcgtc accaatgaga ccatcgctct caagaagatt     180
cgcctcgagc aggaggacga aggcgttccc agcaccgcca ttcgcgagat ttctctcctc     240
aaagagatgc agcataggaa cattgttagg ttgcaggatg tagtacacag tgagaagcga     300
ttgtatctgg tttttgagta tctggacttg gatctaaaga aacatatgga ttcatctcca     360
gagtttgtga aagatccacg gcaagtaaag atgttccttt atcaaattct ctgtggcatt     420
gcttactgtc attcacatag agttcttcat cgagacttga aaccacagaa tttgttgata     480
gatcgccgta ctaattcact aaagcttgca gattttggat tggctagggc atttggcatt     540
cctgtcagga catttacaca tgaggtggtg acattatggt acagagctcc agaaatattg     600
cttggatctc gtcattattc tacgccagtt gatgtttggt cagtgggatg tatatttgca     660
gagatggtaa accgacgacc tctattccct ggggactctg agattgatga attatttaaa     720
atattcagaa tcttgggtac cccaaatgaa gacacatggc ctggtgtaac ttcattgcct     780
gattttaaat caacatttcc caaatggcca tccaaggact tggcaaatgt ggttccaaat     840
cttgatgcag ctggtcttaa tcttctttct agtatgcttt gcttggatcc agcaaaaga     900
atcaccgcca ggagcgctgt ggagcatgaa tacttcaaag acattaaatt tgttccctga     960
ttccatatct tgatggcaaa cgtgtttata gtaatattgt gcagaattta tgggttttga    1020
ctctgcgaga aatgcgtgct gtcttttttct attttcttag tgacttggga gtgtgagcca    1080
tatttccatt ttttggtcct tacagaatgt tcagattca acttgagtgt gattatattg    1140
catattactt tttcatt                                                   1157
```

<210> SEQ ID NO 26
<211> LENGTH: 294
<212> TYPE: PRT
<213> ORGANISM: Glycine max

<400> SEQUENCE: 26

Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu

```
                20                  25                  30
Lys Lys Ile Arg Leu Glu Gln Glu Asp Glu Gly Val Pro Ser Thr Ala
             35                  40                  45

Ile Arg Glu Ile Ser Leu Leu Lys Glu Met Gln His Arg Asn Ile Val
 50                  55                  60

Arg Leu Gln Asp Val Val His Ser Glu Lys Arg Leu Tyr Leu Val Phe
 65                  70                  75                  80

Glu Tyr Leu Asp Leu Asp Leu Lys Lys His Met Asp Ser Ser Pro Glu
                 85                  90                  95

Phe Val Lys Asp Pro Arg Gln Val Lys Met Phe Leu Tyr Gln Ile Leu
                100                 105                 110

Cys Gly Ile Ala Tyr Cys His Ser His Arg Val Leu His Arg Asp Leu
                115                 120                 125

Lys Pro Gln Asn Leu Leu Ile Asp Arg Arg Thr Asn Ser Leu Lys Leu
                130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
                180                 185                 190

Ile Phe Ala Glu Met Val Asn Arg Arg Pro Leu Phe Pro Gly Asp Ser
                195                 200                 205

Glu Ile Asp Glu Leu Phe Lys Ile Phe Arg Ile Leu Gly Thr Pro Asn
                210                 215                 220

Glu Asp Thr Trp Pro Gly Val Thr Ser Leu Pro Asp Phe Lys Ser Thr
225                 230                 235                 240

Phe Pro Lys Trp Pro Ser Lys Asp Leu Ala Asn Val Val Pro Asn Leu
                245                 250                 255

Asp Ala Ala Gly Leu Asn Leu Leu Ser Ser Met Leu Cys Leu Asp Pro
                260                 265                 270

Ser Lys Arg Ile Thr Ala Arg Ser Ala Val Glu His Glu Tyr Phe Lys
                275                 280                 285

Asp Ile Lys Phe Val Pro
    290

<210> SEQ ID NO 27
<211> LENGTH: 1457
<212> TYPE: DNA
<213> ORGANISM: Lycopersicon esculentum

<400> SEQUENCE: 27
ttgactgtag tccaaacatt ttggtaacac cgtagaagta cgccgacact tgcctgtcgc      60 ctcctcccccg cttcacgaac ggcgatttcg tcctcttttc ccgaccaaag ggagtccatt    120
gagtttgaaa tagatggacc agtatgaaaa agttgagaag attggggaag gaacatatgg    180
tgtagtgtac aaggctcgtg atcgtgtaac taatgaaact attgcactga agaaaataag    240
gttggagcag gaagacgagg gggtaccaag cacagctatt agagaaatat ctctcttgaa    300
agagatgcaa catgctaata ttgtgaggtt gcaggatgtg gtgcacagtg aaaagcgatt    360
gtatctagtg tttgaatatc ttgacttgga cttgaagaag cacatggatt cgtgtcctga    420
attctctaag gatccacgtc tggttaaaat gttcttgtat caaatactcc gtggtattgc    480
ttattgtcat tctcatagag ttcttcatag agatttgaag cctcagaact tactaataga    540
```

-continued

```
tcgacgtaca aatgctttaa agctggcaga cttttggtttg gctagagcat ttggtattcc   600
tgtcagaact ttcactcatg aggtggtgac attgtgtac agggcaccag aaatactgct    660
tggatcacgc cattactcta ctcctgttga tgtgtggtca gttggttgca tatttgctga   720
gatggtgaat cagccgcctc tgtttcctgg tgactctgag attgatgaac ttttcaagat   780
tttcagagta ttgggtactc caaatgagga tacatggcct ggagtgactt ctctgcctga   840
ttacaaatct gccttcccaa aatggcctcc taaggacctg gcaattattg taccaaatgt   900
tgatggagca ggccttgatc ttcttggtaa aatgctctcc ttggatccca gtaagagaat   960
caccgcgagg aatgcccttg agcatgagta cttcaaggat attgggtatg tgccgtgatt  1020
gtctgcccct tcatccagaa tgctattgta aatttggtat gtcatctaca ggttttgttc  1080
tggagaatct gtgtgatctt taggccttt tggcccctca aagttttatt ccattgtgta   1140
tcctgttcca gcacatgtgg tcacaattcg tgtccacatg ttgtagtata ctttcccgtg  1200
taatatccat ttggttctat tcaggggttc agtatccttg tacaacgaat gcttatttag  1260
atacaacaat ggatactgta atgttaaata gattggattt ggtgtgtcaa ttagaagttt  1320
tgcatagttt tgcctggagt ggaacaaagc ttgagtgat tgtccgactc ctaggttatg   1380
ccagtgcatt tcttgatgac gcaggctggt tatatcaagt tctatttga tgttaaaaaa   1440
aaaaaaaaaa aaaaaaa                                                  1457
```

<210> SEQ ID NO 28
<211> LENGTH: 294
<212> TYPE: PRT
<213> ORGANISM: Lycopersicon esculentum

<400> SEQUENCE: 28

```
Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Pro Pro Leu Phe Pro Gly Asp Ser
        195                 200                 205
```

```
Glu Ile Asp Glu Leu Phe Lys Ile Phe Arg Val Leu Gly Thr Pro Asn
    210                 215                 220
Glu Asp Thr Trp Pro Gly Val Thr Ser Leu Pro Asp Tyr Lys Ser Ala
225                 230                 235                 240
Phe Pro Lys Trp Pro Lys Asp Leu Ala Ile Ile Val Pro Asn Val
                245                 250                 255
Asp Gly Ala Gly Leu Asp Leu Leu Gly Lys Met Leu Ser Leu Asp Pro
            260                 265                 270
Ser Lys Arg Ile Thr Ala Arg Asn Ala Leu Glu His Glu Tyr Phe Lys
        275                 280                 285
Asp Ile Gly Tyr Val Pro
    290
```

<210> SEQ ID NO 29
<211> LENGTH: 1176
<212> TYPE: DNA
<213> ORGANISM: Lycopersicon esculentum

<400> SEQUENCE: 29

| | | | | | |
|---|---|---|---|---|---|
| tccgtcttcc | gccagtaccg | ccggcagctt | ttcatctccg | atcctccggt | tcacgaacgg | 60 |
| cgatatcctt | ctctagacat | actcaagagt | ccatccagtt | tgacctaatg | catggaccag | 120 |
| tatgaaaaag | ttgaaaagat | tggtgaagga | acgtacggcg | tagtgtacaa | agctcgtgat | 180 |
| cgtgtaacta | atgaaactat | tgcactgaag | aaaattcggc | tggagcagga | agacgagggt | 240 |
| gtgccaagca | cggctattag | agaaatctcc | ctcttgaaag | agatgcagca | tggaaacatt | 300 |
| gtgaggttgc | aagatgtggt | tcacagtgag | aagcgattat | atctagtgtt | tgaatatctc | 360 |
| gacttggatt | tgaagaagca | tatggactca | tgtcctgagt | tctctaagga | tccgcgtctg | 420 |
| gtaaaaatgt | ttttgtatca | aattctccgt | ggaattgctt | attgtcattc | tcatagagtt | 480 |
| cttcaccgag | acttgaagcc | tcagaacttg | ctgatagata | cgtacaaa | cgttctaaag | 540 |
| cttgcagact | ttggattggc | tagagcattc | ggcattcctg | tcagaacttt | cacccacgag | 600 |
| gtggtgacgt | tatggtacag | ggcaccagaa | atactgctag | gatcacgcca | ctactctact | 660 |
| cctgttgatg | tttggtcagt | aggctgcata | tttgctgaga | tggtgaacca | gcggcctctg | 720 |
| tttcctggtg | actccagat | tgacgaactt | tcaagatttt | cagagttgt | cggtactcca | 780 |
| aatgaggata | catggcctgg | agtgacttct | ttgcctgatt | ttaaatctgc | ttttccaaag | 840 |
| tggccatcta | aggacttagg | aactgtagta | cctaatcttg | gtgcagcagg | ccttgatctc | 900 |
| attggtaaaa | tgcttacctt | agaccccagc | aagagaatca | ctgcccgaag | cgcccttgag | 960 |
| catgagtact | tcaaggacat | tgggttcgta | ccatgaatcg | aggcacctgc | atcttcagtt | 1020 |
| ctaatgtata | tttgagtgtg | ttattttag | gctttatttg | tcctctactt | ttaattatat | 1080 |
| ttcctccaat | gacatccaat | ctgtttacga | ttcacgctag | atgtttgaag | atagtttcac | 1140 |
| tgcaaaaaaa | aaaaaaaaa | aaaaaaaaa | aaaaaa | | | 1176 |

<210> SEQ ID NO 30
<211> LENGTH: 294
<212> TYPE: PRT
<213> ORGANISM: Lycopersicon esculentum

<400> SEQUENCE: 30

```
Met Asp Gln Tyr Glu Lys Val Glu Lys Ile Gly Glu Gly Thr Tyr Gly
1               5                   10                  15
Val Val Tyr Lys Ala Arg Asp Arg Val Thr Asn Glu Thr Ile Ala Leu
            20                  25                  30
```

```
Lys Lys Ile Arg Leu Glu Gln Glu Asp Glu Gly Val Pro Ser Thr Ala
             35                  40                  45

Ile Arg Glu Ile Ser Leu Leu Lys Glu Met Gln His Gly Asn Ile Val
 50                  55                  60

Arg Leu Gln Asp Val Val His Ser Glu Lys Arg Leu Tyr Leu Val Phe
 65                  70                  75                  80

Glu Tyr Leu Asp Leu Asp Leu Lys Lys His Met Asp Ser Cys Pro Glu
                 85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Val Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Val Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Pro Ser Lys Asp Leu Gly Thr Val Val Pro Asn Leu
                245                 250                 255

Gly Ala Ala Gly Leu Asp Leu Ile Gly Lys Met Leu Thr Leu Asp Pro
            260                 265                 270

Ser Lys Arg Ile Thr Ala Arg Ser Ala Leu Glu His Glu Tyr Phe Lys
        275                 280                 285

Asp Ile Gly Phe Val Pro
        290

<210> SEQ ID NO 31
<211> LENGTH: 998
<212> TYPE: DNA
<213> ORGANISM: Medicago sativa

<400> SEQUENCE: 31
gggcgaaaat gtggagaaga ttggtgaagg aacatacggc gtcgtttaca aggcacgtga      60
ccgtgtaacg aatgaaacca tcgcgttgaa gaagattcga cttgaacagg aagatgaagg     120
tgttcctagc actgccattc gtgagatttc gctgcttaaa gaaatgcagc ataggaacat     180
cgttaggttg caggatgtag tgcacagtga caagcgattg tatctggttt ttgagtatct     240
ggacttagat ctgaagaagc atatggattc atctcctgag tttataaaag atccgcgaca     300
agtaaaaatg ttcctttatc aaatgctctg tggaattgct actgtcatt cacacagagt      360 tcttcatcga gacttgaaac cacagaattt ggttgatagat cgccgtacta attcacttaa     420
gcttgccgat tttggattgg ccagggcatt tggtattcct gtcagaacat tacacatga      480 ggtagttaca ctgtggtacc gagctccgga aatattgctt ggatctcgtc attattctac     540
cccagttgat gtttggtcag tgggatgtat atttgcagag atggcaaatc ggcgacctct     600
```

-continued

```
atcccctggg gattccgaga ttgatgagtt atttaaaata ttcagaatct tgggtacacc      660
aaatgaagat acatggccag gagtaacttc attgcctgat tttaaatcaa catttcccag      720
gtggccatct aaggacctag caaccgtggt tccaaatctt gagccagctg gtcttgatct      780
tcttaatagc atgctttgct tggatcccac caaaagaatt actgccagga gcgctgtgga      840
gcatgaatat ttcaaagaca ttaagtttgt accctaattc tataatctat atcttaatgg      900
taaaggtgtt tatagcaata tgtgcagaat ttatggattt tgattgtgcc agaaatgggt      960
gtgttatttt tgctactttc ttcaaagacc taggatcc                              998
```

<210> SEQ ID NO 32
<211> LENGTH: 291
<212> TYPE: PRT
<213> ORGANISM: Medicago sativa

<400> SEQUENCE: 32

```
Gly Glu Asn Val Glu Lys Ile Gly Glu Gly Thr Tyr Gly Val Val Tyr
 1               5                  10                  15

Lys Ala Arg Asp Arg Val Thr Asn Glu Thr Ile Ala Leu Lys Lys Ile
            20                  25                  30

Arg Leu Glu Gln Glu Asp Glu Gly Val Pro Ser Thr Ala Ile Arg Glu
        35                  40                  45

Ile Ser Leu Leu Lys Glu Met Gln His Arg Asn Ile Val Arg Leu Gln
    50                  55                  60

Asp Val Val His Ser Asp Lys Arg Leu Tyr Leu Val Phe Glu Tyr Leu
65                  70                  75                  80

Asp Leu Asp Leu Lys Lys His Met Asp Ser Ser Pro Glu Phe Ile Lys
                85                  90                  95

Asp Pro Arg Gln Val Lys Met Phe Leu Tyr Gln Met Leu Cys Gly Ile
            100                 105                 110

Ala Tyr Cys His Ser His Arg Val Leu His Arg Asp Leu Lys Pro Gln
        115                 120                 125

Asn Leu Leu Ile Asp Arg Arg Thr Asn Ser Leu Lys Leu Ala Asp Phe
    130                 135                 140

Gly Leu Ala Arg Ala Phe Gly Ile Pro Val Arg Thr Phe Thr His Glu
145                 150                 155                 160

Val Val Thr Leu Trp Tyr Arg Ala Pro Glu Ile Leu Leu Gly Ser Arg
                165                 170                 175

His Tyr Ser Thr Pro Val Asp Val Trp Ser Val Gly Cys Ile Phe Ala
            180                 185                 190

Glu Met Ala Asn Arg Arg Pro Leu Ser Pro Gly Asp Ser Glu Ile Asp
        195                 200                 205

Glu Leu Phe Lys Ile Phe Arg Ile Leu Gly Thr Pro Asn Glu Asp Thr
    210                 215                 220

Trp Pro Gly Val Thr Ser Leu Pro Asp Phe Lys Ser Thr Phe Pro Arg
225                 230                 235                 240

Trp Pro Ser Lys Asp Leu Ala Thr Val Val Pro Asn Leu Glu Pro Ala
                245                 250                 255

Gly Leu Asp Leu Leu Asn Ser Met Leu Cys Leu Asp Pro Thr Lys Arg
            260                 265                 270

Ile Thr Ala Arg Ser Ala Val Glu His Glu Tyr Phe Lys Asp Ile Lys
        275                 280                 285

Phe Val Pro
    290
```

<210> SEQ ID NO 33
<211> LENGTH: 1308
<212> TYPE: DNA
<213> ORGANISM: Medicago sativa

<400> SEQUENCE: 33

```
cacggcgcgc tgtctgtgta accgtttctc tgaatttcaa catcgctttg aactttaagc      60
gttttttga tggaacagta cgagaaagtt gagaagatag gagaaggtac ttacggtgtg      120
gtttacaagg ctcgtgaccg tgctaccaat gagacgatag cttttgaagaa gattcgtctt     180
gagcaggaag atgagggagt tccgagtacc gctattcgag agatttctct cttgaaggaa     240
atgcagcaca ggaacattgt taggttgcag gatgtggtgc acagtgagaa gcgattgtat     300
ctggttttg agtaccttga cttggatcta aagaagttta tggattcatc tccagaattt     360
gcaaaagatc aacggcaaat aaagatgttc ctttatcaaa ttctctgtgg cattgcttac     420
tgtcattctc atagagttct tcatagagac ttgaaaccac agaatctgct gattgatcgc     480
agctctaatg ccgtaaagct tgcagatttt ggattggcca gggcatttgg aattcctgtc     540
aggacattta cacatgaggt ggtgacactc tggtacagag ctccagaaat attgcttggg     600
tctcgtcatt attctacccc ggttgatgtc tggtcagtgg gatgcatatt tgcagagatg     660
ataaaccaac ggccactttt cccaggggac tctgagattg atgaattgtt taaaatattc     720
agaatcacgg gtacaccgaa tgaggaaaca tggcctggag tgacttcatt gcctgatttt     780
aaatcagcct ttcccaagtg gccagctaag gacctggcaa ctcaagtccc aaatctggag     840
ccagctggtc ttgatcttct atccagtact tgtcgcttgg atcccaccag aagaattact     900
gccagggag ctcttgagca tgaatacttc aaagacatta gtttgtccc atgagttctt     960
ggcttcacgg aagaggtgtc tatattattg tgtgtatcat ttatgggttt tgactcagaa     1020
atgggtgcta tccttggtat tttcttcaat gcttggactg agtaatattt aatttattgg     1080
ttcttggatt ttttttagat tcagcttgag tgtgatcata ctgcctatta cctttttaa     1140
tgtcttagtc tcagtacaat gcaaccagca aatttcctgt ttgattgatg tataatatta     1200
atagacattg ttgaatggtg gttgtagaac aaatgttact cctactggca tggagcatgt     1260
aaatttgaca tccgttcatg tctataagtt ggttttaaaa aaaaaaaa                  1308
```

<210> SEQ ID NO 34
<211> LENGTH: 294
<212> TYPE: PRT
<213> ORGANISM: Medicago sativa

<400> SEQUENCE: 34

```
Met Glu Gln Tyr Glu Lys Val Glu Lys Ile Gly Glu Gly Thr Tyr Gly
1               5                   10                  15

Val Val Tyr Lys Ala Arg Asp Arg Ala Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys Phe Met Asp Ser Ser Pro Glu
                85                  90                  95
```

-continued

```
Phe Ala Lys Asp Gln Arg Gln Ile Lys Met Phe Leu Tyr Gln Ile Leu
                100                 105                 110
Cys Gly Ile Ala Tyr Cys His Ser His Arg Val Leu His Arg Asp Leu
            115                 120                 125
Lys Pro Gln Asn Leu Leu Ile Asp Arg Ser Ser Asn Ala Val Lys Leu
        130                 135                 140
Ala Asp Phe Gly Leu Ala Arg Ala Phe Gly Ile Pro Val Arg Thr Phe
145                 150                 155                 160
Thr His Glu Val Val Thr Leu Trp Tyr Arg Ala Pro Glu Ile Leu Leu
                165                 170                 175
Gly Ser Arg His Tyr Ser Thr Pro Val Asp Val Trp Ser Val Gly Cys
            180                 185                 190
Ile Phe Ala Glu Met Ile Asn Gln Arg Pro Leu Phe Pro Gly Asp Ser
        195                 200                 205
Glu Ile Asp Glu Leu Phe Lys Ile Phe Arg Ile Thr Gly Thr Pro Asn
    210                 215                 220
Glu Glu Thr Trp Pro Gly Val Thr Ser Leu Pro Asp Phe Lys Ser Ala
225                 230                 235                 240
Phe Pro Lys Trp Pro Ala Lys Asp Leu Ala Thr Gln Val Pro Asn Leu
                245                 250                 255
Glu Pro Ala Gly Leu Asp Leu Leu Ser Ser Thr Cys Arg Leu Asp Pro
            260                 265                 270
Thr Arg Arg Ile Thr Ala Arg Gly Ala Leu Glu His Glu Tyr Phe Lys
        275                 280                 285
Asp Ile Lys Phe Val Pro
    290
```

<210> SEQ ID NO 35
<211> LENGTH: 1379
<212> TYPE: DNA
<213> ORGANISM: Nicotiana tabacum

<400> SEQUENCE: 35

```
cacgagcctc tatgcaaata gaagcaaaag aagagtattg actgtagtcc aaacattttg      60
gtacgagtac gccgacactt gcctgtcgcc tcctcctccg cttcacgaac cgcgatttag     120
tcctcttttt tcgatcaaag ggagttcatt gagtttgact agatggacca gtatgaaaaa     180
gttgagaaga ttggggaagg aacatacggt gtagtgtaca aggctcgtga tcgtgtaact     240
aatgaaacaa ttgcgctgaa gaaaataagg ctggagcagg aagatgaggg agtaccaagc     300
acagctatta gagaaatctc tcttttgaaa gagatgcagc atgctaatat tgtgaggttg     360
caggatgttg tgcacagtga aaagcgattg tatctagttt ttgaatatct tgacttggac     420
ttgaagaagc acatggattc atctcctgaa ttctctaagg atccacgtct ggttaaaatg     480
tttttgtatc aaatactccg tggtattgct tattgtcatt ctcatagagt tcttcatcga     540
gatttgaagc ctcaaaactt gctgatagat cgacgtacaa atgctttaaa gcttgcagac     600
tttggattgg ctagagcatt tggtattcct gtcagaactt tcactcatga ggtggtgaca     660
ttgtggtaca gggcaccaga aatactgctg gtacacgcc attattctac tcctgttgat      720
gtgtggtcag ttggttgcat atttgctgag atggtgactc agcgccctct gtttcctggt     780
gactccgaga ttgatgaact tttcaagatt ttcagagtga tgggtactcc aaatgaggat     840
acatggcctg gagtgactac tctgcctgat tttaaatctg ccttcccaaa atggccttct     900
aaggacctgg caactattgt cccaaatctt gatggagcag gccttgatct tcttgataaa     960
```

```
acttcgcgct tggatcccag caagagaatc actgccagga atgcccttga gcatgagtac   1020
ttcaaggata ttgggtatgt tccgtgagtc tttgcacctt catccagaat gctactgtaa   1080
atttggtatg tcatctacag gttttgttct ggaggattta tgtgattttt agaggcccca   1140 ccccaccccct caagttgtta ttcttccaat gtgattcaat ctatattaaa gtggtcttgc   1200
acagccctca tggatatttg ttgttccagc atttgtggtc acaattcgtg tccgcatgtt   1260
gaaccatact ttccagtgta atatcatttt gttatagttc cgggtgcggt atacctgtcc   1320
aatcatactt gttcagcact ggattctgta atgttaaata gattggtttt ggtgtgtca    1379
```

```
<210> SEQ ID NO 36
<211> LENGTH: 294
<212> TYPE: PRT
<213> ORGANISM: Nicotiana tabacum

<400> SEQUENCE: 36

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Thr Arg His Tyr Ser Thr Pro Val Asp Val Trp Ser Val Gly Cys
            180                 185                 190

Ile Phe Ala Glu Met Val Thr Gln Arg Pro Leu Phe Pro Gly Asp Ser
        195                 200                 205

Glu Ile Asp Glu Leu Phe Lys Ile Phe Arg Val Met Gly Thr Pro Asn
    210                 215                 220

Glu Asp Thr Trp Pro Gly Val Thr Thr Leu Pro Asp Phe Lys Ser Ala
225                 230                 235                 240

Phe Pro Lys Trp Pro Ser Lys Asp Leu Ala Thr Ile Val Pro Asn Leu
                245                 250                 255

Asp Gly Ala Gly Leu Asp Leu Leu Asp Lys Thr Ser Arg Leu Asp Pro
            260                 265                 270

Ser Lys Arg Ile Thr Ala Arg Asn Ala Leu Glu His Glu Tyr Phe Lys
        275                 280                 285

Asp Ile Gly Tyr Val Pro
    290
```

<210> SEQ ID NO 37
<211> LENGTH: 1359
<212> TYPE: DNA
<213> ORGANISM: Nicotiana tabacum

<400> SEQUENCE: 37

```
aattcggcac gagttttggt acaagtacgc cgacacttgc ccgtcgcctc ctcctccgct      60
tcaagacggc gatttcgtcc tctttatccg accaaaggga gttcattgag tttgacctag     120
atggaccagt atgaaaaagt tgagaagatt ggggaaggaa catacggtgt agtgtacaag     180
gctcgtgatc gtgtaactaa tgaaacaatt gcgctgaaga aaataaggct ggagcaggaa     240
gatgagggag taccaagcac agctattaga gaaatctctc tcttgaaaga gatgcagcat     300
gctaatattg tgaggttgca ggatgtagtg cacagtgaga agcgattata tctagtcttt     360
gaatatcttg acttggactt gaagaacaca tggattacta ctcctgaatt ctctgaggat     420
ccacgtctgg ttaaaatgtt tttgtatcaa atactccgtg gtattgccta ttgtcattct     480
catagagttc ttcatcgaga tttgaagcct caaaacttgc tgatagatcg acgtacaaat     540
gctttaaagc ttgcagactt tggattggct agagcatttg gtattcctgt cagaactttc     600
actcatgagg tggtgacatt gtggtacagg gcaccagaaa tactgctggg atcgcgccat     660
tactctactc ctgttgatgt gtggtcagtt ggttgcatat ttgctgagat ggtgactcag     720
cgccctctgt ttcctggtga ttccgagatt gatgaacttt caagattcag agtgatgggt     780
actccaaatg aggatacatg gcctggagtg acaactctgc ctgattttaa atctgccttc     840
ccaaaatggc cttctaagga cctggcaact attgtcccaa atcttgatgg agcaggcctt     900
gatcttcttg ataaaatcgt ccgcttggat cccagcaaga gaatcactgc caggaatgcc     960
cttgagcatg agtacttcaa ggatattggg tatgttccgt gagtctttgc accttcatcc    1020
agaatgctac tgtaaatttg gtatgtcatc tacaaggttt tgttctggag gatttgtgtt    1080
atttttaggg ccacccaccc catcccctca gtgccccac cccatcccct caagttgtta    1140
ttcttccaat gtgattcaat atatattaaa gtggtcttgc acagccctca tggatatttg    1200
ttgttccagc atctgtggtc acaattcgtg tccacatgtt gaaccatact ttccagtgta    1260
atatttgttt gttatagttt ggggtgcggt acacttatcc aatcatactt gtttagcact    1320
ggatactgta atgttaatta gattggtttt ggtgtgtca                           1359
```

<210> SEQ ID NO 38
<211> LENGTH: 293
<212> TYPE: PRT
<213> ORGANISM: Nicotiana tabacum

<400> SEQUENCE: 38

```
Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Asn Thr Trp Ile Thr Thr Pro Glu
                85                  90                  95
```

Phe Ser Glu Asp Pro Arg Leu Val Lys Met Phe Leu Tyr Gln Ile Leu
              100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Thr Gln Arg Pro Leu Phe Pro Gly Asp Ser
        195                 200                 205

Glu Ile Asp Glu Leu Ser Arg Phe Arg Val Met Gly Thr Pro Asn Glu
    210                 215                 220

Asp Thr Trp Pro Gly Val Thr Thr Leu Pro Asp Phe Lys Ser Ala Phe
225                 230                 235                 240

Pro Lys Trp Pro Ser Lys Asp Leu Ala Thr Ile Val Pro Asn Leu Asp
                245                 250                 255

Gly Ala Gly Leu Asp Leu Leu Asp Lys Ile Val Arg Leu Asp Pro Ser
            260                 265                 270

Lys Arg Ile Thr Ala Arg Asn Ala Leu Glu His Glu Tyr Phe Lys Asp
        275                 280                 285

Ile Gly Tyr Val Pro
    290

<210> SEQ ID NO 39
<211> LENGTH: 1398
<212> TYPE: DNA
<213> ORGANISM: Nicotiana tabacum

<400> SEQUENCE: 39
gcggccgcgg atccaaagaa gagtattgac tgtagtccaa acattttggt acaagtacgc    60
cgacacttgc ccgtcgcctc ctcctccgct tcaagacggc gatttcgtcc tctttatccg   120
accaaaggga gttcattgag tttgacctag atggaccagt atgaaaaagt tgagaagatt   180
ggggaaggaa catacggtgt agtgtacaag gctcgtgatc gtgtaactaa tgaaacaatt   240
gcgctgaaga aaataaggct ggagcaggaa gatgagggag taccaagcac agctattaga   300
gaaatctctc tcttgaaaga gatgcagcat gctaatattg tgaggttgca ggatgtagtg   360
cacagtgaga agcgattata tctagtcttt gaatatcttg acttggactt gaagaagcac   420
atggattcat ctcctgaatt ctctgaggat ccacgtctgg ttaaaatgtt tttgtatcaa   480
atactccgtg gtattgccta ttgtcattct catagagttc ttcatcgaga tttgaagcct   540
caaaacttgc tgatagatcg acgtacaaat gctttaaagc ttgcagactt tggattggct   600
agagcatttg gtattcctgt cagaactttc actcatgagg tggtgacatt gtggtacagg   660
gcaccagaaa tactgctggg atcgcgccat tactctactc tgttgatgt gtggtcagtt   720 ggttgcatat ttgctgagat ggtgactcag cgccctctgt ttcctggtga ttccgagatt   780
gatgaacttt tcaagatttt cagagtgatg ggtactccaa atgaggatac atggcctgga   840
gtgacaactc tgcctgattt taatctgcc ttcccaaaat ggccttctaa ggacctggca   900
actattgtcc caaatcttga tggagcaggc cttgatcttc ttgataaaat gctccggttg   960

```
gatcccagca agagaatcac tgccaggaat gcccttgagc atgagtactt caaggatatt    1020
gggtatgttc cgtgagtctt tgcaccttca tccagaatgc tactgtaaat ttggtatgtc    1080
atctacaagg ttttgttctg gaggatttgt gttatttta gggccacccc ccacccccat     1140 cccctcaag ttgttattct tccaatgtga ttcaatatat attaaagtgg tcttggcaca    1200
gccctcatgg atatttgttg ttccagcatc tgtggtcaca attcgtgtcc acatgttgaa    1260
ccatactttc cagtgtaata tttgtttctt atagtttggg gtgcggtaca cttgtccaat    1320
catacttgtt tagcactgga tactgtaatg ttaattagat tggttttggt gtgtcattag    1380
aagttttgca tagtttttt                                                 1398
```

```
<210> SEQ ID NO 40
<211> LENGTH: 294
<212> TYPE: PRT
<213> ORGANISM: Nicotiana tabacum

<400> SEQUENCE: 40

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ser Glu Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Thr Gln Arg Pro Leu Phe Pro Gly Asp Ser
        195                 200                 205

Glu Ile Asp Glu Leu Phe Lys Ile Phe Arg Val Met Gly Thr Pro Asn
    210                 215                 220

Glu Asp Thr Trp Pro Gly Val Thr Thr Leu Pro Asp Phe Lys Ser Ala
225                 230                 235                 240

Phe Pro Lys Trp Pro Ser Lys Asp Leu Ala Thr Ile Val Pro Asn Leu
                245                 250                 255

Asp Gly Ala Gly Leu Asp Leu Leu Asp Lys Met Leu Arg Leu Asp Pro
            260                 265                 270

Ser Lys Arg Ile Thr Ala Arg Asn Ala Leu Glu His Glu Tyr Phe Lys
        275                 280                 285
```

Asp Ile Gly Tyr Val Pro
    290

<210> SEQ ID NO 41
<211> LENGTH: 1126
<212> TYPE: DNA
<213> ORGANISM: Oryza sativa

<400> SEQUENCE: 41

```
cccacgccgc cgccgccgcc cggatcgccg cgagatggag cagtacgaga aggtggagaa      60
gatcggggag gggacgtacg gggtggtgta caagggcaag caccggcata ccaacgagac     120
gatcgcgctc aagaagatcc gcctggagca ggaggacgag ggcgtcccct ccaccgccat     180
ccgcgagatc tcgctgctca aggagatgca gcatcgcaac atcgtcaggc tgcaggacgt     240
cgtgcacaag gagaaatgca tatacctcgt cttcgagtac ctcgaccttg acctcaagaa     300
gcacatggac tcatccccgg atttcaagaa ccaccgcata gtcaaatcgt tcctctacca     360
gattctccgg ggcattgcgt actgccactc gcaccgtgtt ctccaccgag atttgaagcc     420
ccagaacctg ctgatagatc ggcgtaccaa ctcattgaag ctcgcggact tgggttggc      480
cagggcattt ggcattcctg tccggacatt tactcacgag gtggtgacat tgtggtatag     540
agcacctgaa attcttcttg gtgcaaggca ttattccacc cctgttgaca tgtggtcagt     600
tggttgcatt tttgctgaaa tggtgaatca gaagccacta tttcctggag attctgagat     660
tgatgaactc tttaagattt tcagtattat gggcactcca aatgaagaaa cttggccagg     720
tgttgcttca ctacctgact acatatcaac ttttcccaaag tggccatctg tggatcttgc     780
aaccgtggtc ccaacacttg attcttcagg actcgatctt ctctctaaaa tgctccgttt     840
agatccaagc aaaagaatca atgcccgtgc tgccctcgag cacgagtact caaggacct      900
ggaagtggcg tagattatgc ctcatcttgt ccatttgtaa attaagattg cattgtttgc     960
tcagccgagt tctttttttgg cttttccttaa tctaagttgg tgtgctcctc ccccaactct    1020
attttttgccc ttttggttgt gtagagatga aacagaagg tacctcctgg ctatccctct    1080
gtgtaattca agccaattga agatcctta ttgcgggagc tctaaa                    1126
```

<210> SEQ ID NO 42
<211> LENGTH: 292
<212> TYPE: PRT
<213> ORGANISM: Oryza sativa

<400> SEQUENCE: 42

```
Met Glu Gln Tyr Glu Lys Val Glu Lys Ile Gly Glu Gly Thr Tyr Gly
1               5                   10                  15

Val Val Tyr Lys Gly Lys His Arg His Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Lys Glu Lys Cys Ile Tyr Leu Val Phe
65                  70                  75                  80

Glu Tyr Leu Asp Leu Asp Leu Lys Lys His Met Asp Ser Ser Pro Asp
                85                  90                  95

Phe Lys Asn His Arg Ile Val Lys Ser Phe Leu Tyr Gln Ile Leu Arg
            100                 105                 110

Gly Ile Ala Tyr Cys His Ser His Arg Val Leu His Arg Asp Leu Lys
```

```
                115                 120                 125
Pro Gln Asn Leu Leu Ile Asp Arg Arg Thr Asn Ser Leu Lys Leu Ala
    130                 135                 140

Asp Phe Gly Leu Ala Arg Ala Phe Gly Ile Pro Val Arg Thr Phe Thr
145                 150                 155                 160

His Glu Val Val Thr Leu Trp Tyr Arg Ala Pro Glu Ile Leu Leu Gly
                165                 170                 175

Ala Arg His Tyr Ser Thr Pro Val Asp Met Trp Ser Val Gly Cys Ile
            180                 185                 190

Phe Ala Glu Met Val Asn Gln Lys Pro Leu Phe Pro Gly Asp Ser Glu
        195                 200                 205

Ile Asp Glu Leu Phe Lys Ile Phe Ser Ile Met Gly Thr Pro Asn Glu
    210                 215                 220

Glu Thr Trp Pro Gly Val Ala Ser Leu Pro Asp Tyr Ile Ser Thr Phe
225                 230                 235                 240

Pro Lys Trp Pro Ser Val Asp Leu Ala Thr Val Val Pro Thr Leu Asp
                245                 250                 255

Ser Ser Gly Leu Asp Leu Leu Ser Lys Met Leu Arg Leu Asp Pro Ser
            260                 265                 270

Lys Arg Ile Asn Ala Arg Ala Ala Leu Glu His Glu Tyr Phe Lys Asp
        275                 280                 285

Leu Glu Val Ala
    290

<210> SEQ ID NO 43
<211> LENGTH: 1288
<212> TYPE: DNA
<213> ORGANISM: Petroselinum crispum

<400> SEQUENCE: 43
agagaactcc ttttctacat aaaatctccc cccttcctct gaagatttcc ccttgccaac      60
gctctaaaat atctttgcga cttatctgtt aggtgaaatc aaatggacca gtatgaaaag     120
gttgagaaga ttggtgaagg aacatatgga gtagtttata aggctcgtga ccgcgtcaca     180
aatgaaacca tcgctttaaa gaagattcgg ctagagcaag aagatgaagg agtgccaagc     240
actgctatta gagaaatttc tttactgaag gaaatgcagc atggaaatat tgtcaggtta     300
caagatgttg tgcacagcga gaacggttg tatctggttt ttgaatatct ggacctagat      360
ttgaagaaac atatggattc atgtccagag tttgccaagg atccacgtct gataaagatg     420
tttctgtatc aaatacttcg tgggattgct tattgtcatt cccatagagt tctgcatcgg     480
gatctcaaac cccaaaacct gctcatagat cgacgtacca atgctctaaa gcttgcagat     540
tttggacttg ccagggcatt tggaattcct gtcagaacat ttacacacga ggttgtgaca     600
ctttggtaca gggcaccaga gatactcctt ggatcccgcc actattccac acctgttgat     660
gtgtggtctg tcggttgtat ttttgctgag atggtgaacc agcggccatt gtttccgggg     720
gattctgaga ttgatgaatt atttaaaata ttcagaatta cgggtacccc gaatgaggat     780
acctggcctg gagttacatc tctccctgat tttaagtctg cctttccaaa atggccatct     840
aaggaactgg aaactgtggt cccaaatctt gattcggccg tctgaatct cctcaaaaaa      900 atgctttgct tggatccgag cagaagaatt acagccagga ttgcacttga gcatgaatac     960
ttcaaggata ttgggattgt tcctaagtc ttatctttcc ggccgcattt gtatatgata     1020
ttagagtttc ttgggtttga ttttgtaaga aaagtgtgct agttttttt atcgttctat     1080
```

```
agttatttaa tttcctttc cttggatgcg attcttattg tttccaagct ggctgtagag    1140
caatcatata tcatctcgtc cctgctctct gggcttaatg ttcaatgata catgtattgt    1200
cacatgtttt tttttgtaat tctttgtact gtcactaggc atacattgga taatctctta    1260
cttaatgaat ttgtttggtg tgctttgt                                       1288
```

<210> SEQ ID NO 44
<211> LENGTH: 294
<212> TYPE: PRT
<213> ORGANISM: Petroselinum crispum

<400> SEQUENCE: 44

```
Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ala Lys Asp Pro Arg Leu Ile Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Thr Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Pro Ser Lys Glu Leu Glu Thr Val Val Pro Asn Leu
                245                 250                 255

Asp Ser Ala Gly Leu Asn Leu Leu Lys Lys Met Leu Cys Leu Asp Pro
            260                 265                 270

Ser Arg Arg Ile Thr Ala Arg Ile Ala Leu Glu His Glu Tyr Phe Lys
        275                 280                 285

Asp Ile Gly Ile Val Pro
    290
```

<210> SEQ ID NO 45
<211> LENGTH: 922
<212> TYPE: DNA
<213> ORGANISM: Petunia hybrida -continued

```
<400> SEQUENCE: 45
atggaccagt atgaaaaagt tgagaagatt ggggaaggaa catacggtgt agtgtacaag      60
gctcgtgatc gtgtaactaa tgaaacaatt gcgctgaaga aaataaggct ggagcaggaa     120
gatgagggag taccaagcac agctattaga gaaatctctc ttttgaaaga gatgcagcat     180
gctaatattg tgaggttgca ggatgttgtg cacacagtga aaagcgattg tattcttagt     240
tttgaatatc ttgacttgga cttgaagaag cacatggatt catctcctga attctctaag     300
gatccacgtc tggttaaaat gtttctgtat caaatactcc gtgggattgc ttattgccat     360
tctcatagag ttcttcatag agttcttcat cgagatttga agcctcaaaa cttgctgata     420
ggtcgacgta caaatgcttt aaagcttgca gactttggat tggctagagc atttggtatt     480
cctgtcagaa ctttcactca tgaggtggtg acattgtggt acagggcacc agaaatactg     540
ctgggatcac gccattattc tactcctgtt gatgtgtggt cagttggttg catatttgct     600
gagatggtga ctcagcgccc tctgttcct ggtgactccg agattgatga acttttcaag      660
attttcagag tgatgggtac tccaaatgag gatacatggc ctggagtgac tactctgcct     720
gattttaaat ctgccttacc aaaatggcct tctaaggacc tggcaactat tgtcccaaat     780
cttgatggag caggccttga tcttcttgat aaaactgtcc gcttggatcc cagcaagaga     840
atcactgcca ggaatgccct tgagcatgag tacttcaagg atattgggta tgtgttccgt     900 tcgaagggt cctctagagt cg                                               922

<210> SEQ ID NO 46
<211> LENGTH: 307
<212> TYPE: PRT
<213> ORGANISM: Petunia hybrida

<400> SEQUENCE: 46

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Thr Val Lys Ser Asp Cys Ile Leu Ser
65                  70                  75                  80

Phe Glu Tyr Leu Asp Leu Asp Leu Lys Lys His Met Asp Ser Ser Pro
                85                  90                  95

Glu Phe Ser Lys Asp Pro Arg Leu Val Lys Met Phe Leu Tyr Gln Ile
            100                 105                 110

Leu Arg Gly Ile Ala Tyr Cys His Ser His Arg Val Leu His Arg Val
        115                 120                 125

Leu His Arg Asp Leu Lys Pro Gln Asn Leu Leu Ile Gly Arg Arg Thr
    130                 135                 140

Asn Ala Leu Lys Leu Ala Asp Phe Gly Leu Ala Arg Ala Phe Gly Ile
145                 150                 155                 160

Pro Val Arg Thr Phe Thr His Glu Val Val Thr Leu Trp Tyr Arg Ala
                165                 170                 175

Pro Glu Ile Leu Leu Gly Ser Arg His Tyr Ser Thr Pro Val Asp Val
            180                 185                 190

Trp Ser Val Gly Cys Ile Phe Ala Glu Met Val Thr Gln Arg Pro Leu
```

```
                195                 200                 205
    Phe Pro Gly Asp Ser Glu Ile Asp Glu Leu Phe Lys Ile Phe Arg Val
        210                 215                 220

Met Gly Thr Pro Asn Glu Asp Thr Trp Pro Gly Val Thr Thr Leu Pro
    225                 230                 235                 240

Asp Phe Lys Ser Ala Leu Pro Lys Trp Pro Ser Lys Asp Leu Ala Thr
                245                 250                 255

Ile Val Pro Asn Leu Asp Gly Ala Gly Leu Asp Leu Leu Asp Lys Thr
                260                 265                 270

Val Arg Leu Asp Pro Ser Lys Arg Ile Thr Ala Arg Asn Ala Leu Glu
                275                 280                 285

His Glu Tyr Phe Lys Asp Ile Gly Tyr Val Phe Arg Ser Lys Gly Ser
                290                 295                 300

Ser Arg Val
    305

<210> SEQ ID NO 47
<211> LENGTH: 1328
<212> TYPE: DNA
<213> ORGANISM: Picea abies

<400> SEQUENCE: 47
ttcgtgaatg cgtgtttgaa tcgctgaatc tagagatttc tctctaaata ttccgacggg      60
tgcagagaaa aagtcgaaca gaacgggagc ttgaatcagg ctgaatggag cagtatgaga     120
aagttgagaa gataggagaa ggaacatatg gtgtggtcta caaggcccgt gatcgcttga     180
caaatgagac catagctctc aagaaaattc gtttggagca agaagatgag ggtgtaccaa     240
gcactgcaat tagagaaatt tctcttctca agaaatgaca catgggaac atcgtaaggt      300 tgcaggatgt tgtccacagt gaaaagcgtc tctatttagt ttttgagtat tggacttgg      360 acctcaagaa gcatatggat tcttgccccg agctagcaaa ggatcctcgt ctaatcaaaa     420
catttctgta tcagattctg cgtggcattg cctattgtca ttctcatcga gttcttcatc     480
gtgatttgaa accacaaaat ttgcttattg accgcaaaac caatgcgttg aaacttgccg     540
actttggact tgcaagggca tttggaattc cagtgaggac ctttactcat gaggtggtta     600
cattgtggta ccgtgcacca gagatcttgc ttgggtcccg acattattcg actcctgttg     660
atgtttggtc tgtggggtgt atctttgctg aaatggtgaa tcagcgacca cttttcccag     720
gagactcaga gattgatgaa ctctttaaga tatttagagt gctggggaca ccaaatgaag     780
aaacatggcc aggagtcacc tctctgccag acttcaagtc agccttccca agtggccag      840 ccaaggattt ggcaactgtg gttccaggtc ttgagccagc aggaattgat cttctctcga     900
aaatgttgtg cctggagccc agtaaacgca tcactgctcg tagtgctctg agcatgagt      960 atttcaaaga tctaggtttt gtaccctgac ctgtatatta gctgtggggt taagaagatt    1020
attggactgt tgtactgtag cttgcatctt ctcaccagtg aattgctttt cggagactgg    1080
taaactagat ggagacctct ataagtaaca tgattaagta tatcatgttt tttgtatttt    1140
gccacatttg ttaatgattt gcacctttgg tgtagctgga ttatggcgct tctagttctt    1200
caagaccatt gaacaatact ttttctggaa agcagattgt ttacgattgt caaatatgac    1260
ttatcatttg aaattctttg ccatgtgttc tcactgatgg agtattttat aatattgtgc    1320
attctgat                                                             1328

<210> SEQ ID NO 48
```

<211> LENGTH: 294
<212> TYPE: PRT
<213> ORGANISM: Picea abies

<400> SEQUENCE: 48

Met Glu Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Leu Ala Lys Asp Pro Arg Leu Ile Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Lys Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Pro Ala Lys Asp Leu Ala Thr Val Val Pro Gly Leu
                245                 250                 255

Glu Pro Ala Gly Ile Asp Leu Leu Ser Lys Met Leu Cys Leu Glu Pro
            260                 265                 270

Ser Lys Arg Ile Thr Ala Arg Ser Ala Leu Glu His Glu Tyr Phe Lys
    275                 280                 285

Asp Leu Gly Phe Val Pro
    290

<210> SEQ ID NO 49
<211> LENGTH: 1291
<212> TYPE: DNA
<213> ORGANISM: Pinus contorta

<400> SEQUENCE: 49
ccggtctgaa tctttgaatc tagagatttc tctctaaata ttccgacggg tgcagagaaa      60
aagtcgaaca gaacgggatc ttgaatcagg ctgaatggaa cagtatgaga aagttgagaa     120
gataggagaa ggaacatatg gtgtggttta caaggcccgt gatcgcttga caaatgagac     180
catagctctc aagaaaattc gtttggagca agaagatgag ggtgtaccaa gcactgcgat     240

-continued

```
tagagaaatt tctcttctta aagaaatgca acatgggaac atcgtaaggt tgcaagatgt    300
tgtccatagt gaaaagcggc tctatttggt tttcgagtat ttggatttgg acctcaagaa    360
gcatatggat tcttgccctg agctagcaaa ggatcctcgt ctaatcaaaa catttctgta    420
tcagattctg cgtggcattg cctattgtca ttctcatcgg gttcttcatc gtgatctgaa    480
gccgcaaaat ttgcttattg accgcaaaac caatgcgttg aaacttgccg actttggact    540
tgccagggca tttggaattc cagtgaggac ctttactcat gaggtggtta cattgtggta    600
tcgtgcaccc gagatcttac ttggttcccg gcattattcg actcctgttg atgtttggtc    660
tgttggatgt atctttgctg aaatggtcaa tcagcgacca cttttcccag agactcaga    720 gattgatgag ctctttaaga tatttagagt gctggggacg ccaaatgaag aaacatggcc    780
aggagtcacc tctctgcctg acttcaagtc agccttccca agtggccag ccaaggattt    840 ggcaactgtg gtttcaggtc ttgagccagc aggaattgat attctctcga aatgctgtg    900 cctggagccc agtagacgca tcactgctcg tagtgctctg gagcacgagt atttcaaaga    960
tctaggtttt gtaccctgac ctgtatatta gctgcgggga taaaaagatt attggactgt   1020
cgtagcatag cctgcatctt ctcaccagtg agttgctcgt tggaagctgg taaactagat   1080
ggaaacctgt ataagtaaac atgattaagt ataccatgtt tttttttaa atattttgcc    1140 acacttgtta aggatttgca cctttggtgt agctggattg tggtggttct agttcttcaa   1200
gactattgaa caaaacttta tttggaaatt aagttgttta cgattgtcaa atatgactga   1260
tcatttgaaa ttctttgcca aaaaaaaaa a                                   1291
```

<210> SEQ ID NO 50
<211> LENGTH: 294
<212> TYPE: PRT
<213> ORGANISM: Pinus contorta

<400> SEQUENCE: 50

```
Met Glu Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Leu Ala Lys Asp Pro Arg Leu Ile Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Lys Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190
```

```
Ile Phe Ala Glu Met Val Asn Gln Arg Pro Leu Phe Pro Gly Asp Ser
        195                 200                 205

Glu Ile Asp Glu Leu Phe Lys Ile Phe Arg Val Leu Gly Thr Pro Asn
        210                 215                 220

Glu Glu Thr Trp Pro Gly Val Thr Ser Leu Pro Asp Phe Lys Ser Ala
225                 230                 235                 240

Phe Pro Lys Trp Pro Ala Lys Asp Leu Ala Thr Val Val Ser Gly Leu
                245                 250                 255

Glu Pro Ala Gly Ile Asp Ile Leu Ser Lys Met Leu Cys Leu Glu Pro
        260                 265                 270

Ser Arg Arg Ile Thr Ala Arg Ser Ala Leu Glu His Glu Tyr Phe Lys
        275                 280                 285

Asp Leu Gly Phe Val Pro
        290

<210> SEQ ID NO 51
<211> LENGTH: 1108
<212> TYPE: DNA
<213> ORGANISM: Pisum sativum

<400> SEQUENCE: 51
ctgagactag actatgtgac tggaaagacc atacgccgcg ctgtctgtgt aacggtttct      60
cgctccgaac tagaacatcg cttttgaactt agagagtttc ttccatggaa cagtatgaga   120
aggttgagaa ataggagaa ggtacatacg gtgtggtgta caaggctagg gaccgtgtta    180
ccaatgagac cattgctttg aagaagattc gactcgaaca ggaagatgag ggggttccta   240
gcactgccat aagagagatt tctcttttga aagaaatgca gcatcggaac attgttaggt   300
tgcaggatgt tgtgcatagt gagaagcgat tgtatcttgt ttttgagtac cttgacttag   360
atctaaagaa gcatatggat tcatctccgg aattttccaa agatcaacgt caagtaaaaa   420
tgttcctcta tcaaattctc tgtggcattg cttactgtca ttctcataga gttcttcacc   480
gagacctgaa accacaaaat ctgttgatag atcgcagctc taatgcgcta aagcttgcag   540
attttgggtt ggctagagca tttggaattc ctgttaggac atttacacat gaggtggtga   600
cactatggta cagagctcca gaaatattgc ttgggtcccg tcattattct accccagttg   660
atgtttggtc agtgggatgc atatttgcag agatgataaa ccagcgacca cttttccctg   720
gggattctga gattgatgaa ttgtttaaaa tattcagaat cacgggtaca ccaaatgaag   780
atacatggcc tggagtgact tcattgcctg atttttaaatc cgcctttccc aagtggccat   840
ctaaggacct ggcaactctg gtcccaagtc ttgagccatc tggtcttgat ctgttatcta   900
gtatgcttcg cttggatccc agcagaagaa ttactgccag gggcgctctt gagcacgaat   960
acttcaaaga cattaaattt gtcccctgaa gtcctggctt cactgaagag gtgtctatat  1020
tattatgtgt agcagttatg ggtttttggc tcagaagtgt gtgctatccg tgctattttc  1080
ttcaaatgct ttggactgag taatattt                                      1108

<210> SEQ ID NO 52
<211> LENGTH: 294
<212> TYPE: PRT
<213> ORGANISM: Pisum sativum

<400> SEQUENCE: 52

Met Glu Gln Tyr Glu Lys Val Glu Lys Ile Gly Glu Gly Thr Tyr Gly
1               5                   10                  15
```

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
            35                  40                  45

Ile Arg Glu Ile Ser Leu Leu Lys Glu Met Gln His Arg Asn Ile Val
50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ser Lys Asp Gln Arg Gln Val Lys Met Phe Leu Tyr Gln Ile Leu
                100                 105                 110

Cys Gly Ile Ala Tyr Cys His Ser His Arg Val Leu His Arg Asp Leu
            115                 120                 125

Lys Pro Gln Asn Leu Leu Ile Asp Arg Ser Ser Asn Ala Leu Lys Leu
130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Ile Asn Gln Arg Pro Leu Phe Pro Gly Asp Ser
            195                 200                 205

Glu Ile Asp Glu Leu Phe Lys Ile Phe Arg Ile Thr Gly Thr Pro Asn
210                 215                 220

Glu Asp Thr Trp Pro Gly Val Thr Ser Leu Pro Asp Phe Lys Ser Ala
225                 230                 235                 240

Phe Pro Lys Trp Pro Ser Lys Asp Leu Ala Thr Leu Val Pro Ser Leu
                245                 250                 255

Glu Pro Ser Gly Leu Asp Leu Leu Ser Ser Met Leu Arg Leu Asp Pro
            260                 265                 270

Ser Arg Arg Ile Thr Ala Arg Gly Ala Leu Glu His Glu Tyr Phe Lys
            275                 280                 285

Asp Ile Lys Phe Val Pro
    290

<210> SEQ ID NO 53
<211> LENGTH: 420
<212> TYPE: DNA
<213> ORGANISM: Solanum tuberosum

<400> SEQUENCE: 53
ggaattcaga gaaaattggg aagggactt atggcgtagt gtacaaagct cgtgatcgtg    60
taactaatga aactattgca ctgaagaaaa ttcggctgga gcaggaagat gagggtgtgc   120
caagcacggc tattagagaa atctccctct gaaagagat gcagcatgga acattgtga    180 ggttgcaaga tgtggttcac agtgagaagc gattatatct agtgtttgaa tatctcgact   240
tggatttgaa gaagcatatg gactcatgtc cagagttctc taaggatccg cgtcttgtaa   300
aaatgttttt gtatcaaatt ctccgtggaa ttgcttattg tcattctcat agagttcttc   360
accgagatct gaagcctcag aacttgctga tagatagacg tacaaatgtt ctaaagctaa   420

<210> SEQ ID NO 54
<211> LENGTH: 139

```
<212> TYPE: PRT
<213> ORGANISM: Solanum tuberosum

<400> SEQUENCE: 54

Asn Ser Glu Lys Ile Gly Glu Gly Thr Tyr Gly Val Val Tyr Lys Ala
1               5                   10                  15

Arg Asp Arg Val Thr Asn Glu Thr Ile Ala Leu Lys Lys Ile Arg Leu
            20                  25                  30

Glu Gln Glu Asp Glu Gly Val Pro Ser Thr Ala Ile Arg Glu Ile Ser
        35                  40                  45

Leu Leu Lys Glu Met Gln His Gly Asn Ile Val Arg Leu Gln Asp Val
    50                  55                  60

Val His Ser Glu Lys Arg Leu Tyr Leu Val Phe Glu Tyr Leu Asp Leu
65                  70                  75                  80

Asp Leu Lys Lys His Met Asp Ser Cys Pro Glu Phe Ser Lys Asp Pro
                85                  90                  95

Arg Leu Val Lys Met Phe Leu Tyr Gln Ile Leu Arg Gly Ile Ala Tyr
            100                 105                 110

Cys His Ser His Arg Val Leu His Arg Asp Leu Lys Pro Gln Asn Leu
        115                 120                 125

Leu Ile Asp Arg Arg Thr Asn Val Leu Lys Leu
    130                 135

<210> SEQ ID NO 55
<211> LENGTH: 1227
<212> TYPE: DNA
<213> ORGANISM: Sesbania rostrata

<400> SEQUENCE: 55
gcacgagctt ctcttgtctt ggttgagtga gtgagtgagt ctcactgcgc caacaactct     60
gtccctttct tcttcttctt ttcagatctt gtatttgttt actcaatttc cctcttaagt    120
ctcttagctt tcaactgaga cttgttccca tggaacagta cgagaaggtc gagaagattg    180
gcgaaggaac atacggcgtc gtttataagg cccgcgaccg cgtcaccaat gagaccatcg    240
ctctcaagaa aattcgcctc gagcaagagg acgaaggggt tcccagcacc gccatacgcg    300
agatttctct cttgaaagaa atgcagcata ggaacattat taggttgcaa gatgtagtgc    360
acagcgagaa gcgattgtat ctggtttttg agtatctgga cttagatcta agaagcaca    420 tggattcatc tcctgagttt gtgaaagatc cgcgacaagt aaaaatgttc ctttatcaaa    480
ttctctgtgg cattgcttac tgtcattcac atagagttct tcaccgagac ttgaaaccac    540
agaatttgtt gatagatcgc cgtactaatt cactaaagct tgcagatttt ggattggcta    600
gggcatttgg cattcctgtc aggacattta cacatgaggt tgtcacactg tggtacagag    660
ctccaggcat attgcttgga tctcgtcatt attctacccc agttgatatc tggtcagtgg    720
gatgtatatt tgcagagatg gtaaaccgac ggcctctatt ccctggtgac tctgagattg    780
atgaattgtt taaaatattc agaatcttgg gtacaccaaa tgaagataca tggcccggag    840
taacttcatt gcctgatttt aaatcaacat ttcccaagtg gccacctaag gatctagcaa    900
ctgtggttcc aaatcttgag caagctggtc ttaatcttct ttctagtatg ctttgcttgg    960
atcccagcaa agaattacc gccaggagcg ctgtggagca tgaatacttc aaagacatta   1020
aatttgtacc ctgattccat atcttcatgg ccaaggtgtt tatagtaata tgttcagaat   1080
ttatgggttt tgactatgcg agaaatgcgt tctatctttg ctctttcctt caatgacttg   1140
gggctgtcat atttcaattt tttgtccttg ccaatatttc agaatcaact tgagtgtgga   1200
```

```
aaaaaaaaaa aaaaaaaaaa aaaaaaa                                         1227
```

<210> SEQ ID NO 56
<211> LENGTH: 294
<212> TYPE: PRT
<213> ORGANISM: Sesbania rostrata

<400> SEQUENCE: 56

```
Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Ile
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Val Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Gly Ile Leu Leu
                165                 170                 175

Gly Ser Arg His Tyr Ser Thr Pro Val Asp Ile Trp Ser Val Gly Cys
            180                 185                 190

Ile Phe Ala Glu Met Val Asn Arg Arg Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Asp Thr Trp Pro Gly Val Thr Ser Leu Pro Asp Phe Lys Ser Thr
225                 230                 235                 240

Phe Pro Lys Trp Pro Pro Lys Asp Leu Ala Thr Val Val Pro Asn Leu
                245                 250                 255

Glu Gln Ala Gly Leu Asn Leu Leu Ser Ser Met Leu Cys Leu Asp Pro
            260                 265                 270

Ser Lys Arg Ile Thr Ala Arg Ser Ala Val Glu His Glu Tyr Phe Lys
        275                 280                 285

Asp Ile Lys Phe Val Pro
    290
```

<210> SEQ ID NO 57
<211> LENGTH: 1170
<212> TYPE: DNA
<213> ORGANISM: Triticum aestivum

<400> SEQUENCE: 57

```
gccccctct  ccccctcccc  cccaccccc   caatggcggc  agcagcagca  gcagcagcag    60
cagcttcgcc  cgccgcagcc  gctctccccc  gcccctcctc  cccgtgatcc  ccttcccctt   120
```

```
cccctccccc gcttcctcct ctccccctc ccgcctcctc acccatttcc cacgcccgcg      180
ccgccgccgc cgccgtagca ttggacgccg acccgatgga gcagtacgag aaggtggaga      240
agatcgggga gggcacgtac ggggtggtgt acaaggcccg ggacaggacc accaacgaga      300
ccatcgcgct caagaagatc cgcctggagc aggaggacga gggcgtcccc tccaccgcca      360
tccgcgagat ctcgctcctc aaggagatgc agcacggcaa catcgtcaag ctgcacgatg      420
ttgtccacag cgagaagcgc atatggctcg tctttgagta cctggatctg gacctgaaga      480
agttcatgga ctcctgtcca gagtttgcca agagccccgc cttgatcaag tcatatctct      540
atcagatact ccgcggcgtt gcttactgtc attctcatag agttcttcat cgagatttga      600
aacctcagaa tttattgata gaccggcgta ctaatgcact gaagcttgca gactttggtt      660
tagcaagggc atttggaatt cctgtccgta catttactca tgaggtagta acattatggt      720
acagagctcc tgaaatcctt cttggagcaa ggcagtattc cacaccagtt gacgtgtggt      780
cagtgggctg tatctttgca gaaatggtga accagaaacc actgttccct ggcgattctg      840
agattgatga gctatttaag atattcaggg tactcggcac tccaaatgaa caaacttggc      900
caggcgtgag ttccttgcct gactacaagt ccgccttccc caggtggcag gcagaggacc      960
ttgcaaccgt tgtccccaat cttgaacctg ttggcctgga ccttctctcg aaaatgcttc     1020
ggttcgagcc aaacaagagg atcacggcta ggcaggctct tgagcatgag tacttcaagg     1080
acatggagat ggtacagtga gctggctatg tggtagtgac tggcatatgt atgagctgag     1140
ctgctcgttt cattcctttt gtgaacgctc                                     1170
```

<210> SEQ ID NO 58
<211> LENGTH: 294
<212> TYPE: PRT
<213> ORGANISM: Triticum aestivum

<400> SEQUENCE: 58

```
Met Glu Gln Tyr Glu Lys Val Glu Lys Ile Gly Glu Gly Thr Tyr Gly
1               5                   10                  15

Val Val Tyr Lys Ala Arg Asp Arg Thr Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Lys Leu His Asp Val Val His Ser Glu Lys Arg Ile Trp Leu Val Phe
65                  70                  75                  80

Glu Tyr Leu Asp Leu Asp Leu Lys Lys Phe Met Asp Ser Cys Pro Glu
                85                  90                  95

Phe Ala Lys Ser Pro Ala Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Val Trp Ser Val Gly Cys
```

-continued

```
                    180                 185                 190
Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Gln Thr Trp Pro Gly Val Ser Ser Leu Pro Asp Tyr Lys Ser Ala
225                 230                 235                 240

Phe Pro Arg Trp Gln Ala Glu Asp Leu Ala Thr Val Val Pro Asn Leu
                245                 250                 255

Glu Pro Val Gly Leu Asp Leu Leu Ser Lys Met Leu Arg Phe Glu Pro
            260                 265                 270

Asn Lys Arg Ile Thr Ala Arg Gln Ala Leu Glu His Glu Tyr Phe Lys
        275                 280                 285

Asp Met Glu Met Val Gln
    290
```

<210> SEQ ID NO 59
<211> LENGTH: 915
<212> TYPE: DNA
<213> ORGANISM: Triticum aestivum

<400> SEQUENCE: 59

```
cccacccccac tcctccccgc cgccgccgcc gccgccccgc tccgatccgc cccgcgccgc      60
gcggatcgcc gcgccatgga ccagtacgag aaggtggaga gatcgggga gggcacgtac     120
ggggtggtgt acaaggccaa ggaccgctac accaacgaga cgatcgcgct caagaagatc     180
cggctggagc aggaggacga gggcgtcccc tccaccgcca tccgcgagat ctccctcctc     240
aaggagatgc agcaccggaa catcgtcagg ctgcaggacg tggtgcacaa cgagaagtgc     300
atatacctcg tcttcgagta cctcgacctc gacctcaaga agcacatgga ctcctccgcg     360
gacttcaaga accaccacat agtcaagtcc ttcctctacc agatcctgca cggcatcgcc     420
tactgccact cgcaccgtgt gcttcacagg gatctcaagc cccagaacct gctgatagat     480
cgccgtacca attcattgaa gcttgctgac ttcggattgg cgagggcgtt cggcattcct     540
gtccggacat ttactcacga ggtggtgaca ttatggtata gagcaccaga aattcttctg     600
ggtgcgaggc agtattctac ccctgttgat gtgtggtcgg ttggttgcat tttcgccgaa     660
atggtgaatc agaaacctct atttcctggt gattctgaga ttgatgaact cttcaagatt     720
ttcagaatta tgggcactcc taatgaagaa acctggccag tgtttcttc gttacctgac     780
tacaaatcag ctttccccaa gtggccatcc gtggatcttg caactgtggt tccaacactc     840
gaacctttgg gacttgatct ctctctaaa atgctctgct agatccaac cagaagaatc     900
aacgcccgaa ccgcc                                                      915
```

<210> SEQ ID NO 60
<211> LENGTH: 280
<212> TYPE: PRT
<213> ORGANISM: Triticum aestivum

<400> SEQUENCE: 60

```
Met Asp Gln Tyr Glu Lys Val Glu Lys Ile Gly Glu Gly Thr Tyr Gly
1               5                   10                  15

Val Val Tyr Lys Ala Lys Asp Arg Tyr Thr Asn Glu Thr Ile Ala Leu
            20                  25                  30

Lys Lys Ile Arg Leu Glu Gln Glu Asp Glu Gly Val Pro Ser Thr Ala
        35                  40                  45
```

```
Ile Arg Glu Ile Ser Leu Leu Lys Glu Met Gln His Arg Asn Ile Val
 50                  55                  60
Arg Leu Gln Asp Val Val His Asn Glu Lys Cys Ile Tyr Leu Val Phe
 65                  70                  75                  80
Glu Tyr Leu Asp Leu Asp Leu Lys Lys His Met Asp Ser Ser Ala Asp
                 85                  90                  95
Phe Lys Asn His His Ile Val Lys Ser Phe Leu Tyr Gln Ile Leu His
                100                 105                 110
Gly Ile Ala Tyr Cys His Ser His Arg Val Leu His Arg Asp Leu Lys
            115                 120                 125
Pro Gln Asn Leu Leu Ile Asp Arg Arg Thr Asn Ser Leu Lys Leu Ala
130                 135                 140
Asp Phe Gly Leu Ala Arg Ala Phe Gly Ile Pro Val Arg Thr Phe Thr
145                 150                 155                 160
His Glu Val Val Thr Leu Trp Tyr Arg Ala Pro Glu Ile Leu Leu Gly
                165                 170                 175
Ala Arg Gln Tyr Ser Thr Pro Val Asp Val Trp Ser Val Gly Cys Ile
            180                 185                 190
Phe Ala Glu Met Val Asn Gln Lys Pro Leu Phe Pro Gly Asp Ser Glu
        195                 200                 205
Ile Asp Glu Leu Phe Lys Ile Phe Arg Ile Met Gly Thr Pro Asn Glu
210                 215                 220
Glu Thr Trp Pro Gly Val Ser Ser Leu Pro Asp Tyr Lys Ser Ala Phe
225                 230                 235                 240
Pro Lys Trp Pro Ser Val Asp Leu Ala Thr Val Val Pro Thr Leu Glu
                245                 250                 255
Pro Leu Gly Leu Asp Leu Leu Ser Lys Met Leu Cys Leu Asp Pro Thr
            260                 265                 270
Arg Arg Ile Asn Ala Arg Thr Ala
        275                 280

<210> SEQ ID NO 61
<211> LENGTH: 1324
<212> TYPE: DNA
<213> ORGANISM: Vigna acunitifolia

<400> SEQUENCE: 61
gcgggtagtg tatacaattt gtaaatagtt aaagaaaag  cattaaacaa aaaagaggg       60 aaagggtag  taaaggaaag agaagaaaga gttgagaaga gtgaaagaga gagagagaga     120
gagagagaga agaagtgaca agagtggagt gtgcgtgaga gagtgactgc aaaacgctcc    180
acccttgttt cttctcagat cttccatgga acagtacgag aaggtggaga agataggga     240 gggaacatac ggcgtcgttt acaaggctcg cgaccgcgtc accaatgaga ccatcgctct    300
taagaagatt cgcctcgagc aggaagacga gggggttccc agcaccgcca ttcgtgagat    360
ttcgctcctc aaagagatgc agcataggaa cattgttagg ttgcaggatg tagtgcacag    420
tgagaagcga ttgtatctgg ttttcgagta tctggacttg gatctaaaga aacacatgga    480
ttcatctcca gagtttgtga agatccacg  gcaagtaaaa atgttcctct atcaaattct    540
ctgtggcatt gcttactgcc attcgcacag agttcttcat cgagacttga aaccacagaa    600
tttgttgata gaccgtcgta caattccctt aaaacttgca gattttggat tggctagggc    660
atttggcatt cctgtcagga catttactca tgaggtggtg acattatggt acagagctcc    720
agaaatattg cttgggtctc gtcattattc taccccagtt gatgtttggt cagtgggatg    780
```

-continued

```
tatatttgca gagatggtaa accgacgacc tctattccca ggggactctg agattgatga    840
attatttaaa atattcagaa tattgggtac acctaatgaa gaaacatggc ctggagttac    900
tgcattaccg gattttaaat caacatttcc caaatggcca cctaaggatt tagcaactgt    960
ggttccaaat cttgatgcag cgggtcttaa tcttctttct agtatgctat gcttggatcc   1020
cagcaaaaga attactgcca ggatcgctgt ggagcacgaa tacttcaaag acattaaatt   1080
tgtaccctaa ttccatatct tcatggaaac cgtgtttata gtaatatttt gtgcagaatt   1140
tatgggtttt gactctgcga gaaatgcgtg ctgtcttttg ctatttcttc aggacttggg   1200
agttgggagt gggtcatatt tccattttt gtcctacaga tatttgagaa tgaacttgag   1260
tgtgatcata ctgcatttta catttcccct tgtccatgca atgcaatgca ccagttaact   1320
tttc                                                                1324
```

<210> SEQ ID NO 62
<211> LENGTH: 294
<212> TYPE: PRT
<213> ORGANISM: Vigna acunitifolia

<400> SEQUENCE: 62

```
Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Val Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Arg Arg Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Glu Thr Trp Pro Gly Val Thr Ala Leu Pro Asp Phe Lys Ser Thr
225                 230                 235                 240

Phe Pro Lys Trp Pro Pro Lys Asp Leu Ala Thr Val Val Pro Asn Leu
                245                 250                 255

Asp Ala Ala Gly Leu Asn Leu Leu Ser Ser Met Leu Cys Leu Asp Pro
            260                 265                 270
```

Ser Lys Arg Ile Thr Ala Arg Ile Ala Val Glu His Glu Tyr Phe Lys
    275                 280                 285

Asp Ile Lys Phe Val Pro
    290

<210> SEQ ID NO 63
<211> LENGTH: 1309
<212> TYPE: DNA
<213> ORGANISM: Vigna unguiculata

<400> SEQUENCE: 63
cgaagtgaca agagtggagt gtgcgtgaga gagtgactgc aaaccgctcc acccttgttt      60
cttctcagat cttccatgga acagtacgag aaggtggaga agataggcga gggaacatac     120
ggcgtcgttt acaaggctcg ggaccgcgtc actgatgaga ccatcgcgct caagaagatt     180
cgcctggagc aggaggacga gggggttccc agcaccgcca ttcgtgagat tcgctcctc      240 aaagagatgc agcataggaa cattgttagg ttgcaggatg tagtgcacag tgagaaacga     300
ttgtatctgg ttttcgagta tctggacttg gatctaaaga aacacatgga ttcatctcca     360
gagtttgtga aagatccacg gcaagtaaaa atgttcctct atcaaattct ctgtggcatt     420
gcttactgcc attcgcacag agttcttcat cgagacttga aaccacagaa tttgttgata     480
gaccgtcgta caaattcctt aaaacttgca gattttggat tggctagggc atttggcatt     540
cctgtcagga catttactca tgaggtggtg acattatggt acagagctcc agaaatattg     600
ctcgggtctc gtcattattc taccccagtt gatgtttggt cagtgggatg tttatttgca     660
gagatggtaa accgacgacc tctattccct ggggactctg agattgatga attatttaaa     720 atattccagaa tattgggtac accaaatgaa gaaacatggc ctggagttac tgcattaccg     780
gattttaaat caacatttcc caaatggcca cctaaggatt tagcaactat ggttccaaat     840
cttgatgcag ccggtcttaa tcttctttct agtatgctaa gcctggatcc cagcaaaaga     900
attaccgcca ggatcgctgt ggagcatgaa tacttcaaag acattaaatt tgtaccctga     960
ttccatatct tcatggaaaa cgtgtttata gtaatatttt gcgcagaatt tatgggtttt    1020
gactctgcga gaaatgcgtg ttgtcttttg ctattttctt caggacttgg gagttgggac    1080
tgggtcatat tccatttttt gtcctacaga atatttcaga atcaacttga gtgtgatcaa    1140
attgcatttt acttttcctt ttgtccagtc aatgcaatgc agcatttaag ttttcagttt    1200
gtctgatatg tgtgatgctg cttcttgata cagaagaagc gtatctacat tctttcaaga    1260
tgcgttgatt gataaaatta gtttcatttg tgttttcca aaaaaaaaa                  1309

<210> SEQ ID NO 64
<211> LENGTH: 294
<212> TYPE: PRT
<213> ORGANISM: Vigna unguiculata

<400> SEQUENCE: 64

Met Glu Gln Tyr Glu Lys Val Glu Lys Ile Gly Glu Gly Thr Tyr Gly
1               5                   10                  15

Val Val Tyr Lys Ala Arg Asp Arg Val Thr Asp Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

```
Arg Leu Gln Asp Val Val His Ser Glu Lys Arg Leu Tyr Leu Val Phe
 65                  70                  75                  80

Glu Tyr Leu Asp Leu Asp Leu Lys Lys His Met Asp Ser Ser Pro Glu
                 85                  90                  95

Phe Val Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Leu Phe Ala Glu Met Val Asn Arg Arg Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Glu Thr Trp Pro Gly Val Thr Ala Leu Pro Asp Phe Lys Ser Thr
225                 230                 235                 240

Phe Pro Lys Trp Pro Pro Lys Asp Leu Ala Thr Met Val Pro Asn Leu
                245                 250                 255

Asp Ala Ala Gly Leu Asn Leu Leu Ser Ser Met Leu Ser Leu Asp Pro
            260                 265                 270

Ser Lys Arg Ile Thr Ala Arg Ile Ala Val Glu His Glu Tyr Phe Lys
        275                 280                 285

Asp Ile Lys Phe Val Pro
    290

<210> SEQ ID NO 65
<211> LENGTH: 1325
<212> TYPE: DNA
<213> ORGANISM: Zea mays

<400> SEQUENCE: 65
cgcgggcgag gagcagacca gcacccagcg ccctcgtcgg ggggcggcac gtgcagcttc      60
accagccgcc gcctttcccc cgtctgcctc tgcctctgcc tctcccccta accccttcc     120 atttctccac cccacccccgc tcccgcttcc gcttcctcgc cacttagttc gttgccacca     180
cgccgcggct gcgttcgcat tgggggcacg caatggagca gtacgagaag gtggagaaga     240
tcggggaggg cacgtacggg gtggtgtaca aggcgctgga caaggccacc aacgagacga     300
tcgcgctcaa gaagatccgc ctcgagcagg aggacgaggg cgtcccgtcc accgccatcc     360
gcgagatctc tctcctcaag gagatgaacc acggcaacat cgtcagatta catgatgttg     420
tccacagcga aagcgcata taccttgtct tcgagtacct ggatctggac ctcaagaagt     480
tcatggactc ctgcccggag tttgctaaga atcccacttt gatcaagtca tacctctacc     540
agatactcca cggtgttgcg tactgccatt ctcatagagt tcttcatcga acttgaaaac     600
ctcaaaactt attgatagat cggcgcacta atgcactgaa gcttgcagac tttggtttag     660
ccagggcatt tggaattcct gtccgtacat ttactcatga ggtagtgaca ttatggtaca     720
gagctccaga aattctgctt ggagcgcggc agtattccac accagttgat gtgtggtctg     780
```

```
tgggctgtat ctttgcggaa atggtgaacc aaaagccact attccctggc gattctgaga    840
tcgacgaact ttttaagata ttcaggatac taggtacacc gaatgagcag agttggccag    900
gagtcagttg tttgcctgac ttcaagacag ctttccccag gtggcaagct caggacctgg    960
caacagtagt cccaaatctt gaccctgctg ggttggacct tctctctaaa atgcttcgat   1020
acgagccaag caaagaatc acagcgaggc aagcacttga gcatgagtac ttcaaggacc   1080
ttgaagtggt acagtgacct gctaaatgtg cttgacgttg cattgacatt tgtatgagct   1140
gagtcgctca ttccttttta tgaacgcctg tactcttctc attctctccc tgcatttttg   1200
tcattcagct ggatatttcg aatctggtgt gttttgagat gtattaaaga acgtcaaata   1260
gattaccgcc ttggtctctg tccattgaaa gtaaatatcc gtcataaaaa aaaaaaaaa   1320 aaaaa                                                               1325
```

<210> SEQ ID NO 66
<211> LENGTH: 294
<212> TYPE: PRT
<213> ORGANISM: Zea mays

<400> SEQUENCE: 66

```
Met Glu Gln Tyr Glu Lys Val Glu Lys Ile Gly Glu Gly Thr Tyr Gly
1               5                   10                  15

Val Val Tyr Lys Ala Leu Asp Lys Ala Thr Asn Glu Thr Ile Ala Leu
                20                  25                  30

Lys Lys Ile Arg Leu Glu Gln Glu Asp Glu Gly Val Pro Ser Thr Ala
            35                  40                  45

Ile Arg Glu Ile Ser Leu Leu Lys Glu Met Asn His Gly Asn Ile Val
        50                  55                  60

Arg Leu His Asp Val Val His Ser Glu Lys Arg Ile Tyr Leu Val Phe
65                  70                  75                  80

Glu Tyr Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

His Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Gln Ser Trp Pro Gly Val Ser Cys Leu Pro Asp Phe Lys Thr Ala
225                 230                 235                 240

Phe Pro Arg Trp Gln Ala Gln Asp Leu Ala Thr Val Val Pro Asn Leu
                245                 250                 255

Asp Pro Ala Gly Leu Asp Leu Leu Ser Lys Met Leu Arg Tyr Glu Pro
            260                 265                 270
```

```
-continued

Ser Lys Arg Ile Thr Ala Arg Gln Ala Leu Glu His Glu Tyr Phe Lys
        275                 280                 285

Asp Leu Glu Val Val Gln
    290

<210> SEQ ID NO 67
<211> LENGTH: 21
<212> TYPE: PRT
<213> ORGANISM: Unknown
<220> FEATURE:
<223> OTHER INFORMATION: Substrate for A-type CDK

<400> SEQUENCE: 67

Ala Asp Ala Gln His Ala Thr Pro Pro Lys Lys Lys Arg Lys Val Glu
1               5                   10                  15

Asp Pro Lys Asp Phe
            20
```

PLANTS HAVING IMPROVED GROWTH CHARACTERISTICS AND METHOD FOR MAKING THE SAME

RELATED APPLICATIONS

This application is a national stage application (under 35 U.S.C. 371) of PCT/EP2005/056364 filed Nov. 30, 2005, which claims benefit of European application 04106225.8 filed Dec. 1, 2004 and U.S. Provisional Application 60/634,015 filed Dec. 7, 2004.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence list-14546-00018-US, date recorded: May 30, 2007, size: 130 KB.

The present invention relates generally to the field of molecular biology and concerns a method for improving plant growth characteristics. More specifically, the present invention concerns a method for improving plant growth characteristics by modulating expression in a plant of a plant nucleic acid encoding an A-type cyclin dependent kinase (CDKA) and/or by modulating activity in a plant of a plant CDKA protein, which CDKA protein comprises a T161D-type mutation or which CDKA nucleic acid encodes such protein. The present invention also concerns plants having modulated expression of a plant CDKA nucleic acid and/or modulated activity of a plant CDKA protein, which CDKA protein comprises a T161D-type mutation or which nucleic acid encodes such protein and which plants have improved growth characteristics relative to corresponding wild type plants. The invention also provides plant CDKs with a PSTAIRE motif and a T161D-type mutation, and nucleic acids encoding such proteins.

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Crop yield is influenced by the typical stresses to which plants or crops are subjected. Such stresses include environmental (abiotic) stresses (such as temperature stresses caused by atypical high or low temperatures; stresses caused by nutrient deficiency; stresses caused by lack of water (drought)) and biotic stresses (which can be imposed on plants by other plants (weeds), animal pests and pathogens). Crop yield may not only be increased by combating one or more of the stresses to which the crop or plant is subjected, but may also be increased by modifying the inherent growth mechanisms of a plant.

The inherent growth mechanisms of a plant reside in a highly ordered sequence of events collectively known as the 'cell cycle'. The ability to influence the cell cycle in a plant (either using recombinant DNA technology or using non-recombinant means), and to thereby modify various growth characteristics of a plant, would have many applications in areas such as crop enhancement, plant breeding, production of ornamental plants, arboriculture, horticulture, forestry, the production of algae or plants (for example for use as bioreactors, for the production of substances such as pharmaceuticals, antibodies, or vaccines, or for the bioconversion of organic waste or for use as fuel in the case of high-yielding algae and plants).

Progression through the cell cycle is fundamental to the growth and development of all multicellular organisms and is crucial to cell proliferation. The major components of the cell cycle are highly conserved in yeast, mammals, and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase may be stimulated to renter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The expression of genes necessary for DNA synthesis at the G1/S boundary is regulated by the E2F family of transcription factors in mammals and plant cells (WO 96/25494; Muller et al., Genes and Development 15, 267-285, 2001; De Veylder et al., EMBO J. 21, 13602-1368, 2002). Entry into the cell cycle is regulated/triggered by an E2F/Rb complex that integrates signals and allows activation of transcription of cell cycle genes. The transition between the different phases of the cell cycle, and therefore progression through the cell cycle, is driven by the formation and activation of different heterodimeric serine/threonine protein kinases, generally referred to as cyclin-dependent kinases (CDK). A prerequisite for activity of these kinases is the physical association with a specific cyclin, the timing of activation being largely dependent upon cyclin expression. Cyclin-binding induces conformational changes in the N-terminal lobe of the associating CDK and contributes to the localisation and substrate specificity of the complex. Monomeric CDKs are activated when they are associated with cyclins and thus have kinase activity. Cyclin protein levels fluctuate in the cell cycle and therefore represent a major factor in determining timing of CDK activation. The periodic activation of these complexes containing cyclins and CDK during cell cycle mediates the temporal regulation of cell-cycle transitions (checkpoints). Other factors regulating CDK activity include CDK inhibitors (CKIs or ICKs, KIPs, CIPs, INKs), CDK activating kinase (CAK), CDK phosphatase (Cdc25) and CDK subunit (CKS) (Mironov et al. Plant Cell 11, 509-522, 1999; Reed, S. I. Progress in Cell Cycle Research 2, 5-27, 1996).

In plants, two major classes of CDKs, known as A-type and B-type CDKs, have been studied to date. The A-type CDKs regulate both the G1-to-S and G2-to-M transitions, whereas the B-type CDKs seem to control the G2-to-M checkpoint only (Hemerly et al., 1995; Magyar et al., 1997; Porceddu et al., 2001). In addition, the presence of C-type CDKs and CDK-activating kinases (CAKs) has been reported (Magyar et al., 1997; Umeda et al., 1998; Joubès et al., 2001), as has the presence of D-type, E-type and F-type CDKs (Vandepoele et al. Plant Cell 14, 903-916, 2002).

A-type CDKs are known to have a conserved tertiary structure (Goldsmith and Cobb, Curr. Opin. Struct. Biol. 4, 833-840), including a highly conserved PSTAIRE motif that is involved in cyclin binding. The catalytic core of a CDK is composed of an N-terminal and a C-terminal lobe. The C-terminal lobe encompasses a catalytic cleft (responsible for ATP and substrate binding) and further comprises a so-called T-loop, named after a threonine residue that is conserved in several kinase families. In human CDK2, this threonine residue is on position 161, whereas in *Saccharomyces cerevisiae* cdc28 and in *Schizosaccharomyces pombe* cdc2 it is located on position 169 and 167 respectively. Phosphorylation of this threonine residue is reported to cause a structural conformation change in the T-loop that is necessary for switching the kinase into an active state (Gu et al., EMBO J. 11, 3995-4005). Several studies describe mutations of the conserved threonine in the T-loop (Ducommun et al. EMBO J. 10, 3311-3319, 1991; Gould et al. EMBO J. 10, 3297-3309; Marcote et al. Mol. Cell. Biol. 13, 5122-5131, 1993; Ducommun et al. Mol Cell. Biol. 11, 6177-6184, 1991; Coleman et al. J. Biol. Chem. 272, 18869-18874, 1997; Martinez et al. EMBO J. 16, 343-354, 1997; Gould et al. Mol. Gen. Genet. 259, 437-448, 1998; Booher et al. Mol. Cell. Biol. 6, 3523-3530, 1986; Solomon et al. Mol. Biol. Cell 3, 13-27, 1992; Lim et al. Mol. Cell. Biol. 16, 4573-4583, 1996), all mutations tested were shown to have a serious impact on binding of ligands (such as cyclin or Suc1/ICK) and/or on kinase activity, resulting in defective or lethal phenotypes in yeast complementation experiments. Although the T169E mutation (according to the numbering for yeast cdc28), and by analogy also the T169D mutation, mimics a phosphorylation, it was demonstrated that none of the CDKs with such mutations were able to fully complement yeast. Other residues that play an important role in A-type CDK protein activity are threonine at position 14 and tyrosine at position 15. Upon phosphorylation of at least one of these amino acids, the CDK becomes inactivated. WO 99/54489 describes the use of a CDK with threonine 14 and tyrosine 15 substituted by alanine and phenylalanine respectively to increase the tolerance of plants to salt stress. WO 00/52171 describes a method of modifying one or more plant cytokinin-mediated morphological, biochemical and physiological properties or characteristics comprising expressing a Cdc25 phosphoprotein phosphatase in a plant.

It has now surprisingly been found that expression in a plant of an A-type cyclin dependent kinase (CDKA) with a T161D-type mutation gives plants having improved growth characteristics.

Therefore, according to one embodiment of the present invention there is provided a method for improving plant growth characteristics relative to corresponding wild type plants, comprising modulating activity in a plant of an A-type CDK having a T161D-type mutation and/or modulating expression of a nucleic acid encoding such A-type CDK, and optionally selecting plants having improved growth characteristics.

Advantageously, performance of the method according to the present invention results in plants having a variety of improved growth characteristics relative to corresponding wild type plants and which improved growth characteristics comprise at least increased yield relative to corresponding wild type plants.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased total seed yield, which includes an increase in seed biomass (seed weight) and which may be an increase in the seed weight per plant or on an individual seed basis; (iii) increased number of flowers ("florets") per panicle (iv) increased number of (filled) seeds; (v) increased seed size, which may also influence the composition of seeds; (vi) increased seed volume, which may also influence the composition of seeds (including oil, protein and carbohydrate total content and composition); (vii) increased individual seed area; (viii) increased individual seed length and/or width; (ix) increased harvest index, which is expressed as a ratio of the yield of harvestable parts, such as seeds, over the total biomass; and (x) increased thousand kernel weight (TKW), which is extrapolated from the number of filled seeds counted and their total weight. An increased TKW may result from an increased seed size and/or seed weight. An increased TKW may result from an increase in embryo size and/or endosperm size.

Taking corn as an example, a yield increase may be manifested as one or more of the following: increase in the number of plants per hectare or acre, an increase in the number of ears per plant, an increase in the number of rows, number of kernels per row, kernel weight, TKW, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, expressed (in %) as the proportion of the number of filled seeds over the number of florets (total number of seeds), increase in TKW, among others. An increase in yield may also result in modified architecture, or may occur as a result of modified architecture.

According to a preferred feature, performance of the methods according to the present invention results in plants having increased yield and more particularly, increased biomass and/or increased seed yield. Preferably, the increased seed yield comprises an increase in one or more of the following: number of (filled) seeds, total seed weight, seed size, seed volume, thousand kernel weight and harvest index, each relative to control plants.

Therefore, according to the present invention, there is provided a method for increasing plant yield relative to corresponding control plants, which method comprises modulating activity of a CDK or a homologue thereof in a plant, which CDK or homologue has a PSTAIRE motif and a T161D-type mutation, and/or modulating expression of a nucleic acid encoding such a CDKA or homologue thereof.

Since the plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant or cell types, including seeds, of a plant, or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. An increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potatoes or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises modulating activity of a CDK or a homologue thereof in a plant, which CDK or homologue has a PSTAIRE motif and a T161D-type mutation, and/or modulating expression of a nucleic acid encoding such a CDKA or homologue thereof.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects. The term "non-stress conditions" as used herein are those environmental conditions that do not significantly go beyond the everyday climatic and other abiotic conditions that plants may encounter. Persons skilled in the art are aware of normal soil conditions and climatic conditions for a given geographic location.

The abovementioned growth characteristics may advantageously be modified in any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest or the specific modification in the gene/nucleic acid of interest. The term "plant" also encompasses plant cells, suspension cultures, callus tissue, embryos, meristematic regions, gametophytes, sporophytes, pollen, and microspores, again wherein each of the aforementioned comprise the gene/nucleic acid of interest.

Plants that are particularly useful in the methods of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus*, *Annona* spp., *Apium graveolens*, *Arabidopsis thaliana*, *Arachis* spp, *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carica papaya*, *Carissa macrocarpa*, *Carthamus tinctorius*, *Carya* spp., *Castanea* spp., *Cichorium endivia*, *Cinnamomum* spp., *Citrullus lanatus*, *Citrus* spp., *Cocos* spp., *Coffea* spp., *Cola* spp., *Colocasia esculenta*, *Corylus* spp., *Crataegus* spp., *Cucumis* spp., *Cucurbita* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp., *Gossypium hirsutum*, *Helianthus* spp., *Hibiscus* spp., *Hordeum* spp., *Ipomoea batatas*, *Juglans* spp., *Lactuca sativa*, *Lathyrus* spp., *Lemna* spp., *Lens culinaris*, *Linum usitatissimum*, *Litchi chinensis*, *Lotus* spp., *Luffa acutangula*, *Lupinus* spp., *Macrotyloma* spp., *Malpighia emarginata*, *Malus* spp., *Mammea americana*, *Mangifera indica*, *Manihot* spp., *Manilkara zapota*, *Medicago sativa*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Solanum* spp., *Sorghum bicolor*, *Spinacia* spp., *Syzygium* spp., *Tamarindus indica*, *Theobroma cacao*, *Trifolium* spp., *Triticosecale rimpaui*, *Triticum* spp., *Vaccinium* spp., *Vicia* spp., *Vigna* spp., *Vitis* spp., *Zea mays*, *Zizania palustris*, *Ziziphus* spp., amongst others.

According to a preferred feature of the present invention, the plant is a crop plant comprising soybean, sunflower, canola, alfalfa, rapeseed, cotton, tomato, potato or tobacco. Further preferably, the plant according to the present invention is a monocotyledonous plant such as sugar cane, most preferably a cereal, such as rice, maize, wheat, millet, barley, rye, oats or sorghum.

The activity of a CDKA protein may be modulated by modulating the levels of the CDKA protein. Alternatively, activity may also be modulated when there is no change in levels of a CDKA protein, this may occur when the intrinsic properties of the polypeptide are altered, for example by making a mutant. According to a preferred feature of the invention, modulated activity of the CDKA protein with a T161D-type mutation and/or modulated expression of a nucleic acid encoding this CDKA is introduced and/or increased activity of a CDKA protein with a T161D-type mutation and/or increased expression of a nucleic acid encoding this CDKA.

The terms "A-type CDK" or "CDKA" as defined herein may be used interchangeably and encompass any amino acid sequence having cyclin dependent kinase activity and which sequence when used in the construction of a CDK phylogenetic tree, such as the ones depicted in FIG. 1 and FIG. 2, clusters around the A-type CDKs rather than any of the other CDK groups and which amino acid sequence comprises a PSTAIRE amino acid sequence. A person skilled in the art could readily determine whether any amino acid sequence in question falls within the definition of an "A-type CDK" using known techniques and software for the making of such a phylogenetic tree, such as a GCG, EBI or CLUSTAL package, using default parameters (see for example Vandepoele et al. 2002). Upon construction of such a phylogenetic tree, sequences clustering in the A-type CDK group will be considered to fall within the definition of an "A-type CDK" or "CDKA", and will therefore be useful in performing the methods of the invention. Preferably the A-type CDK further comprises in increasing order of preference at least 75%, 80%, 85%, 90%, 95%, 96%, 97%, 98%, 99% or more overall sequence identity to the amino acid represented in GenBank accession CAA42922 (SEQ ID NO: 8) or to its mutant form represented by SEQ ID NO: 2. The overall sequence identity is determined using a global alignment algorithm, such as the Needleman Wunsch algorithm in the program GAP (GCG Wisconsin Package, Accelrys). Preferably, the A-type CDK belongs to the class 1 A-type CDKs (i.e. CDKA;1).

The term "T161D-type mutation" is defined herein as a mutation in a CDK of the conserved threonine corresponding to threonine 161 in human CDC2 or rice CDKA;1 into aspartic acid or glutamic acid. More particularly, the term "CDK having a T161D-type mutation" encompasses CDK proteins comprising a substitution of the conserved threonine in the T-loop by aspartic acid or glutamic acid; preferably a substitution by aspartic acid. Substitution of threonine by aspartic acid or glutamic acid in a protein results in the introduction of a negative charge, thus mimicking the negative charge of a phosphate group introduced by phosphorylation. Methods for introducing mutations in genes resulting in amino acid substitutions are well known in the art and include site-directed mutagenesis with oligonucleotides or by using PCR.

The various structural domains in a CDKA protein are well known (De Bondt et al., Nature 363, 595-602, 1993) and may be identified using specialised databases e.g. SMART (Schultz et al. (1998) Proc. Natl. Acad. Sci. USA 95, 5857-5864; Letunic et al. (2002) Nucleic Acids Res 30, 242-244; http://smart.embl-heidelberg.de/), InterPro (Mulder et al., (2003) Nucl. Acids. Res. 31, 315-318; http://www.ebi.ac.uk/interpro/), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), http://www.expasy.org/prosite/) or Pfam (Bateman et al., Nucleic Acids Research 30(1):276-280 (2002), http://www.sanger.ac.uk/Software/Pfam/).

The kinase domain of CDK is of an S_TKc-type (SMART accession number SM00220, InterPro accession number IPR002290), and has Ser/Thr kinase activity. The predicted active site (VLHRDLKPQNLLI, wherein D is the predicted catalytic residue) corresponds to the PROSITE signature PS00108. The ATP binding site (IGEGTYGVVYRARDKVTNETIALK) corresponds to the PROSITE signature PS00107.

Methods for the search and identification of A-type CDK homologues would be well within the realm of persons skilled in the art. Such methods comprise comparison of the sequences represented by SEQ ID NO 1 or 2, or by GenBank accession CAA42922, in a computer readable format, with sequences that are available in public databases such as MIPS (http://mips.gsf.de/), GenBank (http://www.ncbi.nim.nih.gov/Genbank/index.html) or EMBL Nucleotide Sequence Database (http://www.ebi.ac.uk/embl/index.html), using algorithms well known in the art for the alignment or comparison of sequences, such as GAP (Needleman and Wunsch, J. Mol. Biol. 48; 443-453 (1970)), BESTFIT (using the local homology algorithm of Smith and Waterman (Advances in Applied Mathematics 2; 482-489 (1981))), BLAST (Altschul, S. F., Gish, W., Miller, W., Myers, E. W. & Lipman, D. J., J. Mol. Biol. 215:403-410 (1990)), FASTA and TFASTA (W. R. Pearson and D. J. Lipman Proc. Natl. Acad. Sci. USA 85:2444-2448 (1988)). The software for performing BLAST analysis is publicly available through the National Centre for Biotechnology Information (NCBI). The homologues mentioned below were identified using BLAST default parameters (BLOSUM62 matrix, gap opening penalty 11 and gap extension penalty 1) and preferably the full-length sequences are used for analysis. These alignment methods also easily allow the identification of the conserved threonine that corresponds to threonine 161 in human CDC2 or rice CDKA;1 (SEQ ID NO: 8).

Examples of proteins falling under the definition of "A-type CDK or a homologue thereof" include the CDKs with a PSTAIRE motif, such as the proteins listed in Table 1. Persons skilled in the art are aware of the various techniques that may be used for introducing a T161D-type of mutation into these proteins to make them useful in the methods of the present invention.

TABLE 1 examples of plant A-type CDK proteins with their GenBank or PIR accession numbers (modified from Joubès et al., Plant Mol. Biol. 43, 607-620, 2000)

| Gene name | Species | Database accession | SEQ ID NO: |
|---|---|---|---|
| Allce; CDKA; 1 | *Allium cepa* | BAA21673.1 | 10 |
| Antma; CDKA; 1 | *Antirrhinum majus* | CAA66233.1 | 12 |
| Antma; CDKA; 2 | *Antirrhinum majus* | CAA66234.1 | 14 |
| Arath; CDKA; 1 | *Arabidopsis thaliana* | AAA32831.1 | 16 |
| Betvu; CDKA; 1 | *Beta vulgaris* | CAA96384.1 | 18 |
| Brana; CDKA; 1 | *Brassica napus* | AAA92823.1 | 20 |
| Cheru; CDKA; 1 | *Chenopodium rubrum* | CAA71242.1 | 22 |
| Glyma; CDKA; 1 | *Glycine max* | M93140* | 24 |
| Glyma; CDKA; 2 | *Glycine max* | M93139* | 26 |
| Lyces; CDKA; 1 | *Lycopersicon esculentum* | CAA76700.1 | 28 |
| Lyces; CDKA; 2 | *Lycopersicon esculentum* | CAA76701.1 | 30 |
| Medsa; CDKA; 1 | *Medicago sativa* | AAB41817.1 | 32 |

TABLE 1-continued examples of plant A-type CDK proteins with their GenBank or PIR accession numbers (modified from Joubès et al., Plant Mol. Biol. 43, 607-620, 2000)

| Gene name | Species | Database accession | SEQ ID NO: |
|---|---|---|---|
| Medsa; CDKA; 2 | *Medicago sativa* | CAA50038.1 | 34 |
| Nicta; CDKA; 1 | *Nicotiana tabacum* | AAB02567.1 | 36 |
| Nicta; CDKA; 1 | *Nicotiana tabacum* | AAB02568.1 | 38 |
| Nicta; CDKA; 3 | *Nicotiana tabacum* | BAA09369.1 | 40 |
| Orysa; CDKA; 1 | *Oryza sativa* | CAA42922.1 | 8 |
| Orysa; CDKA; 2 | *Oryza sativa* | CAA42923.1 | 42 |
| Petcr; CDKA; 1 | *Petroselinum crispum* | AAC41680.1 | 44 |
| Pethy; CDKA; 1 | *Petunia hybrida* | CAA73997.1 | 46 |
| Picab; CDKA; 1 | *Picea abies* | CAA54746.1 | 48 |
| Pinco; CDKA; 1 | *Pinus contorta* | CAA56815.2 | 50 |
| Pissa; CDKA; 2 | *Pisum sativum* | BAA33152 | 52 |
| Soltu; CDKA; 2 | *Solanum tuberosum* | AAA98856.1 | 54 |
| Sesro; CDKA; 1 | *Sesbania rostrata* | CAA99991.1 | 56 |
| Triae; CDKA; 1 | *Triticum aestivum* | AAD10483.1 | 58 |
| Triae; CDKA; 2 | *Triticum aestivum* | AAD10484.1 | 60 |
| Vigac; CDKA; 1 | *Vigna aconitifolia* | AAA34241.1 | 62 |
| Vigun; CDKA; 1 | *Vigna unguiculata* | CAA61581.1 | 64 |
| Zeama; CDKA; 1 | *Zea mays* | AAA33479 | 66 |

*GenBank accession numbers of the CDS encoding the protein.

It is to be understood that the term "A-type CDK or a homologue thereof" is not to be limited to the sequence represented by SEQ ID NO: 2, but that any polypeptide meeting the criteria of having cyclin dependent kinase activity, having a PSTAIRE domain, and having at least 75% sequence identity to SEQ ID NO: 8, may be suitable for use in the methods of the invention, provided that the CDKA or its homologue comprise a T161D-type mutation. Preferably, the A-type CDK or a homologue thereof is an orthologue of the protein represented by SEQ ID NO: 8.

To determine the kinase activity of A-type CDKs, several assays are available and are well known in the art (for example Current Protocols in Molecular Biology, Volumes 1 and 2, Ausubel et al. (1994), Current Protocols; or online, such as http://www.protocol-online.org).

In brief, the kinase assay generally involves: (1) bringing the kinase protein into contact with a substrate polypeptide containing the target site to be phosphorylated; (2) allowing phosphorylation of the target site in an appropriate kinase buffer under appropriate conditions; (3) separating phosphorylated products from non-phosphorylated substrate after a suitable reaction period. The presence or absence of kinase activity is determined by the presence or absence of the phosphorylated target. In addition, quantitative measurements may be performed. Purified CDK protein, or cell extracts containing or enriched with the CDK protein may be used as a source of the kinase protein. Histone H1 or small peptides are particularly well suited as a substrate. The peptide must comprise one or more serine, threonine, or tyrosine residues in a phosphorylation site motif. A compilation of phosphorylation sites may be found in Biochimica et Biophysica Acta 1314, 191-225, (1996). In addition, the peptide substrates may advantageously have a net positive charge to facilitate binding to phosphocellulose filters, (allowing separation of the phosphorylated from non-phosphorylated peptides and detection of the phosphorylated peptides). If a phosphorylation site motif is not known, a general Ser/Thr kinase substrate may be used. For example, the peptide "ADAQHATPPKKKRKVEDPKDF" (SEQ ID NO: 67) (Marshak et al. J. Cell. Biochem. 45, 391, 1991) is a specific substrate for A-type CDK. To determine the kinetic parameters for phosphorylation of the synthetic peptide, a range of peptide concentrations is required. For initial reactions, a peptide concentration of 0.7-1.5 mM may be used. For each kinase enzyme, it is important to determine the optimal buffer, ionic strength, and pH for activity. A standard 5× Kinase Buffer generally contains 5 mg/ml BSA (Bovine Serum Albumin preventing kinase adsorption to the assay tube), 150 mM Tris-Cl (pH 7.5), 100 mM $MgCl_2$. The optimal concentrations of divalent cations must be determined empirically for each protein kinase. Suitable buffers for CDK assays are known in the art (for example John et al., Protoplasma 161, 70-74, 1991). A commonly used donor of the phosphoryl group is radio-labelled [gamma-$^{32}$P]ATP (normally at 0.2 mM final concentration). The amount of $^{32}$P incorporated in the peptides may be determined by measuring activity on the nitrocellulose dry pads in a scintillation counter.

Furthermore, such "CDKA or homologue or derivative thereof", when comprising a T161D-type mutation and expressed under control of a shoot specific promoter in *Oryza sativa*, increases seed yield compared to corresponding wild type plants. This increase in seed yield may be measured in several ways, for example as an increase in the total weight of seeds, as an increase in the number of filled seeds harvested from a plant or as an increased Harvest Index.

The biological and/or functional activity of a CDKA or a homologue thereof according to the present invention includes at least one of having cyclin dependent kinase activity or having yield-increasing activity in plants as described above.

The present invention also provides an isolated mutant A-type cyclin dependent kinase (CDKA), selected from the group consisting of:
 (a) the amino acid sequence represented by SEQ ID NO: 2;
 (b) a homologue and/or a derivative of a protein as represented by SEQ ID NO: 2, which homologue or derivative is of plant origin and comprises a T161D-type mutation;
 (c) an active fragment of an amino acid sequence as defined in (a) or (b), which active fragment comprises a T161D-type mutation.

"Active fragments" of an A-type CDK protein encompasses at least 100 amino acid residues of an A-type CDK protein, including a PSTAIRE motif and a T161D-type mutation, which contiguous residues retain similar biological and/or functional activity to the naturally occurring protein that comprises the T161D-type mutation.

A CDKA or a homologue thereof as defined hereinabove is encoded by a CDKA nucleic acid molecule. The nucleic acid encoding a CDKA or a homologue thereof may be any natural or synthetic nucleic acid. Therefore the term "CDKA nucleic acid molecule" or "CDKA gene" as defined herein is any nucleic acid molecule (including those as a result of the degeneration of the genetic code) encoding a CDKA polypeptide or a homologue thereof as defined hereinabove. Examples of CDKA nucleic acid molecules include the one represented by SEQ ID NO: 1, and those encoding the above-mentioned homologues. CDKA nucleic acids and functional variants thereof may be suitable in practicing the methods of the invention, provided that they encode CDKA proteins or homologues thereof comprising a T161D-type mutation. Such functional variant CDKA nucleic acids include portions of a CDKA nucleic acid molecule, allelic variants, splice variants and/or nucleic acids capable of hybridising with a CDKA nucleic acid molecule. The term "functional" in the context of a functional variant refers to a variant (i.e. a portion or a hybridising sequence), which encodes a polypeptide having cyclin-dependent kinase activity and having a T161D-type mutation.

The present invention also provides an isolated nucleic acid molecule selected from the group consisting of:
a. a nucleic acid molecule encoding the amino acid sequence represented by SEQ ID NO: 2;
b. a nucleic acid molecule encoding a homologue, derivative or active fragment of the amino acid molecule represented by SEQ ID NO: 2, which homologue, derivative or fragment is of plant origin and comprises a PSTAIRE motif and a T161D-type mutation;
c. a nucleic acid molecule capable of hybridising with a nucleic acid of (a) or (b) above, or its complement, wherein the hybridising sequence or the complement thereof encodes a plant CDKA protein that comprises a PSTAIRE motif and a T161D-type mutation;
d. allelic variants of a nucleic acid according to any of (a) to (c) above, which allelic variants encode a plant CDKA protein comprising a PSTAIRE motif and a T161D-type mutation; and
e. alternative splice variants of a nucleic acid according to any of (a) to (c), which alternative splice variants encode a plant CDKA protein comprising a PSTAIRE motif and having a T161D-type mutation.

The term portion as defined herein refers to a piece of a DNA encoding a CDKA, comprising at least 300 nucleotides and which portion encodes a polypeptide having cyclin-dependent kinase activity, having a PSTAIRE motif and having a T161D-type mutation. A portion may be prepared, for example, by making one or more deletions to a CDKA nucleic acid. The portions may be used in isolated form or they may be fused to other coding (or non coding) sequences in order to, for example, produce a protein that combines several activities, one of them being cyclin-dependent kinase activity. When fused to other coding sequences, the resulting polypeptide produced upon translation may be bigger than that predicted for the CDKA fragment. Preferably, the functional portion is a portion of a CDKA nucleic acid, more preferably a portion of the nucleic acid molecule as represented by SEQ ID NO: 1.

Another variant of a CDKA nucleic acid molecule is a nucleic acid molecule capable of hybridising under reduced stringency conditions, preferably under stringent conditions, with a CDKA nucleic acid molecule as hereinbefore defined, which hybridising sequence encodes a CDKA polypeptide comprising a PSTAIRE motif and a T161D-type mutation. Preferably, the hybridising sequence is one that is capable of hybridising to the nucleic acid molecule of SEQ ID NO: 1, or to a nucleic acid encoding one of the above mentioned homologues, or to a portion of any of the aforementioned sequences. Most preferably, the hybridising sequence is capable of hybridising to the nucleic acid molecule of SEQ ID NO: 1.

The term "hybridisation" as defined herein is a process wherein substantially homologous complementary nucleotide sequences anneal to each other. The hybridisation process may occur entirely in solution, i.e. both complementary nucleic acids are in solution. The hybridisation process may also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

DNA-DNA hybrids (Meinkoth and Wahl, Anal. Biochem., 138: 267-284, 1984):

$$T_m = 81.5° C. + 16.6x \log [Na^+]^a + 0.41x\%[G/C^b] - 500x [L^c]^{-1} - 0.61x\% \text{ formamide}$$

DNA-RNA or RNA-RNA hybrids:

$$T_m = 79.8 + 18.5(\log_{10}[Na^+]^a) + 0.58 (\% G/C^b) + 11.8 (\% G/C^b)^2 - 820/L^c$$

oligo-DNA or oligo-RNA$^d$ hybrids:
For <20 nucleotides: $T_m = 2 (l_n)$
For 20-35 nucleotides: $T_m = 22 + 1.46 (l_n)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $l_n$, effective length of primer=(no. of G/C)+(no. of A/T).

Note: for each 1% formamide, the $T_m$ is reduced by about 0.6 to 0.7° C., while the presence of 6M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. More or less stringent conditions may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with Rnase.

Examples of hybridisation and wash conditions are listed in Table 2:

TABLE 2

| Stringency Condition | Polynucleotide Hybrid ± | Hybrid Length (bp)‡ | Hybridization Temperature and Buffer† | Wash Temperature and Buffer† |
|---|---|---|---|---|
| A | DNA:DNA | > or equal to 50 | 65° C. 1xSSC; or 42° C., 1xSSC and 50% formamide | 65° C.; 0.3xSSC |
| B | DNA:DNA | <50 | Tb*; 1xSSC | Tb*; 1xSSC |
| C | DNA:RNA | > or equal to 50 | 67° C. 1xSSC; or 45° C., 1xSSC and 50% formamide | 67° C.; 0.3xSSC |
| D | DNA:RNA | <50 | Td*; 1xSSC | Td*; 1xSSC |
| E | RNA:RNA | > or equal to 50 | 70° C. 1xSSC; or 50° C., 1xSSC and 50% formamide | 70° C.; 0.3xSSC |
| F | RNA:RNA | <50 | Tf*; 1xSSC | Tf*; 1xSSC |
| G | DNA:DNA | > or equal to 50 | 65° C. 4xSSC; or 45° C., 4xSSC and 50% formamide | 65° C.; 1xSSC |
| H | DNA:DNA | <50 | Th*; 4xSSC | Th*; 4xSSC |
| I | DNA:RNA | > or equal to 50 | 67° C. 4xSSC; or 45° C., 4xSSC and 50% formamide | 67° C.; 1xSSC |
| J | DNA:RNA | <50 | Tj*; 4xSSC | Tj*; 4xSSC |
| K | RNA:RNA | > or equal to 50 | 70° C. 4xSSC; or 40° C., 6xSSC and 50% formamide | 67° C.; 1xSSC |
| L | RNA:RNA | <50 | Tl*; 2xSSC | Tl*; 2xSSC |
| M | DNA:DNA | > or equal to 50 | 50° C. 4xSSC; or 40° C., 6xSSC and 50% formamide | 50° C.; 2xSSC |
| N | DNA:DNA | <50 | Tn*; 6xSSC | Tn*; 6xSSC |
| O | DNA:RNA | > or equal to 50 | 55° C. 4xSSC; or 42° C., 6xSSC and 50% formamide | 55° C.; 2xSSC |
| P | DNA:RNA | <50 | Tp*; 6xSSC | Tp*; 6xSSC |
| Q | RNA:RNA | > or equal to 50 | 60° C. 4xSSC; or 45° C., 6xSSC and 50% formamide | 60° C.; 2xSSC |
| R | RNA:RNA | <50 | Tr*; 4xSSC | Tr*; 4xSSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1xSSPE is 0.15M NaCl, 10 mM NaH$_2$PO$_4$, and 1.25 mM EDTA, pH 7.4) may be substituted for SSC (1xSSC is 0.15M NaCl and 15 mM sodium citrate) in the hybridisation and wash buffers; washes are performed for 15 minutes after hybridisation is complete. The hybridisations and washes may additionally include 5xDenhardt's reagent, 0.5-1.0% SDS, 100 μg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

For the purposes of defining the level of stringency, reference may conveniently be made to Sambrook et al. (2001) Molecular Cloning: a laboratory manual, 3$^{rd}$ Edition Cold Spring Harbor Laboratory Press, CSH, New York or to Current Protocols in Molecular Biology, John Wiley & Sons, N.Y. (1989).

After hybridisation and washing, the duplexes may be detected by autoradiography (when radiolabeled probes were used) or by chemiluminescence, immunodetection, by fluorescent or chromogenic detection, depending on the type of probe labelling. Alternatively, a ribonuclease protection assay may be performed for detection of RNA:RNA hybrids.

The CDKA nucleic acid molecule or variant thereof may be derived from any plant or artificial source. This nucleic acid may be modified from its native form in composition and/or genomic environment through deliberate human manipulation; the CDKA nucleic acids useful in the present invention have at least a mutation causing the T161D substitution. The nucleic acid is preferably of plant origin, whether from the same plant species (for example to the one in which it is to be introduced) or whether from a different plant species. The nucleic acid may be isolated from a monocotyledonous species, preferably from the family Poaceae, further preferably from *Oryza sativa*. More preferably, the CDKA isolated from *Oryza sativa* is CDKA;1. Most preferably, the CDKA;1 isolated from *Oryza sativa* and subsequently mutated is represented by SEQ ID NO: 1 and the CDKA amino acid sequence with the T161D-type mutation is as represented by SEQ ID NO: 2.

The activity of a CDKA polypeptide or a homologue thereof, having a T161D-type mutation, and/or expression of a nucleic acid encoding such a CDKA may be modulated by introducing a genetic modification (preferably in the locus of a CDKA gene). The locus of a gene as defined herein is taken to mean a genomic region which includes the gene of interest and 10 kb up- or downstream of the coding region.

The genetic modification may be introduced, for example, by any one (or more) of the following methods: TILLING, site-directed mutagenesis, directed evolution and homologous recombination or by introducing and expressing in a plant a nucleic acid encoding an A-type CDK polypeptide or a homologue thereof, which CDKA or homologue comprises a PSTAIRE motif and a T161D-type mutation. Following introduction of the genetic modification there follows a step of selecting for increased expression of a nucleic acid encoding a CDK polypeptide with a PSTAIRE motif and a T161D-type mutation and/or selecting for increased activity of a CDK polypeptide with a PSTAIRE motif and a T161D-type mutation, which increase in expression and/or activity gives plants having improved growth characteristics.

A genetic modification may also be introduced in the locus of a CDKA gene using the technique of TILLING (Targeted Induced Local Lesions IN Genomes). This is a mutagenesis technology useful to generate and/or identify, and to eventually isolate mutagenised variants of a nucleic acid molecule encoding an A-type CDK with a T161D-type mutation capable of exhibiting cyclin-dependent kinase activity. TILLING also allows selection of plants carrying such mutant variants. TILLING combines high-density mutagenesis with high-throughput screening methods. The steps typically followed in TILLING are: (a) EMS mutagenesis (Redei and Koncz (1992), In: C Koncz, N-H Chua, J Schell, eds, Methods in Arabidopsis Research. World Scientific, Singapore, pp 16-82; Feldmann et al., (1994) In: E M Meyerowitz, C R Somerville, eds, Arabidopsis. Cold Spring Harbor Laboratory Press, Cold Spring Harbor, N.Y., pp 137-172; Lightner and Caspar (1998), In: J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nature Biotechnol. 18, 455-457, 2000, Stemple Nature Rev. Genet. 5, 145-150, 2004).

Site-directed mutagenesis may be used to generate variants of CDKA nucleic acids or portions thereof that retain activity (such as cyclin-dependent kinase activity). Several methods are available to achieve site-directed mutagenesis, the most common being PCR based methods (See for example Ausubel et al., Current Protocols in Molecular Biology. Wiley Eds. http://www.4ulr.com/products/currentprotocols/index.html).

Directed evolution may also be used to generate variants of CDKA nucleic acids. This consists of iterations of DNA shuffling followed by appropriate screening and/or selection to generate variants of CDKA nucleic acids or portions thereof encoding CDKA polypeptides or homologues or portions thereof having a modified biological activity (Castle et al. (2004) Science 304(5674): 1151-4; U.S. Pat. Nos. 5,811,238 and 6,395,547).

TILLING, site-directed mutagenesis and directed evolution are examples of technologies that enable the generation novel alleles and variants of CDKA that retain CDKA function and which are therefore useful in the methods of the invention.

Homologous recombination allows introduction in a genome of a selected nucleic acid at a defined selected position. Homologous recombination is a standard technology used routinely in biological sciences for lower organism such as yeast or the moss *Physcomitrella*. Methods for performing homologous recombination in plants have been described not only for model plants (Offringa et al. (1990) EMBO J. 9, 3077-3084) but also for crop plants, for example rice (Terada et al., (2002) Nature Biotechnol. 20, 1030-1034; or Iida and Terada (2004) Curr. Opin. Biotechnol. 15, 132-138). The nucleic acid to be targeted (which may be a CDKA nucleic acid molecule or variant thereof as hereinbefore defined) need not be targeted to the locus of a CDKA gene, but may be introduced in, for example, regions of high expression. The nucleic acid to be targeted may be an improved allele used to replace the endogenous gene or may be introduced in addition to the endogenous gene.

A preferred method for introducing a genetic modification (which in this case need not be in the locus of a CDKA gene) is to introduce and express in a plant a nucleic acid encoding a CDKA polypeptide, or a homologue thereof, with a T161D-type mutation. A CDKA polypeptide or a homologue thereof as mentioned above, and suitable for practising the present invention, is one having cyclin-dependent kinase activity and, in increasing order of preference, having at least 75%, 80%, 85%, 90%, 95%, 96%, 97%, 98%, 99% or more sequence identity to the amino acid sequence represented by SEQ ID NO: 2 or SEQ ID NO: 8, and which CDK polypeptide comprises a PSTAIRE motif and a T161D-type mutation. The nucleic acid to be introduced into a plant may be a portion or a hybridising sequence as hereinbefore defined.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

Encompassed by the term "homologues" are orthologous and paralogous sequences, two special forms of homology, which encompass evolutionary concepts used to describe ancestral relationships of genes. Preferably the orthologues and paralogues useful in the present invention have the same structure and activity as an A-type CDK and have the highest similarity to SEQ ID NO: 8 in a reciprocal BLAST search and comprise a T161D-type mutation.

The term "paralogues" relates to homologous genes that result from one or more gene duplications within the genome of a species. Paralogues of a CDKA may easily be identified by performing a BLAST analysis against a set of sequences from the same species as the query sequence.

The term "orthologues" relates to homologous genes in different organisms due to ancestral relationship of these genes. Orthologues in, for example, monocot plant species may easily be found by performing a so-called reciprocal blast search. This may be done by a first blast involving blasting the sequence in question (for example, SEQ ID NO 15 or SEQ ID NO 16, being from *Arabidopsis thaliana*) against any sequence database, such as the publicly available NCBI database which may be found at: http://www.ncbi.nlm.nih.gov. If orthologues in rice were sought, the sequence in question would be blasted against, for example, the 28,469 full-length cDNA clones from *Oryza sativa* Nipponbare available at NCBI. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived, in casu *Arabidopsis thaliana*. The results of the first and second blasts are then compared. A paralogue is identified if a high-ranking hit from the second blast is from the same species as from which the query sequence is derived; an orthologue is identified if a highest ranking hit is not from the same species as from which the query sequence is derived. Such paralogue or orthologue is also considered a homologue of CDKA, provided that this homologue comprises a serine/threonine kinase domain and comprises a PSTAIRE motif. In the case of large families, ClustalW may be used, followed by the construction of a neighbour joining tree, to help visualize the clustering of related genes and identify orthologues and paralogues.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions (Table 3). To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). The substitutional variant useful in the methods of the present invention is a substitutional variant of a CDKA polypeptide and comprises a PSTAIRE motif and a T161D-type mutation.

TABLE 3

Examples of conserved amino acid substitutions:

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Less conserved substitutions may be made in case the above-mentioned amino acid properties are not so critical.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag 100 epitope, c-myc epitope, FLAG®-epitope, lacZ, CMP (calmodulin-binding peptide), HA epitope, protein C epitope and VSV epitope. The insertional variant useful in the methods of the present invention is a insertional variant of a CDKA polypeptide and comprises a PSTAIRE motif and a T161D-type mutation.

Homologues in the form of "deletion variants" of a protein are characterised by the removal of one or more amino acids from a protein, and encompass active fragments.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The CDKA polypeptide or homologue thereof with a PSTAIRE motif, may also be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in GenBank accession CAA42922 (SEQ ID NO: 8). "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. The derivative useful in the methods of the present invention is a derivative of a CDKA polypeptide and comprises a PSTAIRE motif and a T161D-type mutation.

The CDK type kinases in plants have a modular structure, consisting of an N-lobe and a C-lobe comprising a catalytic cleft and a T-loop (De Bondt et al. 1993). Therefore, it is envisaged that engineering of the domains of the kinase in such a way that the activity of the CDK protein is retained or modified, may result in the creation of a CDKA mutant that is useful for performing the methods of the invention. A preferred type of variant includes those generated by domain deletion, stacking or shuffling (see for example He et al., Science 288, 2360-2363, 2000; or U.S. Pat. Nos. 5,811,238 and 6,395,547), provided that the resulting CDKA comprises a PSTAIRE motif and a T161D-type mutation.

The CDKA polypeptide or homologue thereof may be encoded by an alternative splice variant of a CDKA nucleic acid molecule or gene. The term "alternative splice variant" as used herein encompasses variants of a nucleic acid sequence in which selected introns and/or exons have been excised, replaced or added. Such variants will be ones that encode polypeptides that comprise a T161D-type mutation and in which the biological activity of the protein is retained, which may be achieved by selectively retaining functional segments of the protein. Such splice variants may be found in nature or may be manmade. Methods for making such splice variants are well known in the art. Preferred splice variants are splice variants derived from the nucleic acid represented by SEQ ID NO 1. Further preferred are splice variants encoding a polypeptide retaining cyclin-dependent kinase activity and having a PSTAIRE motif and a T161D-type mutation.

The homologue may also be encoded by an allelic variant of a nucleic acid encoding a CDKA polypeptide or a homologue thereof, preferably an allelic variant of the nucleic acid represented by SEQ ID NO 1, provided that the polypeptide encoded by the allelic variant has cyclin-dependent kinase activity and comprises a PSTAIRE motif and a T161D-type mutation. Allelic variants exist in nature and encompassed within the methods of the present invention is the use of these natural alleles, provided that these alleles comprise a T161D-type mutation. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, enhanced or increased expression of the CDKA nucleic acid molecule or variant thereof according to the invention is envisaged. Methods for obtaining enhanced or increased expression (overexpression) of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a CDKA nucleic acid or variant thereof according to the invention. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene modified according to the present invention so as to control the expression of the gene.

If polypeptide expression is desired, it is generally desirable to include a polyadenylation region at the 3'-end of a polynucleotide coding region. The polyadenylation region may be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8, 4395-4405 (1988); Callis et al., Genes Dev. 1, 1183-1200 (1987)). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
(i) a CDKA nucleic acid molecule or functional variant thereof, which nucleic acid or variant encodes an A-type CDK comprising a PSTAIRE motif and a T161D-type mutation;
(ii) one or more control sequence(s) capable of driving expression in a plant of the nucleic acid sequence of (i); and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a CDKA nucleic acid or variant thereof according to the present invention). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which modulate gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. Additionally or alternatively, the promoter may be a constitutive promoter, i.e. a promoter that is expressed predominantly in at least one tissue or organ and predominantly at any life stage of the plant. Additionally or alternatively, the promoter may be a tissue-preferred or cell-preferred promoter, i.e. one that is capable of preferentially initiating transcription in certain tissues, such as the leaves, roots, seed tissue etc, or even in specific cells. Promoters able to initiate transcription only in certain tissues or cells are respectively referred to herein as "tissue-specific", and "cell-specific".

Preferably, the CDKA nucleic acid or variant thereof according to the invention is operably linked to a shoot-specific promoter. The term "shoot-specific" as defined herein refers to a promoter that is expressed predominantly in the shoot and at any stage in the life of the plant. The term "shoot" as used in herein encompasses all aerial parts of the plant, including stems and branches, leaves, buds, reproductive organs, including shoot-derived structures such as stolons, corms, rhizomes or tubers. Preferably, the shoot-specific promoter capable of preferentially expressing the nucleic acid throughout the shoot is a weak promoter. Promoter strength and/or expression pattern may be analysed for example by coupling the promoter to a reporter gene and assaying the expression of the reporter gene in various tissues of the plant. One suitable reporter gene well known to persons skilled in the art is beta-glucuronidase. Promoter strength and/or expression pattern can then be compared to that of a well-characterised shoot-specific reference promoter, such as the Cab27 promoter (weak expression, GenBank AP004700), or the putative protochlorophyllid reductase promoter (strong expression, GenBank AL606456). Reference to a "weak promoter" indicates a promoter that drives expression of a coding sequence at a low level, namely at levels of about $1/10,000$ transcripts to about $1/100,000$ transcripts, to about $1/500,0000$ transcripts per cell. Conversely, a "strong promoter" drives expression of a coding sequence at a high level, or at about $1/10$ transcripts to about $1/100$ transcripts to about $1/1,000$ transcripts per cell. Most preferably, the promoter capable of preferentially expressing the nucleic acid throughout the plant is a metallothionein promoter from rice as presented in SEQ ID NO: 6. It should be clear that the applicability of the present invention is not restricted to the CDKA nucleic acid represented by SEQ ID NO: 1, nor is the applicability of the invention restricted to expression of a CDKA nucleic acid when driven by the metallothionein promoter of SEQ ID NO: 6.

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence, which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes encoding proteins that confer resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Genes encoding visual marker proteins result in the formation of colour (for example β-glucuronidase, GUS), luminescence (such as luciferase) or fluorescence (Green Fluorescent Protein, GFP, and derivatives thereof).

The present invention also encompasses plants or plant cells obtainable by the methods according to the present invention. The present invention therefore provides plants or plant cells obtainable by the method according to the present invention, which plants or plant cells have introduced therein a CDKA nucleic acid or variant thereof, encoding a CDKA comprising a PSTAIRE motif and having a T161D-type mutation.

The invention also provides a method for the production of transgenic plant cells or transgenic plants having improved growth characteristics, comprising introduction and expression in a plant of a CDKA nucleic acid or a variant thereof, encoding a CDKA that comprises a PSTAIRE motif and having a T161D-type mutation.

More specifically, the present invention provides a method for the production of transgenic plants having improved growth characteristics, which method comprises:

(i) introducing into a plant or plant cell a nucleic acid encoding an A-type CDK or a homologue thereof comprising a T161D-type mutation; and (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al. (1982) Nature 296, 72-74; Negrutiu et al. (1987) Plant Mol. Biol. 8, 363-373); electroporation of protoplasts (Shillito et al. (1985) Bio/Technol 3, 1099-1102); microinjection into plant material (Crossway et al. (1986) Mol. Gen. Genet. 202, 179-185); DNA or RNA-coated particle bombardment (Klein et al. (1987) Nature 327, 70) infection with (non-integrative) viruses and the like. Transgenic rice plants expressing a CDKA according to the present invention are preferably produced via *Agrobacterium*-mediated transformation using any of the well known methods for rice transformation, such as described in any of the following: published European patent application EP 1198985 A1, Aldemita and Hodges (Planta 199, 612-617, 1996); Chan et al. (Plant Mol. Biol. 22, 491-506, 1993), Hiei et al. (Plant J. 6, 271-282, 1994), which disclosures are incorporated by reference herein as if fully set forth. In the case of corn transformation, the preferred method is as described in either Ishida et al. (Nature Biotechnol. 14, 745-50, 1996) or Frame et al. (Plant Physiol. 129, 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced or obtainable by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

The invention also includes host cells containing an isolated plant CDK nucleic acid or variant thereof, encoding an A-type CDK comprising a T161D-type mutation. Preferred host cells according to the invention are plant cells.

The invention also extends to harvestable parts of a plant according to the invention such as but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch and proteins.

The present invention furthermore encompasses the use of a T161D-type mutation in a CDKA protein for improving the growth characteristics of plants; such improved growth characteristics are as defined herein above.

The present invention also encompasses use of CDKA nucleic acids or variants thereof, and to use of CDKA polypeptides or homologues thereof, which CDKA or homologue comprises a T161D-type mutation, or which CDKA nucleic acid or variant encodes such a protein. One such use relates to improving the growth characteristics of plants, in particular in improving yield, especially seed yield. The seed yield may include any one or more of the following: increased total number of seeds, increased number of filled seeds, increased seed weight, increased harvest index, among others.

CDKA nucleic acids or variants thereof, or CDKA polypeptides or homologues thereof, may find use in breeding programmes in which a DNA marker is identified which may be genetically linked to a CDKA gene or variant thereof. The CDKA or variants thereof, or CDKA or homologues thereof, may be used to define a molecular marker. This DNA or protein marker may then be used in breeding programs to select plants having improved growth characteristics. The CDKA gene or variant thereof may, for example, be a nucleic acid as represented by SEQ ID NO: 1, or a nucleic acid encoding any of the homologues as defined herein.

Allelic variants of a CDKA, which variants comprise a T161D mutation, may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give improved growth characteristics in a plant. Selection is typically carried out by monitoring growth performance of plants containing different allelic variants of the sequence in question, for example, different allelic variants of SEQ ID NO: 1, or of nucleic acids encoding any of the above mentioned homologues. Growth performance may be monitored in a greenhouse or in the field. Further optional steps include crossing plants, in which the superior allelic variant was identified, with another plant. This could be used, for example, to make a combination of interesting phenotypic features.

CDKA nucleic acids or variants thereof according to the invention may also be used as probes for genetically and physically mapping the genes that they are a part of, and as markers for traits linked to those genes. Such information may be useful in plant breeding in order to develop lines with desired phenotypes. Such use of CDKA nucleic acids or variants thereof requires only a nucleic acid sequence of at least 15 nucleotides in length. The CDKA nucleic acids or variants thereof may be used as restriction fragment length polymorphism (RFLP) markers. Southern blots of restriction-digested plant genomic DNA may be probed with the CDKA nucleic acids or variants thereof. The resulting banding patterns may then be subjected to genetic analyses using computer programs such as MapMaker (Lander et al. (1987) Genomics 1, 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the CDKA nucleic acid or variant thereof in the genetic map previously obtained using this population (Botstein et al. (1980) Am. J. Hum. Genet. 32, 314-331).

The production and use of plant gene-derived probes for use in genetic mapping is described in Bernatzky and Tanksley (Genetics 112, 887-898, 1986). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7, 149-154). Although current methods of FISH mapping favour use of large clones (several to several hundred kb; see Laan et al. (1995) Genome Res. 5, 13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med. 11, 95-96), polymorphism of PCR-amplified fragments (CAPS; Sheffield et al. (1993) Genomics 16, 325-332), allele-specific ligation (Landegren et al. (1988) Science 241, 1077-1080), nucleotide extension reactions (Sokolov (1990) Nucleic Acid Res. 18, 3671), Radiation Hybrid Mapping (Walter et al. (1997) Nat. Genet. 7, 22-28) and Happy Mapping (Dear and Cook (1989) Nucleic Acid Res. 17, 6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In this way, generation, identification and/or isolation of improved plants with modulated cyclin-dependent kinase activity displaying improved growth characteristics may be performed.

CDKA nucleic acids or variants thereof or CDKA polypeptides or homologues thereof according to the present invention may also find use as growth regulators. Since these molecules have been shown to be useful in improving the growth characteristics of plants, they would also be useful growth regulators, such as herbicides or growth stimulators. The present invention therefore provides a composition comprising a CDKA or variant thereof or a CDKA polypeptide or homologue thereof, together with a suitable carrier, diluent or excipient, for use as a growth regulator, which CDKA or homologue comprises a T161D mutation, or which CDKA or variant encodes such protein.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 3 details examples of sequences useful in performing the methods according to the present invention. SEQ ID NO 1 and SEQ ID NO 2 represent the nucleotide and protein sequence of the CDKA used in the examples. Start and stop codon are indicated in bold in SEQ ID NO: 1; the mutation is indicated in bold underlined in SEQ ID NO: 1 and 2. SEQ ID NO 3 and SEQ ID NO 4 are primer sequences used for isolating the CDKA;1 nucleic acid. SEQ ID NO: 5 represents the expression cassette used in the present invention, comprising the metallothionein promoter (internal reference PRO0109, nucleotides 1-1208), the coding sequence for the mutated CDKA (internal reference CDS0644_1 (nt 1285-2170) and the terminator (nt 2275-2709). SEQ ID NO: 6 is the sequence of the metallothionein promoter.

EXAMPLES

Figure 1:
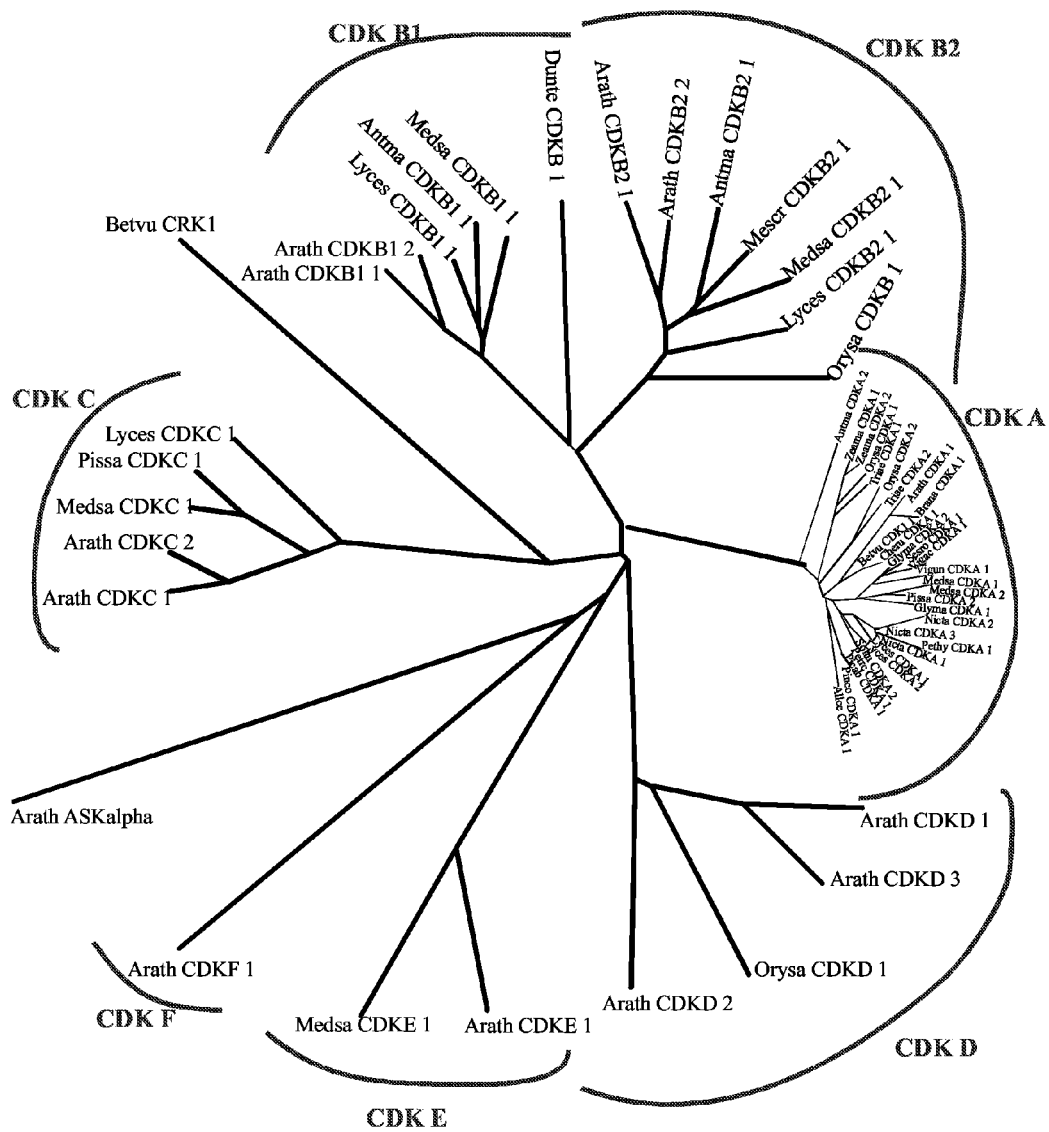
FIG. 1 gives a phylogenetic tree of cyclin dependent kinases with a PSTAIRE motif (or A-type CDKs).
Figure 2:
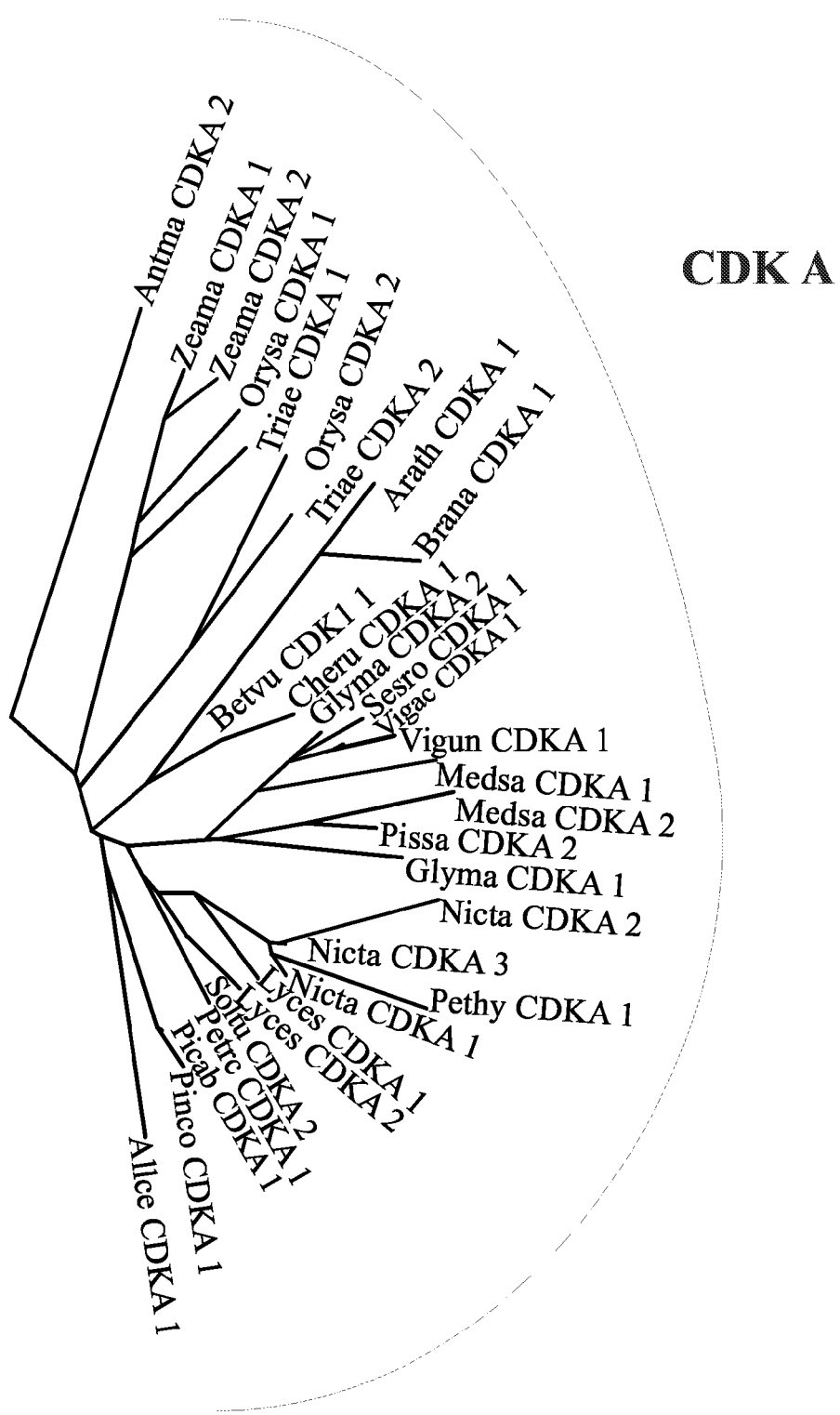
FIG. 2 shows the cluster of A-type CDKs of FIG. 1 in more detail.

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols (http://www.4ulr.com/products/currentprotocols/index.html). Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Gene Cloning

The *Oryza sativa* CDKA;1 was cloned and subsequently mutagenised for introducing the T161D substitution using standard techniques. Next the mutant CDKA;1 (internal code CDS0644-7) was amplified by PCR using Hifi Taq DNA polymerase in standard conditions and primers Prm04553 (SEQ ID NO 3, sense) and Prm04554 (SEQ ID NO 4, reverse complementary), which include the AttB sites for Gateway recombination. The resulting PCR fragment was purified with standard methods. The first step of the Gateway procedure, the BP reaction, was then performed, during which the PCR fragment recombines in vivo with the pDONR201 plasmid to produce, according to the Gateway® terminology, an "entry clone", p06. Plasmid pDONR201 was purchased from Invitrogen, as part of the Gateway® technology.

Example 2

Vector Construction and Rice Transformation

The entry clone p06 was subsequently used in an LR reaction with p03390, a destination vector used for *Oryza sativa* transformation. This vector contained as functional elements within the T-DNA borders: a plant selectable marker; a visual marker expression cassette; and a Gateway cassette intended for LR in vivo recombination with the sequence of interest already cloned in the entry clone. A rice metallothionein promoter for shoot specific expression was located upstream of this Gateway cassette.

After the LR recombination step, the resulting expression vector p017, comprising the expression cassette SEQ ID NO: 5, was transformed into the *Agrobacterium* strain LBA4404 and subsequently to *Oryza sativa* plants. Transformed rice plants were allowed to grow and were then examined for the parameters described in Example 3.

Example 3

Evaluation of Transformants: Growth Measurements

Approximately 15 to 20 independent TO transformants were generated. The primary transformants were transferred from tissue culture chambers to a greenhouse for growing and harvest of T1 seed. Four events of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by visual marker screening. The selected T1 plants were transferred to a greenhouse. Each plant received a unique barcode label to unambiguously link the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also referred to herein as a "global gene effect". If the value of the F test showed that the data were significant, than it was concluded that there was a "gene" effect, meaning that not only presence or the position of the gene that was causing the effect. The threshold for significance for a true global gene effect was set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" refer to the plants treated in the same way as the transgenic plant, but from which the transgene has segregated. Null plants can also be described as the homozygous negative transformed plants. The threshold for significance for the t-test was set at a 10% probability level. The results for some events can be above or below this threshold. This is based on the hypothesis that a gene might only have an effect in certain positions in the genome, and that the occurrence of this position-dependent effect is not uncommon. This kind of gene effect is also referred to herein as a "line effect of the gene". The p-value was obtained by comparing the t-value to the t-distribution or alternatively, by comparing the F-value to the F-distribution. The p-value then gives the probability that the null hypothesis (i.e., that there is no effect of the transgene) is correct.

The data obtained in the first experiment were confirmed in a second experiment with T2 plants. Three lines were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 120 transformed plants were evaluated in the T2 generation, that is 40 plants per event of which 20 were positive for the transgene and 20 negative.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values were obtained by comparing likelihood ratio test to chi square distributions.

Example 4

Evaluation of Transformants: Measurement of Yield-Related Parameters

Upon analysis of the seeds as described above, the inventors found that plants transformed with the CDK gene construct encoding an A-type CDK with a T161D-type mutation had an increased number of filled seeds, an increased total weight of seeds and an increased harvest index compared to plants lacking the CDKA transgene.

Positive results obtained for plants in the T1 generation were again obtained in the T2 generation. In Table 4, data show overall % increases for biomass and TKW, calculated from the data of the individual lines of the T2 generation, and the respective p-values. These T2 data were re-evaluated in a combined analysis with the results for the T1 generation, and the obtained p-values show that the observed effects were significant (Table 4).

TABLE 4

| parameter | T1 generation | | T2 generation | | Combined |
|---|---|---|---|---|---|
| | Overall % increase | p-value of F-test | Overall % increase | p-value of F-test | analysis p-value |
| Number filled seeds | 62 | 0.0012 | 16 | 0.0230 | 0.0000 |
| Total weight of seeds | 60 | 0.0019 | 15 | 0.0392 | 0.0002 |
| Harvest Index | 82 | 0.0000 | 14 | 0.0110 | 0.0000 |

Number of Filled Seeds

The number of filled seeds was determined by counting the number of filled husks that remained after the separation step. 3 out of the 4 tested lines showed an increase in filled seed number, amounting to 186%. There was an overall increase of 62% in the number of filled seeds produced by transgenic plants relative to corresponding null segregants, which increase is statistically significant (p-value 0.0012). In the T2 generation, there was increase for 2 of the 3 tested lines. The mean increase for the T2 lines was 14%, this mean increase was also statistically significant (p-value of 0.0230). The combined analysis of T1 and T2 data also confirmed that the global gene effect was highly significant (p-value of 0.0000).

Total Seed Yield

The total seed yield (total weight of seeds) per plant was measured by weighing all filled husks harvested from a plant. 3 of the 4 transgenic T1 lines showed an increase in total seed weight, which varied between 43 and 178%. On average, the increase in seed yield was 60% and this overall effect from the presence of the transgene on seed yield was significant, as evidenced by a P-value from the F test of 0.0019. These results were also observed in the T2 generation. The 3 tested lines had a yield increase between 14 and 48% with an average of 28%. The mean increase (15%) was statistically significant (p-value of 0.0392) and also the combined analysis of the T1 and T2 plants showed there was a global gene effect (p-value of 0.0002).

Harvest Index

The harvest index in the present invention is defined herein as the ratio between the total seed yield and the above ground area ($mm^2$), multiplied by a factor $10^6$. All 4 tested lines showed an increased harvest index, ranging between 9 and 229%. There was a significant overall gene effect (an effect associated with of the presence of the transgene) on harvest index (an overall increase of 82%), with a statistically significant p-value for the F test of 0.0000. Similar results were obtained for T2 plants. The harvest index showed an overall increase of 17% (p-value of 0.0110). Here too, the combined analysis of the T1 and T2 data showed a global gene effect (p-value 0.0000).

Furthermore, there was a tendency for an increased total number of seeds. 3 of the 4 T1 lines showed an increase in the total number of seeds (overall increase 15%), these results were confirmed in the T2 generation (overall increase 9%) and upon a combined analysis these increases were shown to be significant (p-value of 0.0211).

The invention claimed is:

1. A method for improving plant growth characteristics relative to a corresponding wild-type plant, comprising introducing and expressing in a plant a nucleic acid encoding an A-type cyclin dependent kinase (CDK) with a T161D-type mutation.

2. The method according to claim 1, wherein said nucleic acid encoding an A-type CDK with a T161D-type mutation is overexpressed in a plant.

3. The method according to claim 1, wherein said nucleic acid encoding an A-type CDK with a T161D-type mutation is derived from a plant.

4. The method according to claim 1, wherein said nucleic acid encoding an A-type CDK having a T161D-type mutation is operably linked to a promoter capable of expressing said nucleic acid predominantly in shoots.

5. The method according to claim 4, wherein said promoter is the rice metallothionein promoter of SEQ ID NO: 6.

6. The method according to claim 1, wherein said improved plant growth characteristic is increased yield relative to corresponding wild type plants.

7. The method according to claim 6, wherein said increased yield is increased seed yield.

8. The method according to claim 7, wherein said increased seed yield is selected from any one or more of: (i) increased seed weight; (ii) increased total number of seeds; (iii) increased number of filled seeds; (iv) increased harvest index.

9. A plant, plant part or plant cell obtained by the method of claim 1.

10. A method for the production of a transgenic plant having improved growth characteristics relative to a corresponding wild-type plant, which method comprises:
(i) introducing into a plant or plant cell a nucleic acid encoding an A-type cyclin dependent kinase (CDK) or a homologue thereof, comprising a T161D-type mutation;
(ii) cultivating the plant or plant cell under conditions promoting plant growth and development.

11. A transgenic plant, plant part or plant cell having improved growth characteristics relative to a corresponding wild-type plant resulting from introducing a nucleic acid encoding an A-type cyclin dependent kinase (CDK) having a T161D-type mutation into said plant.

12. The plant, plant part or plant cell according to claim 11, wherein said plant is a monocotyledonous plant.

13. Harvestable parts of the transgenic plant according to claim 11 and/or products derived from said plants, wherein the harvestable parts and/or products comprise the nucleic acid.

14. The harvestable parts according to claim 13, wherein said harvestable parts are seeds which are true breeding for an isolated nucleic acid encoding an A-type CDK having a T161D-type mutation.

15. The method of claim 1, wherein the nucleic acid is derived from a monocotyledonous plant.

16. The method of claim 15, wherein the monocotyledonous plant is from the family Poaceae.

17. The method of claim 15, wherein the monocotyledonous plant is or sativa.

18. The plant, plant part or plant cell of claim 11, wherein the plant is selected from the group consisting of sugar cane, rice, maize, wheat, barley, millet, rye oats, and sorghum.

* * * * *

UNITED STATES PATENT AND TRADEMARK OFFICE
CERTIFICATE OF CORRECTION

PATENT NO.       : 7,847,157 B2                                                        Page 1 of 1
APPLICATION NO.  : 11/792001
DATED            : December 7, 2010
INVENTOR(S)      : Wim Van Camp It is certified that error appears in the above-identified patent and that said Letters Patent is hereby corrected as shown below:

In Claim 17, in column 122, on line 50, "or sativa" should read -- *Oryza sativa* --.

In Claim 18, in column 122, on line 53, "rye oats" should read -- rye, oats --.

Signed and Sealed this
First Day of March, 2011

David J. Kappos
*Director of the United States Patent and Trademark Office*